US012636382B2

(12) United States Patent
Gao et al.

(10) Patent No.:  US 12,636,382 B2
(45) **Date of Patent:  *May 26, 2026**

(54) PROSTATE TARGETING ADENO-ASSOCIATED VIRUS SEROTYPE VECTORS

(71) Applicant: University of Massachusetts, Westborough, MA (US)

(72) Inventors: Guangping Gao, Worcester, MA (US); Jianzhong Ai, Worcester, MA (US); Hong Li, Worcester, MA (US); Qiang Wei, Worcester, MA (US)

(73) Assignee: University of Massachusetts, Westborough, MA (US)

( * ) Notice: Subject to any disclaimer, the term of this patent is extended or adjusted under 35 U.S.C. 154(b) by 970 days.

This patent is subject to a terminal disclaimer.

(21) Appl. No.: 17/813,451

(22) Filed: Jul. 19, 2022

(65) Prior Publication Data

US 2023/0073187 A1     Mar. 9, 2023

Related U.S. Application Data

(63) Continuation of application No. 15/769,953, filed as application No. PCT/US2016/058185 on Oct. 21, 2016, now Pat. No. 11,426,469.

(60) Provisional application No. 62/322,285, filed on Apr. 14, 2016, provisional application No. 62/245,027, filed on Oct. 22, 2015.

(51) Int. Cl.

| | |
|---|---|
| *A61K 48/00* | (2006.01) |
| *A61K 9/00* | (2006.01) |
| *A61K 38/17* | (2006.01) |
| *A61P 35/00* | (2006.01) |
| *C07K 14/005* | (2006.01) |
| *C07K 14/075* | (2006.01) |
| *C07K 14/47* | (2006.01) |
| *C12N 5/10* | (2006.01) |
| *C12N 15/86* | (2006.01) |

(52) U.S. Cl.
CPC ........ *A61K 48/0058* (2013.01); *A61K 9/0019* (2013.01); *A61K 9/0034* (2013.01); *A61K 38/1709* (2013.01); *A61K 48/00* (2013.01); *A61P 35/00* (2018.01); *C07K 14/005* (2013.01); *C07K 14/075* (2013.01); *C12N 5/10* (2013.01); *C12N 15/86* (2013.01); *C07K 14/47* (2013.01); *C12N 2750/10041* (2013.01); *C12N 2750/14121* (2013.01); *C12N 2750/14122* (2013.01); *C12N 2750/14143* (2013.01); *C12N 2750/14145* (2013.01); *C12N 2840/007* (2013.01)

(58) Field of Classification Search
None
See application file for complete search history.

(56) References Cited

U.S. PATENT DOCUMENTS

| | | |
|---|---|---|
| 5,478,745 A | 12/1995 | Samulski et al. |
| 5,871,982 A | 2/1999 | Wilson et al. |
| 6,156,303 A | 12/2000 | Russell et al. |
| 6,251,677 B1 | 6/2001 | Wilson et al. |
| 6,485,966 B2 | 11/2002 | Gao et al. |
| 6,498,244 B1 | 12/2002 | Patel et al. |
| 6,544,786 B1 | 4/2003 | Xiao et al. |
| 6,953,690 B1 | 10/2005 | Gao et al. |
| 6,962,815 B2 | 11/2005 | Bartlett |
| 7,022,519 B2 | 4/2006 | Gao et al. |
| 7,198,951 B2 | 4/2007 | Gao et al. |
| 7,235,393 B2 | 6/2007 | Gao et al. |
| 7,267,978 B1 | 9/2007 | Carey et al. |
| 7,282,199 B2 | 10/2007 | Gao et al. |
| 7,427,396 B2 | 9/2008 | Arbetman et al. |
| 7,456,015 B2 | 11/2008 | Bohn et al. |
| 7,906,111 B2 | 3/2011 | Wilson et al. |
| 8,222,221 B2 | 7/2012 | Corey et al. |
| 8,524,446 B2 | 9/2013 | Gao et al. |
| 8,734,809 B2 | 5/2014 | Gao et al. |
| 9,249,424 B2 | 2/2016 | Wolf et al. |
| 9,701,984 B2 | 7/2017 | Gao et al. |
| 11,426,469 B2 | 8/2022 | Gao et al. |
| 2001/0016355 A1 | 8/2001 | Samulski et al. |
| 2002/0164783 A1 | 11/2002 | Feldhaus |
| 2002/0192823 A1 | 12/2002 | Bartlett |
| 2003/0103939 A1 | 6/2003 | Engelhardt et al. |
| 2003/0110526 A1 | 6/2003 | Brown et al. |
| 2003/0138772 A1 | 7/2003 | Gao et al. |
| 2003/0228282 A1 | 12/2003 | Gao et al. |
| 2004/0101514 A1 | 5/2004 | Liu et al. |
| 2005/0014262 A1 | 1/2005 | Gao et al. |

(Continued)

FOREIGN PATENT DOCUMENTS

| | | | |
|---|---|---|---|
| EP | 2261242 A1 | 12/2010 |
| EP | 2468891 A2 | 6/2012 |

(Continued)

OTHER PUBLICATIONS

Extended European Search Report for Application No. 16858324.3, mailed May 15, 2019.

(Continued)

*Primary Examiner* — Christopher M Babic
*Assistant Examiner* — Kimberly A Aron
(74) *Attorney, Agent, or Firm* — Wolf, Greenfield & Sacks, P.C.

(57) ABSTRACT

The disclosure relates to compositions and methods for rAAV-mediated delivery of a transgene to a subject. In some embodiments, the rAAV transduces the prostate tissue of a subject. In some embodiments, the methods are useful for treatment of prostate disease (e.g., prostatitis, BPH, prostate cancer).

17 Claims, 20 Drawing Sheets

Specification includes a Sequence Listing.

(56) References Cited

U.S. PATENT DOCUMENTS

| | | |
|---|---|---|
| 2005/0164970 A1 | 7/2005 | Li |
| 2005/0197313 A1 | 9/2005 | Roelvink |
| 2005/0255086 A1 | 11/2005 | Davidson et al. |
| 2005/0255089 A1 | 11/2005 | Chiorini et al. |
| 2005/0287122 A1 | 12/2005 | Bartlett et al. |
| 2006/0018841 A1 | 1/2006 | Arbetman et al. |
| 2006/0063174 A1 | 3/2006 | Turner et al. |
| 2006/0093589 A1 | 5/2006 | Warrington et al. |
| 2006/0153826 A1 | 7/2006 | Arnould et al. |
| 2006/0189564 A1 | 8/2006 | Burright et al. |
| 2006/0228800 A1 | 10/2006 | Lin et al. |
| 2006/0239968 A1 | 10/2006 | Arap et al. |
| 2006/0292117 A1 | 12/2006 | Loiler et al. |
| 2007/0036760 A1 | 2/2007 | Wilson et al. |
| 2007/0243526 A1 | 10/2007 | Kay et al. |
| 2008/0075737 A1 | 3/2008 | Gao et al. |
| 2008/0292595 A1 | 11/2008 | Arbetman et al. |
| 2009/0042828 A1 | 2/2009 | Xu et al. |
| 2009/0111766 A1 | 4/2009 | Atkinson et al. |
| 2009/0149409 A1 | 6/2009 | Bohn et al. |
| 2009/0197338 A1 | 8/2009 | Vandenberghe et al. |
| 2009/0215879 A1 | 8/2009 | DiPrimio et al. |
| 2009/0227533 A1 | 9/2009 | Bader et al. |
| 2010/0104561 A1 | 4/2010 | Zhong et al. |
| 2010/0227909 A1 | 9/2010 | Cleary et al. |
| 2010/0323001 A1 | 12/2010 | Pachuk |
| 2011/0171262 A1 | 7/2011 | Bakker et al. |
| 2011/0172293 A1 | 7/2011 | Fish et al. |
| 2011/0212520 A1 | 9/2011 | Davidson et al. |
| 2011/0258716 A1 | 10/2011 | Baltimore et al. |
| 2012/0077870 A1 | 3/2012 | Blanks et al. |
| 2012/0137379 A1 | 5/2012 | Gao et al. |
| 2012/0270930 A1 | 10/2012 | Van Der Maarel et al. |
| 2012/0309050 A1 | 12/2012 | Kumon et al. |
| 2013/0030042 A1 | 1/2013 | Couto |
| 2013/0101558 A1 | 4/2013 | Gao et al. |
| 2013/0109742 A1 | 5/2013 | Hewitt et al. |
| 2013/0142861 A1 | 6/2013 | Tsou et al. |
| 2013/0195801 A1 | 8/2013 | Gao et al. |
| 2013/0323226 A1 | 12/2013 | Wilson et al. |
| 2014/0142161 A1 | 5/2014 | Flotte et al. |
| 2014/0142288 A1 | 5/2014 | Davidson et al. |
| 2014/0147418 A1 | 5/2014 | Chiorini et al. |
| 2014/0179770 A1 | 6/2014 | Zhang et al. |
| 2014/0201857 A1 | 7/2014 | Fahrenkrug et al. |
| 2014/0335054 A1 | 11/2014 | Gao et al. |
| 2015/0065560 A1 | 3/2015 | Björklund et al. |
| 2015/0258180 A1 | 9/2015 | Mahuran et al. |
| 2016/0017005 A1 | 1/2016 | Asokan et al. |
| 2016/0060624 A1 | 3/2016 | Davidson et al. |
| 2016/0076054 A1 | 3/2016 | Auricchio et al. |
| 2016/0153005 A1 | 6/2016 | Zhang et al. |
| 2016/0185832 A1 | 6/2016 | Drivas et al. |
| 2016/0194374 A1 | 7/2016 | Wijnholds et al. |
| 2016/0272976 A1 | 9/2016 | Kaspar |
| 2017/0029785 A1 | 2/2017 | Zhao et al. |
| 2017/0114340 A1 | 4/2017 | Mueller et al. |
| 2017/0165377 A1 | 6/2017 | Gao et al. |
| 2018/0311380 A1 | 11/2018 | Gao et al. |

FOREIGN PATENT DOCUMENTS

| | | |
|---|---|---|
| JP | 2008-538286 | 10/2008 |
| WO | WO 2003/042397 | 5/2003 |
| WO | WO 2004/108922 A2 | 12/2004 |
| WO | WO 2005/033321 | 4/2005 |
| WO | WO 2006/031267 A2 | 3/2006 |
| WO | WO 2006/066066 A2 | 6/2006 |
| WO | WO 2006/119432 A2 | 11/2006 |
| WO | WO 2008/125846 A2 | 10/2008 |
| WO | WO 2008/150897 A2 | 12/2008 |
| WO | WO 2008/154333 A2 | 12/2008 |
| WO | WO 2009/43936 | 4/2009 |
| WO | WO 2009/146178 A1 | 12/2009 |
| WO | WO 2010/027446 A2 | 3/2010 |
| WO | WO 2010/071454 A1 | 6/2010 |
| WO | WO 2010/099383 A2 | 9/2010 |
| WO | WO 2010/129021 A1 | 11/2010 |
| WO | WO 2010/138263 A2 | 12/2010 |
| WO | WO 2011/094198 A1 | 8/2011 |
| WO | WO 2012/123430 A1 | 9/2012 |
| WO | WO 2013/055865 A1 | 4/2013 |
| WO | WO 2013/123503 A1 | 8/2013 |
| WO | WO 2013/170078 A1 | 11/2013 |
| WO | WO 2013/190059 A1 | 12/2013 |
| WO | WO 2014/160092 A1 | 10/2014 |
| WO | WO 2014/186746 A1 | 11/2014 |
| WO | WO 2014/197748 A2 | 11/2014 |
| WO | WO 2015/121501 A1 | 8/2015 |
| WO | WO 2015/164786 | 10/2015 |
| WO | WO 2015/168666 A2 | 11/2015 |
| WO | WO 2016/065001 A1 | 4/2016 |
| WO | WO 2017/023724 A1 | 2/2017 |

OTHER PUBLICATIONS

Invitation to Pay Additional Fees for Application No. PCT/US2016/058185, mailed Jan. 18, 2017.

International Search Report and Written Opinion for Application No. PCT/US2016/058185, mailed Mar. 27, 2017.

International Preliminary Report on Patentability for Application No. PCT/US2016/058185, mailed May 3, 2018.

Dash et al., Developing an effective gene therapy for prostate cancer: New technologies with potential to translate from the laboratory into the clinic. Discov Med. Jan. 2011;11(56):46-56.

Limberis et al., Transduction efficiencies of novel AAV vectors in mouse airway epithelium in vivo and human ciliated airway epithelium in vitro. Mol Ther. Feb. 2009;17(2):294-301. doi: 10.1038/mt.2008.261. Epub Dec. 9, 2008.

Liu et al., The microRNA miR-34a inhibits prostate cancer stem cells and metastasis by directly repressing CD44. Nat Med. Feb. 2011;17(2):211-5. doi: 10.1038/nm.2284. Epub Jan. 16, 2011.

Sayroo et al., Development of novel AAV serotype 6 based vectors with selective tropism for human cancer cells. Gene Ther. Jan. 2016;23(1):18-25. doi: 10.1038/gt.2015.89. Epub Oct. 8, 2015.

Adachi et al., Drawing a high-resolution functional map of adeno-associated virus capsid by massively parallel sequencing. Nat Commun. 2014;5:3075. doi: 10.1038/ncomms4075.

Ahmed et al., A Single Intravenous rAAV Injection as Late as P20 Achieves Efficacious and Sustained CNS Gene Therapy in Canavan Mice. Mol Ther. Jul. 2, 2013. doi: 10.1038/mt.2013.138. [Epub ahead of print].

Akache et al., The 37/67-kilodalton laminin receptor is a receptor for adeno-associated virus serotypes 8, 2, 3, and 9. J Virol. Oct. 2006;80(19):9831-6.

Arbetman et al., Novel caprine adeno-associated virus (AAV) capsid (AAV-Go.1) is closely related to the primate AAV-5 and has unique tropism and neutralization properties. J Virol. Dec. 2005;79(24):15238-45.

Arbuthnot et al., Hepatic delivery of RNA interference activators for therapeutic application. Curr Gene Ther. Apr. 2009;9(2):91-103.

Asokan et al., The AAV vector toolkit: poised at the clinical crossroads. Mol Ther. Apr. 2012;20(4):699-708. doi: 10.1038/mt.2011.287. Epub Jan. 24, 2012.

Baek et al., AAV-mediated gene delivery in adult GM1-gangliosidosis mice corrects lysosomal storage in CNS and improves survival. PLoS One. Oct. 18, 2010;5(10):e13468. doi: 10.1371/journal.pone.0013468.

Bals et al., Transduction of well-differentiated airway epithelium by recombinant adeno-associated virus is limited by vector entry. J Virol. Jul. 1999;73(7):6085-8.

Berns et al., Biology of adeno-associated virus. Curr Top Microbiol Immunol. 1996;218:1-23.

Beutler et al., AAV for pain: steps towards clinical translation. Gene Ther. Apr. 2009;16(4):461-9. Epub Mar. 5, 2009.

Bish et al., Adeno-associated virus (AAV) serotype 9 provides global cardiac gene transfer superior to AAV1, AAV6, AAV7, and AAV8 in the mouse and rat. Hum Gene Ther. Dec. 2008;19(12):1359-68. doi: 10.1089/hum.2008.123.

(56)             References Cited

OTHER PUBLICATIONS

Borel et al., Recombinant AAV as a platform for translating the therapeutic potential of RNA interference. Mol Ther. Apr. 2014;22(4):692-701. doi: 10.1038/mt.2013.285. Epub Dec. 19, 2013.
Bourdenx et al., Systemic gene delivery to the central nervous system using Adeno-associated virus. Front Mol Neurosci. Jun. 2, 2014;7:50. doi: 10.3389/fnmol.2014.00050. eCollection 2014.
Buning et al., Receptor targeting of adeno-associated virus vectors. Gene Ther. Jul. 2003;10(14):1142-51.
Calcedo et al., Worldwide epidemiology of neutralizing antibodies to adeno-associated viruses. J Infect Dis. Feb. 1, 2009;199(3):381-90.
Carter et al., Adeno-associated virus gene expression and regulation. CRC Handbook of parvoviruses. 1990:227-54.
Carter, in "Handbook of Parvoviruses", ed., P. Tijsser, CRC Press, pp. 155-168 (1990).
Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.
Cearley et al., Transduction characteristics of adeno-associated virus vectors expressing cap serotypes 7, 8, 9, and Rh10 in the mouse brain. Mol Ther. Mar. 2006;13(3):528-37. Epub Jan. 18, 2006.
Chadderton et al., Improved retinal function in a mouse model of dominant retinitis pigmentosa following AAV-delivered gene therapy. Mol Ther. Apr. 2009;17(4):593-9. Epub Jan. 27, 2009.
Chen et al., Comparative study of anti-hepatitis B virus RNA interference by double-stranded adeno-associated virus serotypes 7, 8, and 9. Mol Ther. Feb. 2009;17(2):352-9. Epub Dec. 9, 2008.
Chen et al., Molecular signatures of disease brain endothelia provide new sites for CNS-directed enzyme therapy. Nat Med. Oct. 2009;15(10):1215-8. doi: 10.1038/nm.2025. Epub Sep. 13, 2009.
Cheng et al., Development of optimized AAV3 serotype vectors: mechanism of high-efficiency transduction of human liver cancer cells. Gene Ther. Apr. 2012;19(4):375-84. doi: 10.1038/gt.2011.105. Epub Jul. 21, 2011.
Chiorini et al., Cloning and characterization of adeno-associated virus type 5. J Virol. Feb. 1999;73(2):1309-19.
Choudhury et al., Identification of Novel vectors capable of CNS transduction in adult mice after single round selection using DNA shuffled AAV capsid library. Mol Ther. May 1, 2013;21(1):S1/.
Conlon et al., Efficient hepatic delivery and expression from a recombinant adeno-associated virus 8 pseudotyped alpha1-antitrypsin vector. Mol Ther. Nov. 2005;12(5):867-75. Epub Aug. 8, 2005.
Conlon et al., Ribozyme Approaches towards Down-Regulation of Pi*Z Mutant Human a-1 Anti-Trypsin. Mol. Therapy. 2004;9:S333. Abstract 875.
Cruz et al., In vivo post-transcriptional gene silencing of alpha-1 antitrypsin by adeno-associated virus vectors expressing siRNA. Lab Invest. Sep. 2007;87(9):893-902. Epub Jun. 25, 2007.
Cruz et al., The promise of gene therapy for the treatment of alpha-1 antitrypsin deficiency. Pharmacogenomics. Sep. 2007;8(9):1191-8.
Davidson et al., Recombinant adeno-associated virus type 2, 4, and 5 vectors: transduction of variant cell types and regions in the mammalian central nervous system. Proc Natl Acad Sci U S A. Mar. 28, 2000;97(7):3428-32.
Daya et al., Gene therapy using adeno-associated virus vectors. Clin Microbiol Rev. Oct. 2008;21(4):583-93. doi: 10.1128/CMR.00008-08.
Duque et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.
Ehlert et al., Cellular toxicity following application of adeno-associated viral vector-mediated RNA interference in the nervous system. BMC Neurosci. Feb. 18, 2010;11:20.
Fechner et al., Cardiac-targeted RNA interference mediated by an AAV9 vector improves cardiac function in coxsackievirus B3 cardiomyopathy. J Mol Med (Berl). Sep. 2008;86(9):987-97. doi: 10.1007/s00109-008-0363-x. Epub Jun. 12, 2008.
Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.
Fisher et al., Transduction with recombinant adeno-associated virus for gene therapy is limited by leading-strand synthesis. J Virol. Jan. 1996;70(1):520-32.
Flotte et al., Gene therapy for alpha-1 antitrypsin deficiency. Hum Mol Genet. Apr. 15, 2011;20(R1):R87-92. doi: 10.1093/hmg/ddr156. Epub Apr. 16, 2011.
Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.
Foust et al., Intravascular AAV9 preferentially targets neonatal-neurons and adult-astrocytes. Nature Biotechnology, 27; 59-65 2009.
Foust et al., Over the barrier and through the blood: to CNS delivery we go. Cell Cycle. Dec. 15, 2009;8(24):4017-8.
Fraldi et al., Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.
Fu et al., Self-complementary adeno-associated virus serotype 2 vector: global distribution and broad dispersion of AAV-mediated transgene expression in mouse brain. Mol Ther. Dec. 2003;8(6):911-7.
Gadalla et al., Improved survival and reduced phenotypic severity following AAV9/MECP2 gene transfer to neonatal and juvenile male Mecp2 knockout mice. Mol Ther. Jan. 2013;21(1):18-30. doi:10.1038/mt.2012.200. Epub Sep. 25, 2012.
Gao et al., Adeno-associated viruses undergo substantial evolution in primates during natural infections. Proc Natl Acad Sci U S A. May 13, 2003;100(10):6081-6. Epub Apr. 25, 2003.
Gao et al., Adeno-associated virus-mediated gene transfer to non-human primate liver can elicit destructive transgene-specific T cell responses. Hum Gene Ther. Sep. 2009;20(9):930-42. doi: 10.1089/hum.2009.060.
Gao et al., Biology of AAV serotype vectors in liver-directed gene transfer to nonhuman primates. Mol Ther. Jan. 2006;13(1):77-87. Epub Oct. 10, 2005.
Gao et al., Clades of Adeno-associated viruses are widely disseminated in human tissues. J Virol. Jun. 2004;78(12):6381-8.
Gao et al., Inadvertent gene transfer of co-packaged rep and cap sequences during the production of AAV vector and its potential impact on vector performance. Molecular Therapy. May 2008;16(Suppl. 1):S105-S106. Abstract 279.
Gao et al., New recombinant serotypes of AAV vectors. Curr Gene Ther. Jun. 2005;5(3):285-97.
Gao et al., Novel adeno-associated viruses from rhesus monkeys as vectors for human gene therapy. Proc Natl Acad Sci U S A. Sep. 3, 2002;99(18):11854-9. Epub Aug. 21, 2002.
Gao et al., RAAV-mediated targeting in adult mice and its potential in generating animal models of tissue-specific somatic transgenics or knock down. Molecular Therapy. May 2008;16(1):S118-S119. Abstract 316.
GENBANK Submission; Accession No. ADZ26851; Wilson et al.; Jun. 30, 2005.
GENBANK Submission; Accession No. AF028705.1; Rutledge et al.; Jan. 12, 1998.
GENBANK Submission; NCBI, Accession No. AAB95450; Rutledge et al.; Jan. 12, 1998.
GENBANK Submission; NCBI, Accession No. AAS99264; Gao et al.; Jun. 24, 2004.
GENBANK Submission; NCBI, Accession No. ABA71701; Schmidt et al.; May 10, 2006.
GENBANK Submission; NCBI, Accession No. ACB55301; Vandenberghe et al.; Jul. 31, 2008.
GENBANK Submission; NCBI, Accession No. ACB55310; Vandenberghe et al.; Jul. 31, 2008.
GENBANK Submission; NCBI, Accession No. AY530579.10; 2004.

(56)          References Cited

OTHER PUBLICATIONS

GENBANK Submission; NCBI, Accession No. NP_049542; Xiao et al.; Mar. 11, 2010.

GENBANK Submission; NCBI, Accession No. YP_680426; Ruffing et al.; Nov. 19, 2010.

GENBANK Submission; NCBI, Accession No. Y18065; Jan. 15, 1999.

GENBANK Submission; NCBI, Accession No. AF513851; Sep. 5, 2002.

GENBANK Submission; NCBI, Accession No. AF513852; Sep. 5, 2002.

GENBANK Submission; NCBI, Accession No. AY243015; May 14, 2003.

Grimm et al., Fatality in mice due to oversaturation of cellular microRNA/short hairpin RNA pathways. Nature. May 25, 2006;441(7092):537-41.

Grimm, Small silencing RNAs: state-of-the-art. Adv Drug Deliv Rev. Jul. 25, 2009;61(9):672-703. doi: 10.1016/j.addr.2009.05.002. Epub May 7, 2009.

Hernandez et al., Latent adeno-associated virus infection elicits humoral but not cell-mediated immune responses in a nonhuman primate model. J Virol. Oct. 1999;73(10):8549-58.

Hildinger et al., Hybrid vectors based on adeno-associated virus serotypes 2 and 5 for muscle-directed gene transfer. J Virol. Jul. 2001;75(13):6199-203.

Iida et al., Systemic Delivery of Tyrosine-Mutant AAV Vectors Results in Robust Transduction of Neurons in Adult Mice. BioMed Res Int. 2013;2013.

Janson et al., Clinical protocol. Gene therapy of Canavan disease: AAV-2 vector for neurosurgical delivery of aspartoacylase gene (ASPA) to the human brain. Hum Gene Ther. Jul. 20, 2002;13(11):1391-412.

Koornneef et al., Apolipoprotein B knockdown by AAV-delivered shRNA lowers plasma cholesterol in mice. Mol Ther. Apr. 2011;19(4):731-40. doi:10.1038/mt.2011.6. Epub Feb. 8, 2011.

Kota et al., AAV8-Mediated Delivery of miR-26a inhibits cancer cell proliferation and induces tumor-specific apoptosis in a liver cancer model. Mol. Therapy. May 2009. 17(1):S300. Abstract 783.

Kotin et al., Organization of adeno-associated virus DNA in latently infected Detroit 6 cells. Virology. Jun. 1989;170(2):460-7.

Kotin et al., Site-specific integration by adeno-associated virus. Proc Natl Acad Sci U S A. Mar. 1990;87(6):2211-5.

Lawlor et al., Efficient gene delivery and selective transduction of glial cells in the mammalian brain by AAV serotypes isolated from nonhuman primates. Mol Ther. Oct. 2009;17(10):1692-702. doi:10.1038/mt.2009.170.

Lebherz et al., Gene therapy with novel adeno-associated virus vectors substantially diminishes atherosclerosis in a murine model of familial hypercholesterolemia. J Gene Med. Jun. 2004;6(6):663-72.

Leone et al., Aspartoacylase gene transfer to the mammalian central nervous system with therapeutic implications for Canavan disease. Ann Neurol. Jul. 2000;48(1):27-38. Erratum in: Ann Neurol Sep. 2000;48(3):398. Bilianuk L [corrected to Bilaniuk L].

Li et al., Efficient and Targeted Transduction of Nonhuman Primate Liver With Systemically Delivered Optimized AAV3B Vectors. Mol Ther. Dec. 2015;23(12):1867-76. doi: 10.1038/mt.2015.174. Epub Sep. 25, 2015.

Li et al., Ex vivo transduction and transplantation of bone marrow cells for liver gene delivery of alpha1-antitrypsin. Mol Ther. Aug. 2010;18(8):1553-8. Epub Jun. 15, 2010.

Li et al., Protein trans-splicing as a means for viral vector-mediated in vivo gene therapy. Hum Gene Ther. Sep. 2008;19(9):958-64. doi: 10.1089/hum.2008.009.

Lin et al., Impact of preexisting vector immunity on the efficacy of adeno-associated virus-based HIV-1 Gag vaccines. Hum Gene Ther. Jul. 2008;19(7):663-9.

Liu et al., Biological Differences in rAAV Transduction of Airway Epithelia in Humans and in Old World Non-human Primates. Mol Ther. Dec. 2007;15(12):2114-23. Epub Jul. 31, 2007.

Liu et al., Comparative biology of rAAV transduction in ferret, pig and human airway epithelia. Gene Ther. Nov. 2007;14(21):1543-8. Epub Aug. 30, 2007.

Liu et al., Species-specific differences in mouse and human airway epithelial biology of recombinant adeno-associated virus transduction. Am J Respir Cell Mol Biol. Jan. 2006;34(1):56-64. Epub Sep. 29, 2005.

Lowenstein, Crossing the rubicon. Nat Biotechnol. Jan. 2009;27(1):42-4.

Lux et al., Green fluorescent protein-tagged adeno-associated virus particles allow the study of cytosolic and nuclear trafficking. J Virol. Sep. 2005;79(18):11776-87.

Ma et al., Therapeutic silencing of miR-10b inhibits metastasis in a mouse mammary tumor model. Nat Biotechnol. Apr. 2010;28(4):341-7. doi: 10.1038/nbt.1618. Epub Mar. 28, 2010.

Maguire et al., Directed evolution of adeno-associated virus for glioma cell transduction. J Neurooncol. Feb. 2010;96(3):337-47. doi: 10.1007/s11060-009-9972-7. Epub Jul. 19, 2009.

Maguire et al., Gene therapy for the nervous system: challenges and new strategies. Neurotherapeutics. Oct. 2014;11(4):817-39. doi: 10.1007/s13311-014-0299-5.

Manfredsson et al., AAV9: a potential blood-brain barrier buster. Mol Ther. Mar. 2009;17(3):403-5.

Matalon et al., Adeno-associated virus-mediated aspartoacylase gene transfer to the brain of knockout mouse for canavan disease. Mol Ther. May 2003;7(5 Pt 1):580-7.

Mccarty et al., Adeno-associated virus terminal repeat (TR) mutant generates self-complementary vectors to overcome the rate-limiting step to transduction in vivo. Gene Ther. Dec. 2003;10(26):2112-8.

Mccarty et al., Integration of adeno-associated virus (AAV) and recombinant AAV vectors. Annu Rev Genet. 2004;38:819-45.

Mccarty et al., Self-complementary recombinant adeno-associated virus (scAAV) vectors promote efficient transduction independently of DNA synthesis. Gene Ther. Aug. 2001;8(16):1248-54.

Mccarty, Self-complementary AAV vectors; advances and applications. Mol Ther. Oct. 2008;16(10):1648-56. Epub Aug. 5, 2008.

Mccurdy et al., Sustained normalization of neurological disease after intracranial gene therapy in a feline model. Sci Transl Med. Apr. 9, 2014;6(231):231ra48. doi: 10.1126/scitranslmed.3007733.

Mietzsch et al., OneBac 2.0: Sf9 Cell Lines for Production of AAV5 Vectors with Enhanced Infectivity and Minimal Encapsidation of Foreign DNA. Hum Gene Ther. Oct. 2015;26(10):688-97. doi:10.1089/hum.2015.050. Epub Aug. 6, 2015.

Mueller et al., Development of Simultaneous Gene Augmentation and Reduction of Mutant Gene Expression with a Single Recombinant AAV for Alpha-1 Antitrypsin Disease. Molecular Therapy May 2009;17(1):S391-S392. Abstract 1030.

Mueller et al., In Vivo AAV Delivered Allele Specific shRNA for the Knockdown of Alpha-1 Antitrypsin. Molecular Therapy May 2010;18(1):S22. Abstract 53.

Mueller et al., In Vivo Allele Specific Knockdown of Mutant Alpha-1 Antitrypsin Using Recombinant AAV Delivered shRNA. Molecular Therapy May 2009;17(1):S313. Abstract 817.

Mueller et al., Using rAAV Delivered miRNAs To Knockdown Misfolded Human Alpha 1 Antitrypsin in a Transgenic Mouse Model. Molecular Therapy May 2010;18(1):S21. Abstract 51.

NCBI BLAST Protein Sequence. RID-09JSKF33114. Alignment of Seq ID Nos. 87, 179. 2016.

O'Reilly et al., RNA interference-mediated suppression and replacement of human rhodopsin in vivo. Am J Hum Genet. Jul. 2007;81(1):127-35. Epub May 23, 2007.

Passini et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.

Pertin et al., Efficacy and specificity of recombinant adeno-associated virus serotype 6 mediated gene transfer to drg neurons through different routes of delivery. Poster sessions. Eur J. Pain. 2009;13:S74. Abstract 229.

Pfeifer et al., Pharmacological potential of RNAi—focus on miRNA. Pharmacol Ther. Jun. 2010;126(3):217-27. doi: 10.1016/j.pharmthera. 2010.03.006. Epub Apr. 11, 2010.

(56)         References Cited

OTHER PUBLICATIONS

Schattgen et al., Cutting Edge: DNA in the Lung Microenvironment during Influenza Virus Infection Tempers Inflammation by Engaging the DNA Sensor AIM2. J Immunol. Jan. 1, 2016;196(1):29-33. doi:10.4049/jimmunol.1501048.

Schnepp et al., Characterization of adeno-associated virus genomes isolated from human tissues. J Virol. Dec. 2005;79(23):14793-803.

Seiler et al., Adeno-associated virus types 5 and 6 use distinct receptors for cell entry. Hum Gene Ther. Jan. 2006;17(1):10-9.

Snyder et al., Comparison of adeno-associated viral vector serotypes for spinal cord and motor neuron gene delivery. Hum Gene Ther. Sep. 2011;22(9):1129-35. doi: 10.1089/hum.2011.008. Epub Jul. 25, 2011.

Sondhi et al., Enhanced survival of the LINCL mouse following CLN2 gene transfer using the rh.10 rhesus macaque-derived adeno-associated virus vector. Mol Ther. Mar. 2007;15(3):481-91. Epub Dec. 19, 2006.

Stoica et al., Targeting Human SOD1 Using AAV mediated RNAi in a mouse model of amyotrophic lateral sclerosis. Mol ther. Jun. 2013;21(1):S149.

Storek et al., Intrathecal long-term gene expression by self-complementary adeno-associated virus type 1 suitable for chronic pain studies in rats. Mol Pain. Jan. 30, 2006;2:4.

Tarasov et al., Differential Regulation of microRNAs by p53 Revealed by Massively Parallel Sequencing: miR-34a is a p53 Target That Induces Apoptosis and G1-arrest. Cell Cycle. Jul. 1, 2007;6(13):1586-93. Epub May 11, 2007.

Tenenbaum et al., Recombinant AAV-mediated gene delivery to the central nervous system. J Gene Med. Feb. 2004;6 Suppl 1:S212-22.

Tokumaru et al., let-7 regulates Dicer expression and constitutes a negative feedback loop. Carcinogenesis. Nov. 2008;29(11):2073-7. doi: 10.1093/carcin/bgn187. Epub Aug. 11, 2008.

Tomar et al., Use of adeno-associated viral vector for delivery of small interfering RNA. Oncogene. Aug. 28, 2003;22(36):5712-5.

Towne et al., Systemic AAV6 delivery mediating RNA interference against SOD1: neuromuscular transduction does not alter disease progression in fALS mice. Mol Ther. Jun. 2008;16(6):1018-25. doi:10.1038/mt.2008.73. Epub Apr. 15, 2008.

Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.

Vandenberghe et al., Heparin binding directs activation of T cells against adeno-associated virus serotype 2 capsid. Nat Med. Aug. 2006;12(8):967-71. Epub Jul. 16, 2006.

Vandenberghe et al., Tailoring the AAV vector capsid for gene therapy. Gene Ther. Mar. 2009;16(3):311-9. Epub Dec. 4, 2008.

Vandendriessche et al., Efficacy and safety of adeno-associated viral vectors based on serotype 8 and 9 vs. lentiviral vectors for hemophilia B gene therapy. J Thromb Haemost. Jan. 2007;5(1):16-24. Epub Sep. 26, 2006.

Virella-Lowell et al., Enhancing rAAV vector expression in the lung. J Gene Med. Jul. 2005;7(7):842-50.

Vulchanova et al., Differential adeno-associated virus mediated gene transfer to sensory neurons following intrathecal delivery by direct lumbar puncture. Mol Pain. May 28, 2010;6:31. doi: 10.1186/1744-8069-6-31.

Wang et al., Rescue and replication of adeno-associated virus type 2 as well as vector DNA sequences from recombinant plasmids containing deletions in the viral inverted terminal repeats: selective encapsidation of viral genomes in progeny virions. J Virol. Mar. 1996;70(3):1668-77.

Wang et al., Somatically Repairing Compound Heterozygous Recessive Mutations by Chromosomal Cut-and-Paste for in Vivo Gene Therapy. May 2016. 24(1):S289. Abstract 733.

Wang et al., Sustained correction of disease in naive and AAV2-pretreated hemophilia B dogs: AAV2/8-mediated, liver-directed gene therapy. Blood. Apr. 15, 2005;105(8):3079-86. Epub Jan. 6, 2005.

Wang et al., The design of vectors for RNAi delivery system. Curr Pharm Des. 2008;14(13):1327-40.

Wang et al., The potential of adeno-associated viral vectors for gene delivery to muscle tissue. Expert Opin Drug Deliv. Mar. 2014;11(3):345-64. doi: 10.1517/17425247.2014.871258. Epub Jan. 3, 2014.

Wang et al., Widespread spinal cord transduction by intrathecal injection of rAAV delivers efficacious RNAi therapy for amyotrophic lateral sclerosis. Hum Mol Genet. Feb. 1, 2014;23(3):668-81. doi: 10.1093/hmg/ddt454. Epub Sep. 18, 2013.

Weismann et al., Systemic AAV9 gene transfer in adult GM1 gangliosidosis mice reduces lysosomal storage in CNS and extends lifespan. Hum Mol Genet. Aug. 1, 2015;24(15):4353-64. doi: 10.1093/hmg/ddv168. Epub May 10, 2015.

Weismann, Approaches and Considerations Towards a Safe and Effective Adena-Associated Virus Mediated Therapeutic Intervention for GM 1-Gangliosidosis: A Dissertation. University Massachusetts Medical School. Aug. 5, 2014.

Wu et al., Alpha2,3 and alpha2,6 N-linked sialic acids facilitate efficient binding and transduction by adeno-associated virus types 1 and 6. J Virol. Sep. 2006;80(18):9093-103.

Xie et al., Isolation of transcriptionally active novel AAV capsid sequences from chimpanzee tissues for vector development. Meeting Abstract: 12th Annual Meeting of the American Society of Gene Therapy. May 1, 2009. Abstract 91.

Xie et al., 676. DNA Sequences Encoding shRNAs Can Replace Mutant ITR in scAAV Genome for Efficient Replication and Packaging and Transcribe shRNAs by pol III Promoter Activity of wt ITR for Efficient Gene Silencing Mol Therapy. May 2015;23(1):S269.

Xie et al., Characterization of positioning effect of pol III-shRNA transcription unit in scAAV vector genome on the packaging efficiency and functionality of shRNA silencing. Molecular Therapy. May 2010;18(1): S262. Abstract 671.

Xie et al., MicroRNA regulated tissue specific transduction by rAAV vector. Molecular Therapy. May 2009;17(1): S279. Abstract 732.

Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.

Xie et al., rAAV-mediated delivery of micro RNA scavengers leads to efficient and stable knock-down of cognate micro RNAs, upregulation of their natural target genes and phenotypic changes in mice. Molecular Therapy. May 2010;18(1): S140. Abstract 362.

Xie et al., Short DNA Hairpins Compromise Recombinant Adeno-Associated Virus Genome Homogeneity. Mol Ther. Jun. 7, 2017;25(6):1363-1374. doi: 10.1016/j.ymthe.2017.03.028. Epub Apr. 24, 2017.

Xu et al., Delivery of MDR1 small interfering RNA by self-complementary recombinant adeno-associated virus vector. Mol Ther. Apr. 2005;11(4):523-30.

Yan et al., Unique biologic properties of recombinant AAV1 transduction in polarized human airway epithelia. J Biol Chem. Oct. 6, 2006;281(40):29684-92. Epub Aug. 9, 2006.

Zabner et al., Adeno-associated virus type 5 (AAV5) but not AAV2 binds to the apical surfaces of airway epithelia and facilitates gene transfer. J Virol. Apr. 2000;74(8):3852-8.

Zhang et al., Characterization of 12 AAV vectors for intravascular delivery to target CNS and detarget non-CNS tissues by mirna regulation: implications in treatment of canavan disease. Molecular Therapy. May 2010;18(1): S174. Abstract 450.

Zhong et al., Chimpanzee-derived novel natural variants of aav9: vector development and interrogation of correlations between capsid structure and vector biology. Molecular Therapy. May 2010;18(1): S24. Abstract 58.

Zincarelli et al., Analysis of AAV serotypes 1-9 mediated gene expression and tropism in mice after systemic injection. Mol Ther. Jun. 2008;16(6):1073-80. doi: 10.1038/mt.2008.76. Epub Apr. 15, 2008.

Zolotukhin et al., Production and purification of serotype 1, 2, and 5 recombinant adeno-associated viral vectors. Methods. Oct. 2002;28(2):158-67.

Hacker et al., Adeno-associated virus serotypes 1 to 5 mediated tumor cell directed gene transfer and improvement of transduction efficiency. J Gene Med. Nov. 2005;7(11):1429-38. doi: 10.1002/jgm.782.

(56) References Cited

OTHER PUBLICATIONS

Lisowski et al., Adeno-associated virus serotypes for gene therapeutics. Curr Opin Pharmacol. Oct. 2015;24:59-67. doi: 10.1016/j.coph.2015.07.006. Epub Aug. 25, 2015.

Van Vliet et al., The role of the adeno-associated virus capsid in gene transfer. Methods Mol Biol. 2008;437:51-91. doi: 10.1007/978-1-59745-210-6_2.

Messina et al., Adeno-associated viral vectors based on serotype 3b use components of the fibroblast growth factor receptor signaling complex for efficient transduction. Hum Gene Ther. Oct. 2012;23(10):1031-42. doi: 10.1089/hum.2012.066. Epub Aug. 27, 2012.

Isayeva et al., Effects of sustained antiangiogenic therapy in multistage prostate cancer in TRAMP model. Cancer Res. Jun. 15, 2007;67(12):5789-97. doi: 10.1158/0008-5472.CAN-06-3637.

Grimm et al., Helper virus-free, optically controllable, and two-plasmid-based production of adeno-associated virus vectors of serotypes 1 to 6. Mol Ther. Jun. 2003;7(6):839-50. doi: 10.1016/s1525-0016(03)00095-9.

Rutledge et al., Infectious clones and vectors derived from adeno-associated virus (AAV) serotypes other than AAV type 2. J Virol. Jan. 1998;72(1):309-19. doi: 10.1128/JVI.72.1.309-319.1998.

FIG. 6B

BS: Binding site
PSL: irrelevant plasmids

Cell viability Assay

Mock miR34a

Wound Healing Assay 0h                    24h

PROSTATE TARGETING ADENO-ASSOCIATED VIRUS SEROTYPE VECTORS

RELATED APPLICATIONS

This application is a continuation under 35 U.S.C. § 120 of U.S. application Ser. No. 15/769,953, filed Apr. 20, 2018, which is a national stage application of PCT/US2016/058185, filed Oct. 21, 2016, which claims the benefit of priority under 35 U.S.C. § 119 (e) of U.S. Provisional Application Ser. No. 62/245,027, filed Oct. 22, 2015, and U.S. Provisional Application Ser. No. 62/322,285, filed Apr. 14, 2016, the entire contents of each application are incorporated herein by reference.

BACKGROUND

The prostate is an exocrine gland that is crucial to constituting the male reproductive system, and the functions of prostate are similar in the majority of mammals despite anatomical differences. Three types of prostate diseases are the major threats for the health of prostate, i.e., prostatitis, benign prostate hyperplasia (BPH) and prostate cancer. Together, these prostate diseases are severely compromising the life quality and life span of males, especially for the aged male population. For example, BPH is one of the top ten most costly diseases among male populations over 50-year old in the USA, and prostate cancer is the second most diagnosed malignancy and the sixth leading cause for mortality of all cancers in males worldwide.

To date, many efforts have been made to prevent or to treat prostate diseases, including surgery, medication, and radiotherapy. Nevertheless, highly effective clinical interventions for a variety of prostate diseases are still lacking. For example, although the early stage of prostate cancer can be prevented with hormonal therapy, most hormone-dependent prostate cancers will eventually develop into castration-resistant prostate cancer (CRPC). So far, no effective treatment exists for CRPC. As the genetic basis of prostate diseases was gradually unraveled during the past decades, gene therapy was explored as a therapeutic strategy for prostate diseases, and researchers have demonstrated the feasibility of several gene therapy approaches to treating BPH and prostate cancer in mice using various types of viral gene delivery vectors. However, many viral vectors, such as adenovirus, lentivirus and retrovirus, can cause insertional genotoxicity and/or immunotoxicity, which greatly limits their clinical use.

SUMMARY

Adeno-associated virus (AAV) is a single-stranded DNA virus, and recombinant AAV (rAAV) vectors possess many advantages in gene therapy applications, including low immunogenicity and genotoxicity, broad tissue tropism and high transduction efficiency in vice, and long-term transgene expression. Aspects of the invention are related to the discovery that rAAV vectors comprising capsid proteins having a certain serotype, including, but not limited to, AAV5, AAV6.2, AAV7, AAV8, AAV9, AAVrh.10, mediate delivery of transgenes to prostate tissue more efficiently than other vectors (e.g., rAAV vectors comprising other capsid protein serotypes).

Accordingly in some aspects, the disclosure provides a method for delivering a transgene to prostate tissue, the method comprising: administering to prostate tissue of a subject an effective amount of rAAV, wherein the rAAV comprises (i) a capsid protein having a serotype selected from the group consisting of AAV5, AAV6, AAV6.2, AAV7, AAV8, AAV9, and AAVrh.10, and (ii) a nucleic acid comprising a promoter operably linked to a transgene.

In some aspects, the disclosure provides a method for treating a prostate disease, the method comprising: administering to a subject having or suspected of having a prostate disease an effective amount of rAAV, wherein the rAAV comprises (i) a capsid protein having a serotype selected from the group consisting of AAV5, AAV6.2, AAV7, AAV8, AAV9, and AAVrh.10, and (ii) a nucleic acid comprising a promoter operably linked to a transgene.

In some embodiments, the capsid protein comprises an amino acid sequence that is at least 70%, at least 80%, at least 90%, at least 95%, or at least 99% identical to any one of SEQ ID NO: 1-7. In some embodiments, the capsid protein comprises an amino acid sequence as set forth in SEQ ID NO: 3 or 4. In some embodiments, the capsid protein is AAV6.2 capsid protein (SEQ ID NO: 3) or AAV7 capsid protein (SEQ ID NO: 4).

In some embodiments, the transgene encodes a gene associated with a prostate disease. In some embodiments, the prostate disease is selected from prostatitis, prostate cancer and benign prostate hyperplasia (BPH). In some embodiments, the gene encodes a tumor suppressor molecule (e.g., a tumor suppressor protein or a miRNA that regulates tumor suppression). In some embodiments, the gene encodes BCL2, PTEN, SLC39A1, BRCA1, BRCA2, HPC1, RUNX2, CLCA2, YAP1, MASPIN, LL37, CDKN1B, AR, NKX3.1, CASP9, FKHR, GSK3, MDM2, ERK1/2, PSA, CCND1, ALDOA, Sox4, CD44, and miR34a.

In some aspects, the disclosure is based on the discovery that miR34a expression is downregulated in prostate cancer cells. In some embodiments, overexpression of miR34a in prostate cancer cells results in decreased cancer cell viability and migration. Accordingly, in some aspects, the disclosure provides a method for treating a prostate disease, the method comprising: administering to a subject having or suspected of having a prostate disease an effective amount of a nucleic acid comprising a promoter operably linked to a transgene, wherein the transgene encodes miR34a. In some embodiments, the transgene comprises or consists of a nucleic acid having a sequence as set forth in SEQ ID NO: 15. In some embodiments, the nucleic acid comprises or consists of a nucleic acid having a sequence as set forth in SEQ ID NO: 16.

In some embodiments, the administration occurs by injection. In some embodiments, the injection is not intraperitoneal injection (i.p.). In some embodiments, the injection is intraprostate injection.

In some embodiments, the administration results in transduction of a prostate cell type selected from the group consisting of luminal prostate cells, basal prostate cells, and stromal prostate cells. In some embodiments, the administration results in transduction of at least two of the following prostate cell types: luminal prostate cells, basal prostate cells, and stromal prostate cells.

In some embodiments, the rAAV further comprises two AAV inverted terminal repeats (ITRs), wherein the ITRs flank the transgene. In some embodiments, the AAV ITRs are ITRs of one or more serotypes selected from: AAV2, AAV3, AAV4, AAV5, and AAV6.

In some embodiments, the subject is a mammal, optionally a human.

Each of the limitations of the disclosure can encompass various embodiments of the disclosure. It is, therefore, anticipated that each of the limitations of the disclosure involving any one element or combinations of elements can be included in each aspect of the disclosure. This disclosure is not limited in its application to the details of construction and the arrangement of components set forth in the following description or illustrated in the drawings. The disclosure is capable of other embodiments and of being practiced or of being carried out in various ways.

BRIEF DESCRIPTION OF DRAWINGS

FIG. 2A shows representative fluorescence images of anterior prostate (AP) cryo-sections showing the merge of EGFP native fluorescence and nuclear staining by DAN following injections of each of 12 rAAV serotypes or PBS. Squared regions indicate the locations of high magnification images shown in (FIG. 2B). Scale bars represent 100 microns. FIG. 2B shows high magnification images of AP cryo-sections following PBS injection or transduction with rAAV6.2 and 7. Scale bars represent 25 microns.

FIG. 3A shows representative fluorescence images of dorsal lateral prostate (DLP) cryo-sections showing the merge of EGFP native fluorescence and nuclear staining by DAPI following injections of each of 12 rAAV serotypes or PBS. Squared regions indicate the locations of high magnification images shown in (FIG. 3B). Scale bars represent 100 microns. FIG. 3B shows high magnification images of DLP cryo-sections following PBS injection or transduction with rAAV6.2 and 7. Scale bars represent 25 microns.

FIG. 4A shows quantification of transduction efficiency in AP (gray bars) and DLP (black bars) following intraprostate injection with rAAV vectors of different serotypes expressing EGFP. EGFP fluorescence intensity of cryo-sections is presented in arbitrary units (a.u.). FIG. 4B shows biodistribution of rAAV genomes in AP (gray bars) and DLP (black bars) following intraprostate injection of rAAV6.2 and rAAV7. Data are presented as rAAV genuine copies per diploid genome.

FIGS. 6A-6B show rAAV6.2 and 7 could transduce the majority of major prostatic cell types following intraprostate injection. FIG. 6A shows representative images of immunofluorescence staining of prostate luminal cells (top panels), basal cells (middle panels) and stromal cells (bottom panels), marked by K8, K5 and α-actin staining, respectively. Nuclear staining by DAPI, native EGFP fluorescence images and merged images from the same sections are also shown. Arrows indicate representative co-localization of EGFP signal and cell type marker signal. FIG. 6B shows quantification of the percentage of EGFP-positive cells of each cell type.

Figure 7A:
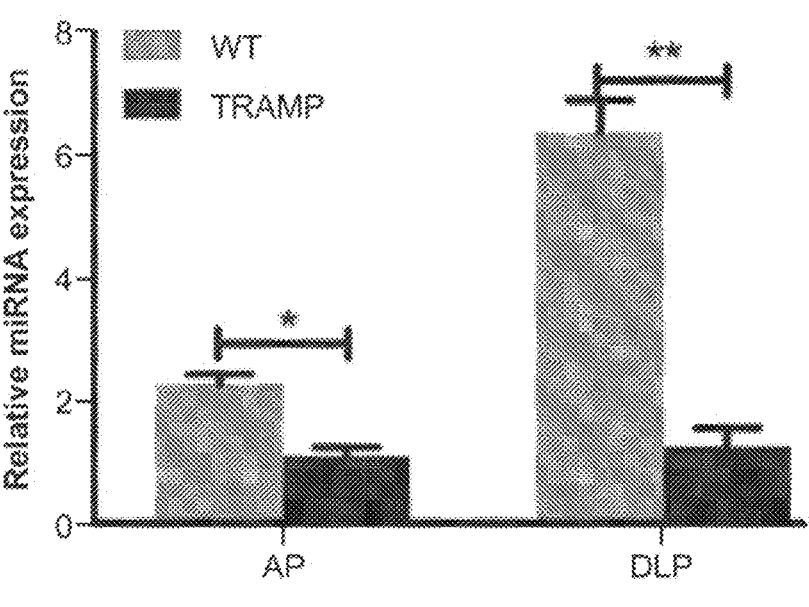
Figure 7B:
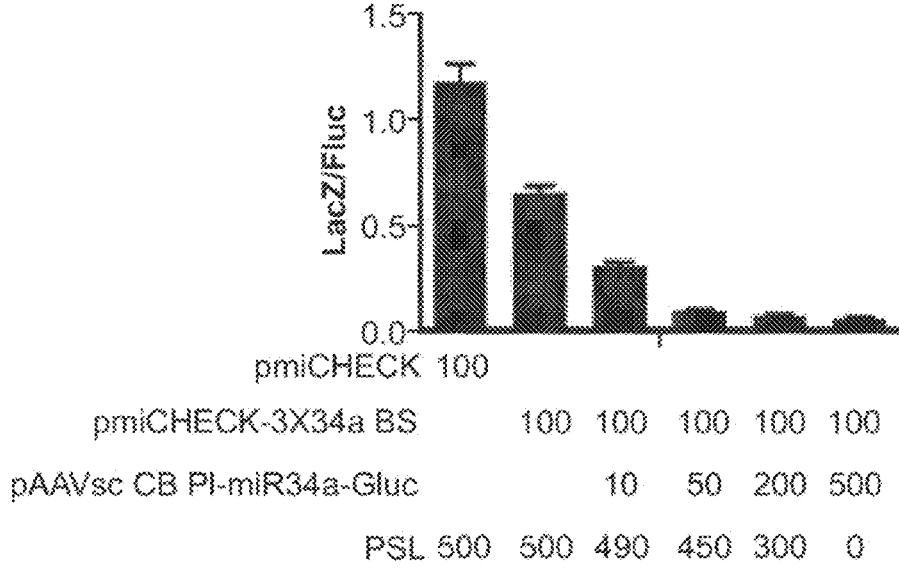

FIGS. 7A-7B show data relating to miR34a expression in prostate cancer. FIG. 7A shows qPCR data indicating that miR34a is significantly downregulated in the prostate of TRAMP mice compared to wild type (WT) mice. FIG. 7B shows a luciferase assay demonstrating rAAV-miR34 pAAVsc-CB PI-miR34a-Gluc) successfully downregulates reporter gene (LacZ/Fluc) expression in vitro.

Figure 8A:
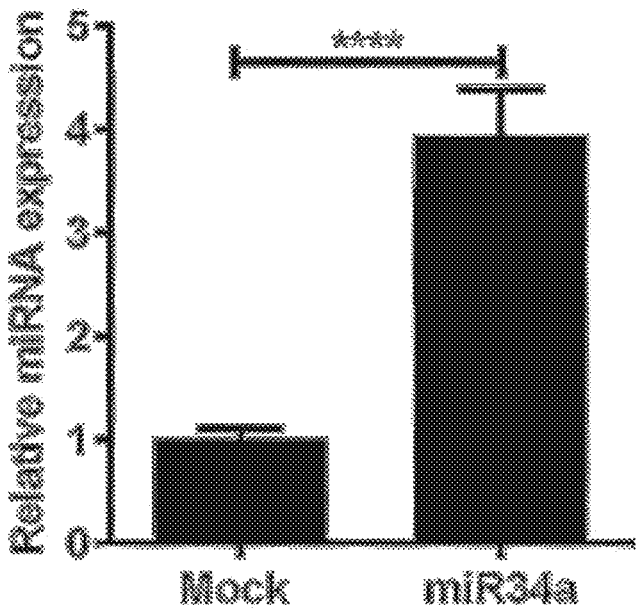
Figure 8B:
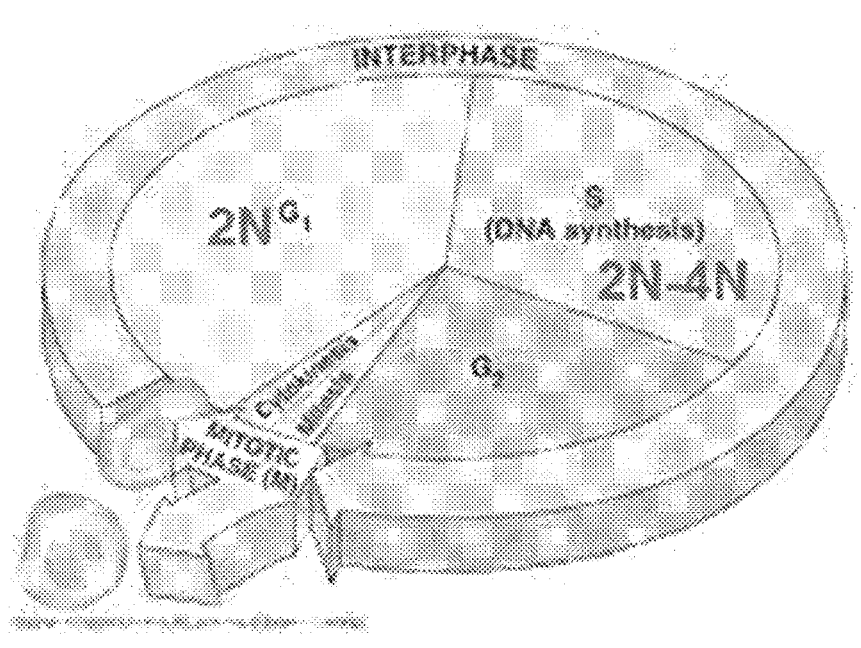
Figures 8C, 8D:
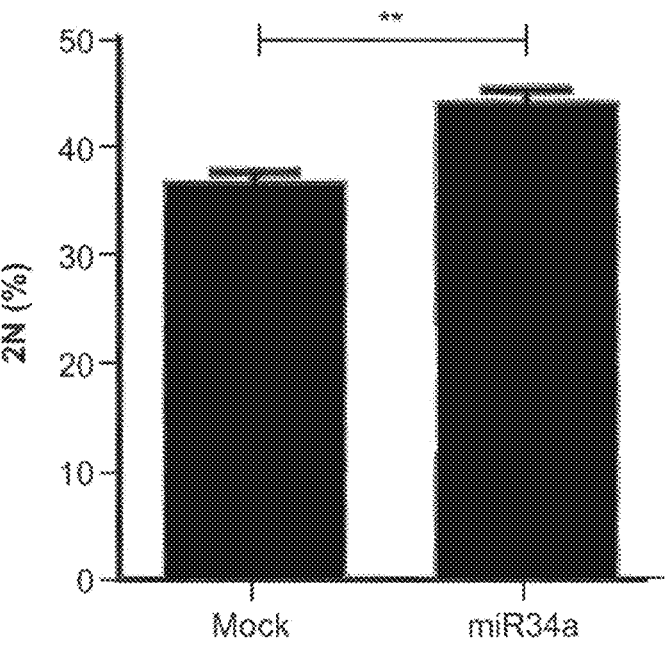
Figure 8E:
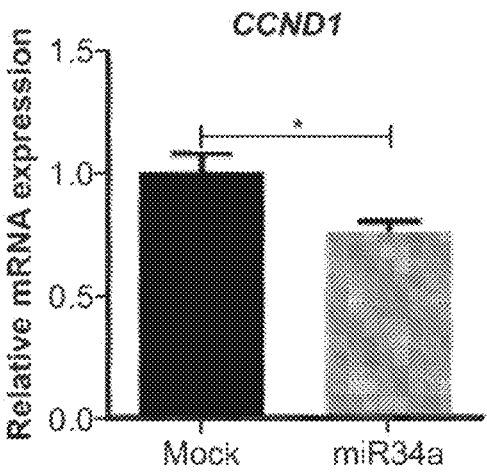
Figure 8E:
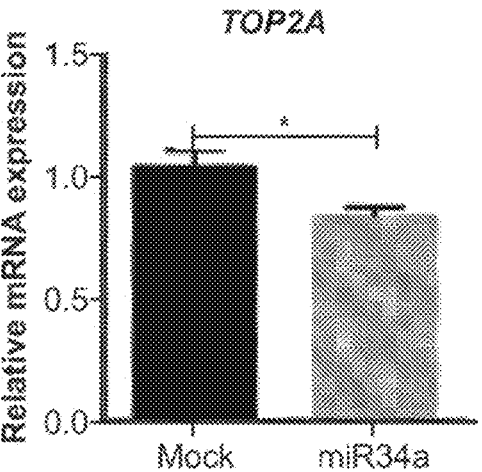
Figure 8E:
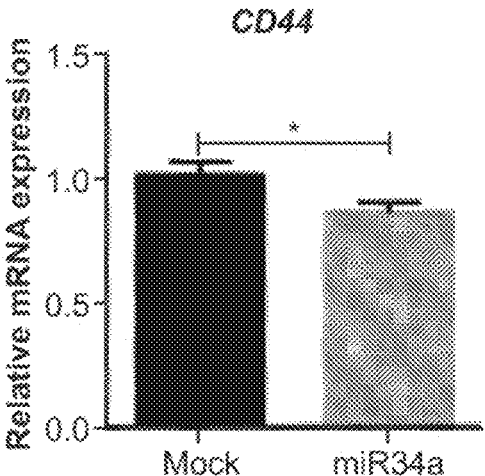

FIGS. 8A-8E show miR34a overexpression inhibits prostate cancer cell cycle. FIG. 14A shows qPCR data demonstrating relative expression level of miR34a in control (mock) and miR34a-treated cells 48 hours post-transfection. FIG. 8B shows a schematic diagram of a prostate cancer cell cycle, highlighting the $G_1$ (2N) and S (2N-4N) phases. FIG. 8C shows transfection with miR34a results in a significant increase in 2N cells compared to mock transfected cells. FIG. 8D shows transfection with miR34a results in a significant decrease in 2N-4N cells compared to mock transfected cells. FIG. 8E shows miR34a overexpression decreases target gene expression (CCND1, TOP2A, and CD44) in vitro.

Figure 9A:
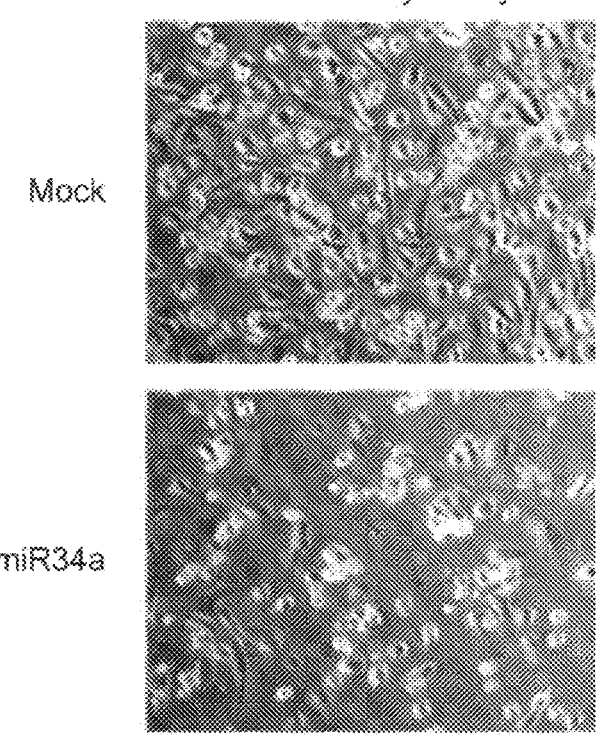
Figure 9B:
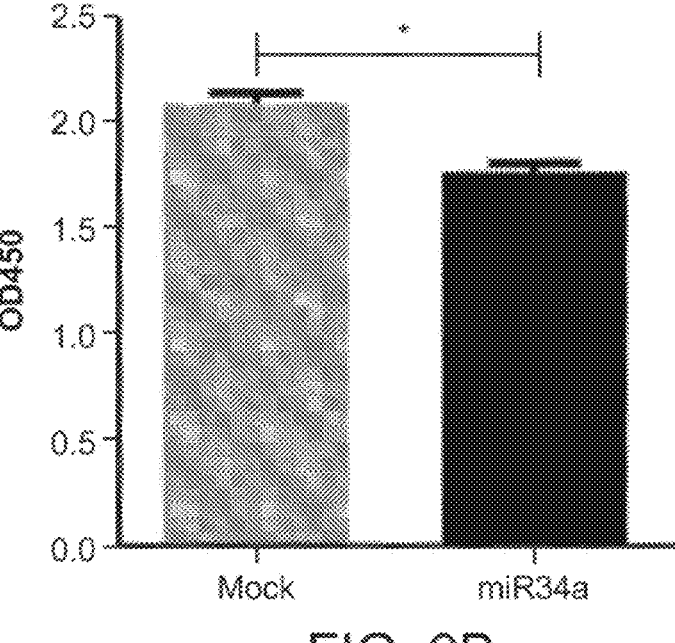
Figure 9C:
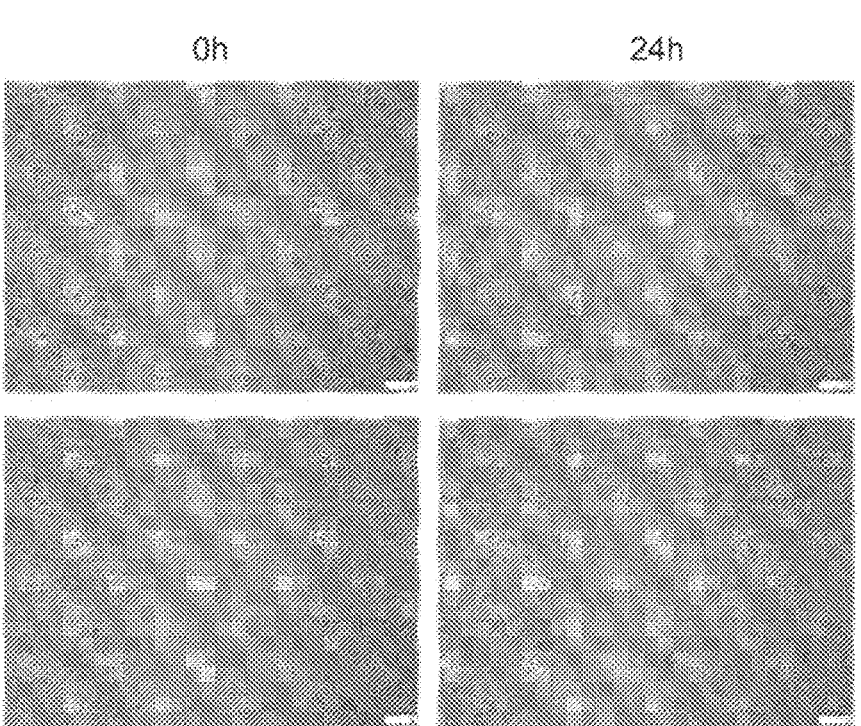
Figure 9D:
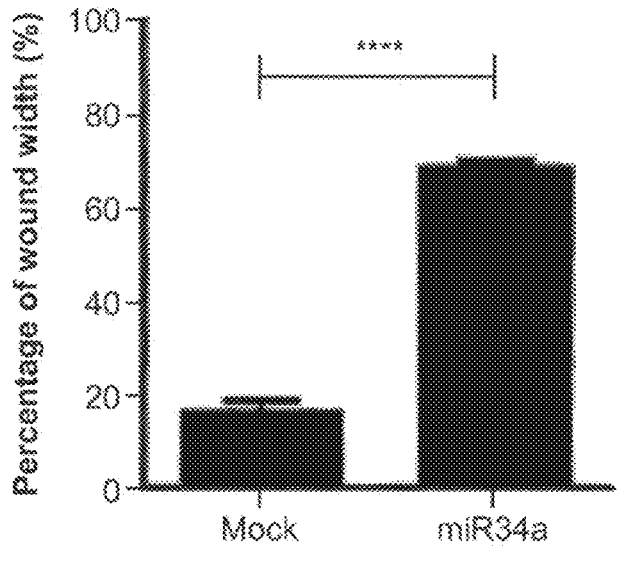

FIGS. 9A-9D show miR34a overexpression reduces cell viability and inhibits migration of PC3 prostate cancer cells. FIG. 9A shows overexpression of miR34a results in a decrease in cell viability of miR34a treated PC3 cells compared to control (Mock) PC3 cells. FIG. 9B shows a significant decrease in 013450 of miR34a-treated PC3 cells compared to control (Mock) PC3 cells. FIG. 9C shows overexpression of miR34a results in reduced PC3 cell migration compared to untreated cells, as measured by a wound healing assay. FIG. 9D shows overexpression of miR34a results in a significant increase in wound width, indicating a reduction in cell migration, compared to control (Mock) cells.

Figure 10A:
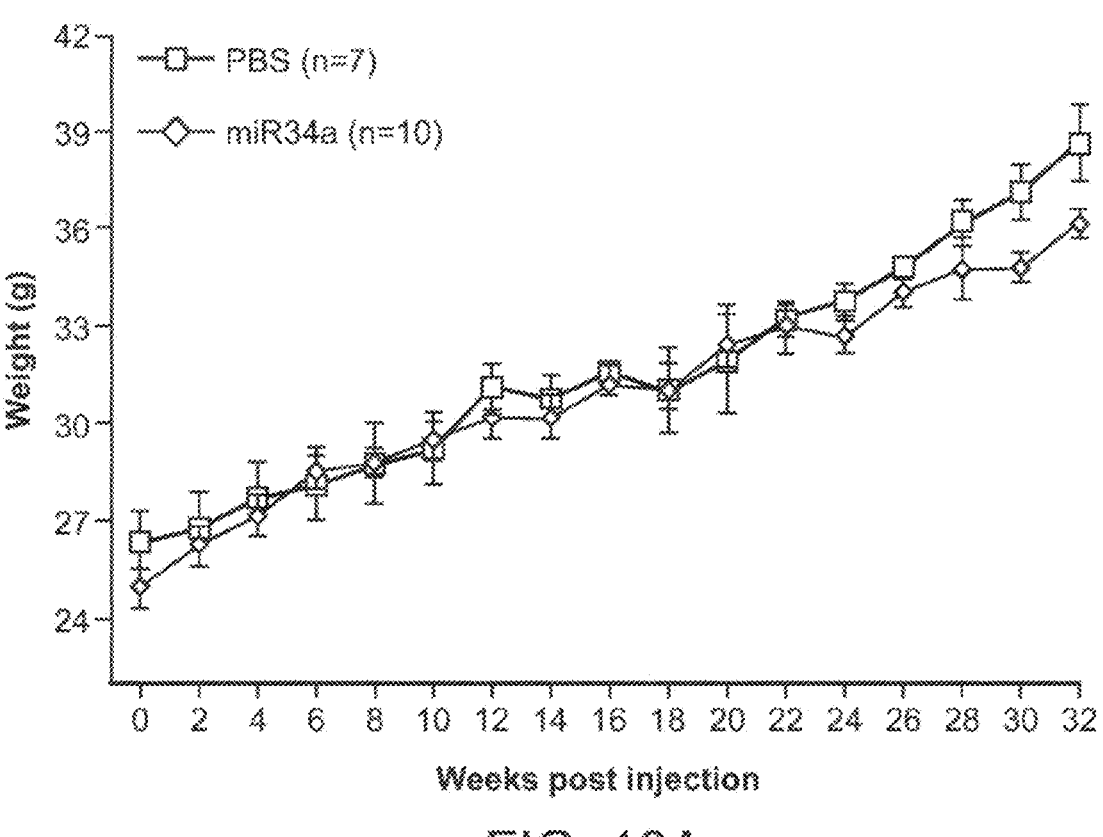
Figure 10B:
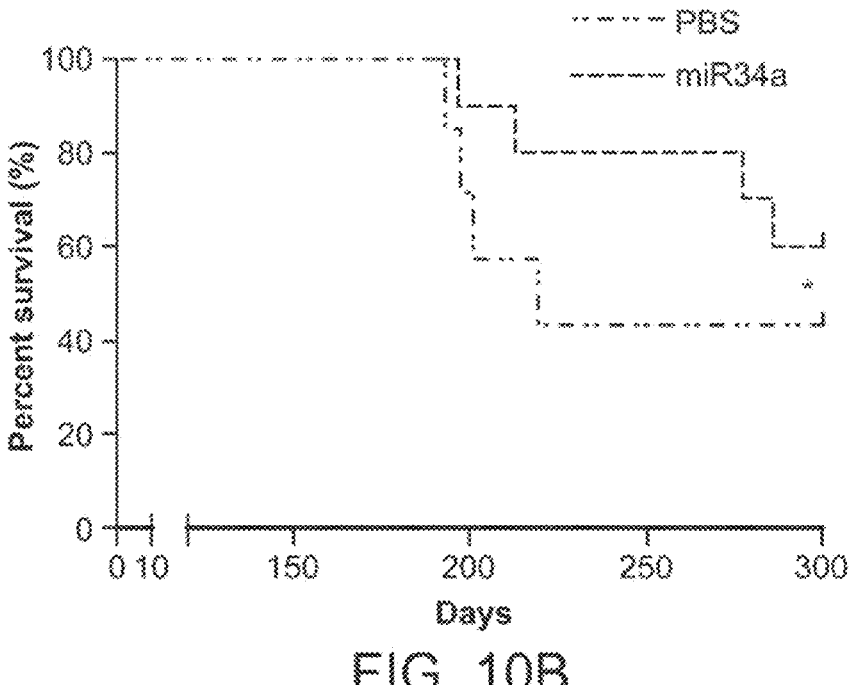

FIGS. 10A-10B show miR34a increases the survival rate of TRAMP mice. FIG. 10A shows 2-month old TRAMP mice intraprostatically injected with rAAV7-miR34a ($4 \times 10^{11}$ GC/mouse) have a significantly lower body weight (e.g., less tumor growth) than PBS-treated control mice. FIG. 10B shows 2-month old TRAMP mice intraprostatically injected with rAAV7-miR34a ($4 \times 10^{11}$ GC/mouse) have a significantly improved survival rates (measured by percent survival) compared to PBS-treated control mice.

Figure 11:
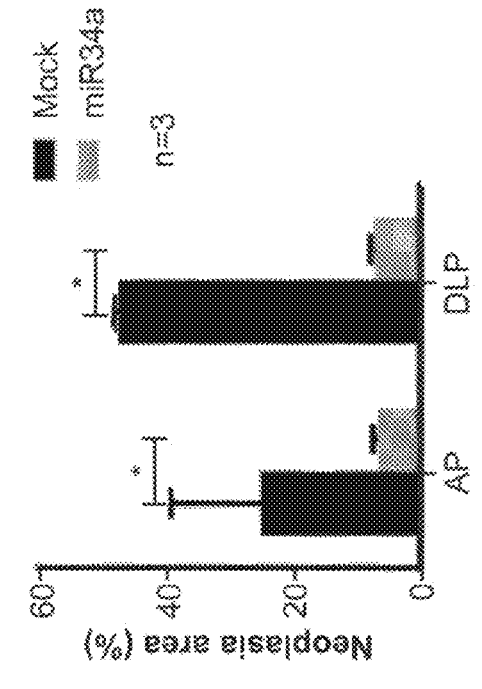
Figure 11:
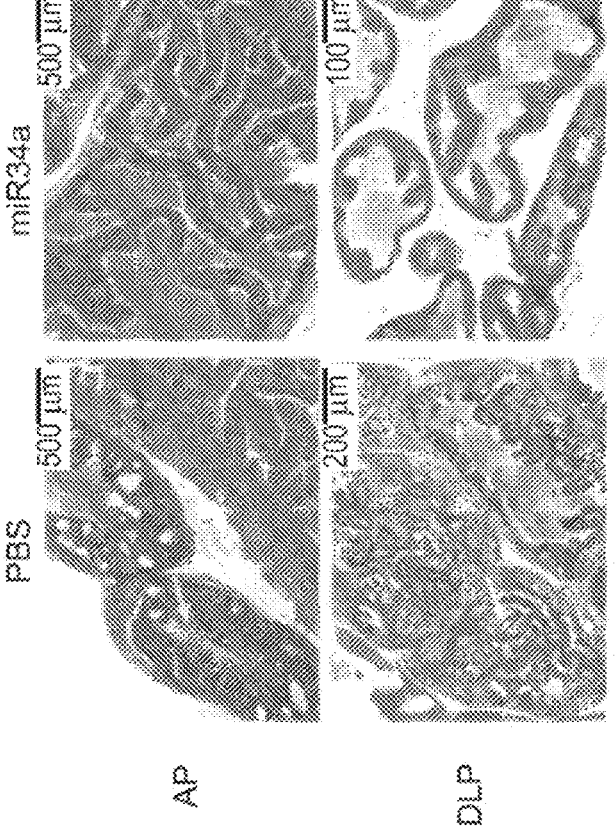

FIG. 11 shows miR34a overexpression ameliorates prostate cancer progression in vivo. 2-month old TRAMP mice were intraprostatically injected with rAAV7-miR34a ($4 \times 10^{11}$ GC/mouse). miR34a-treated mice show a decrease in prostate tissue pathology in both the anterior prostate (AP) and the dorsal lateral prostate (DLP) compared to PBS-injected control mice. Treatment with miR34a also results in significantly lower neoplasia area compared to control mice.

Figure 12A:
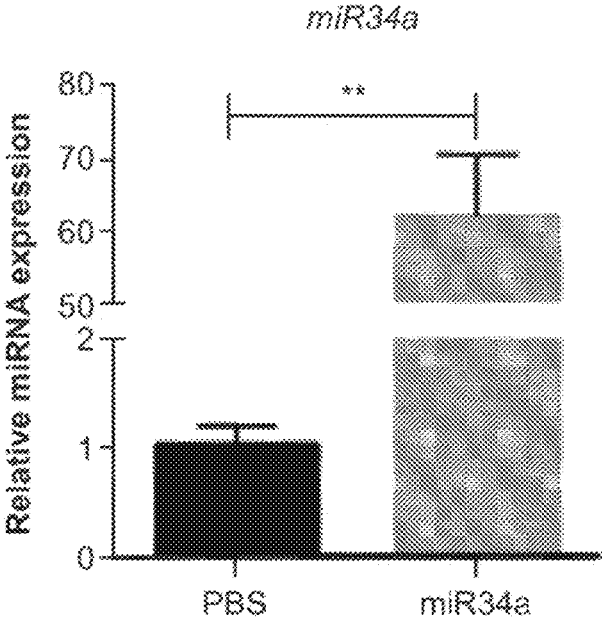
Figure 12B:
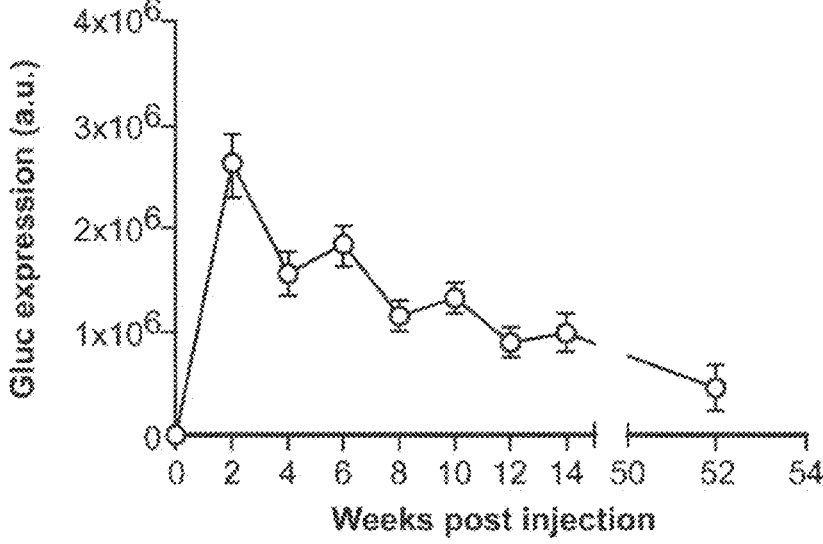
Figure 12C:
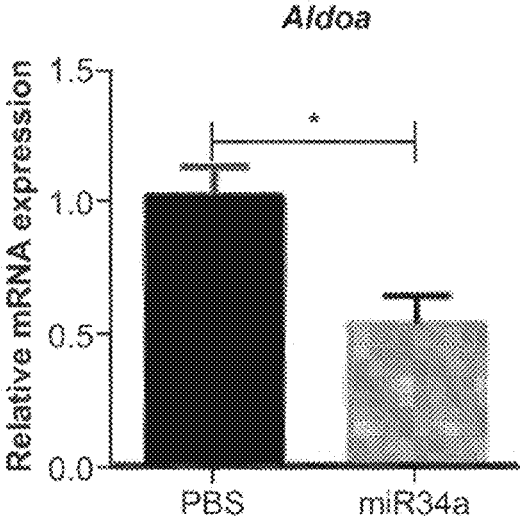
Figure 12C:
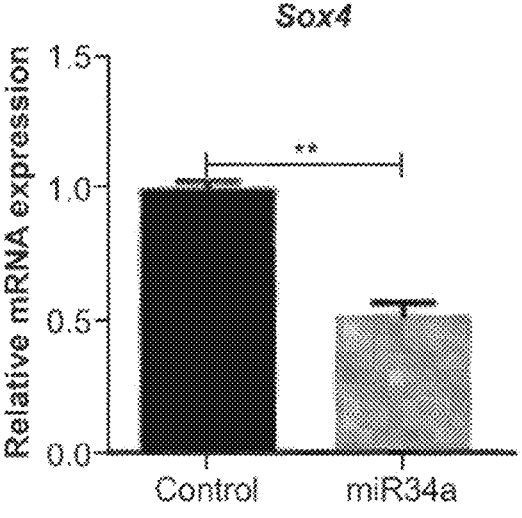

FIGS. 12A-12C show miRNA and target expression in mouse prostate 3 weeks post-intraprostatic injection ($4 \times 10^{11}$ GC/mouse). FIG. 12A shows relative expression of miR34a is significantly increased in miR34a-treated mouse prostate compared to PBS-injected control mice. FIG. 12B shows reporter gene (Gluc) expression persists up to 52 weeks post-intraprostatic injection of rAAV-miR34a-Gluc. FIG. 12C shows mice treated with miR34a show significant decreases in ALDOA and Sox4 expression compared to PBS-injected control mice 3 weeks post-injection.

Figure 13:
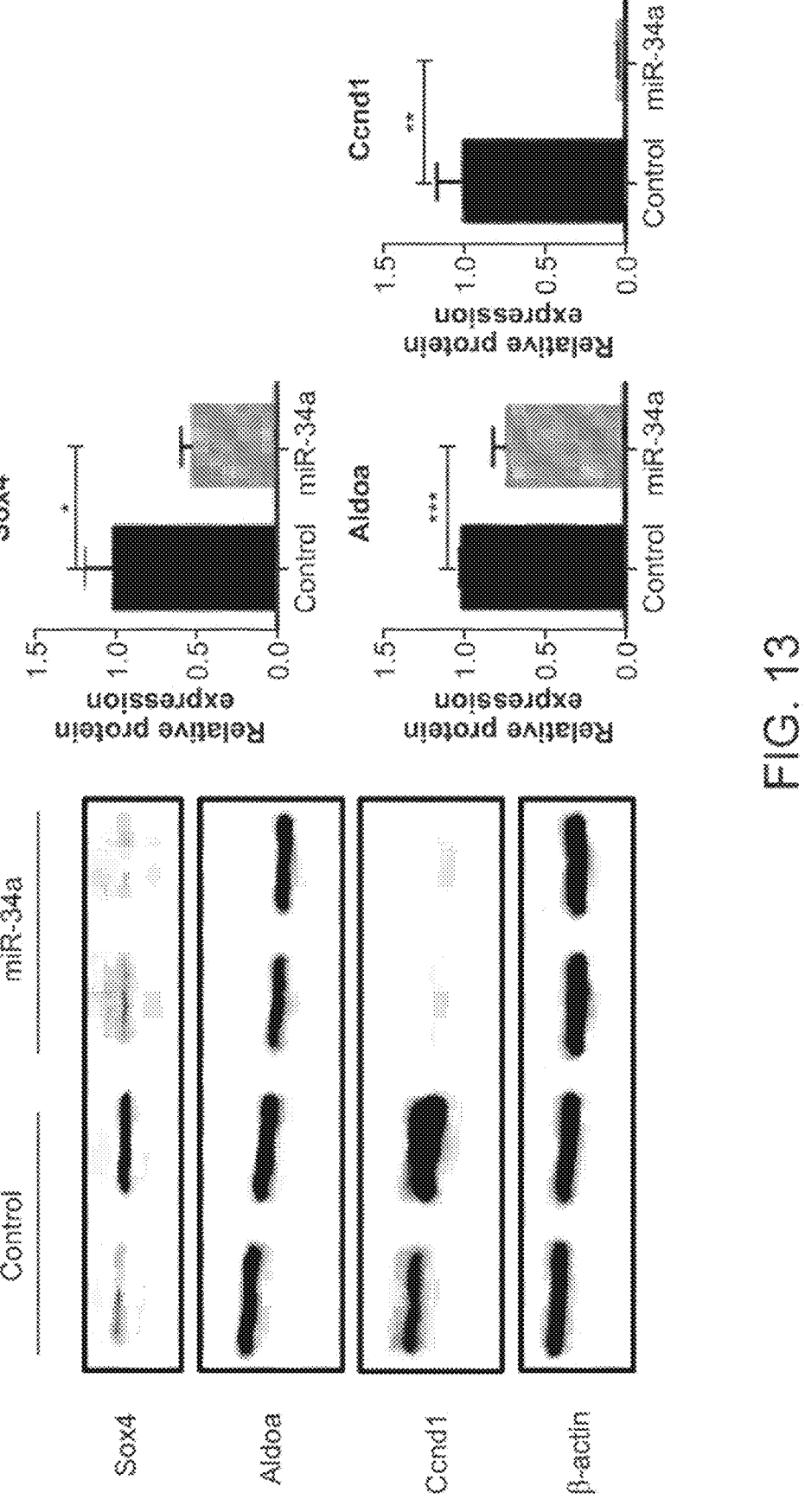

FIG. 13 shows Western blots demonstrating that miR34a overexpression downregulates Aldoa, Ccnd1, and Sox4 expression in mouse prostate compared to control mouse prostate.

DETAILED DESCRIPTION

The disclosure relates in some aspects to compositions and methods for tissue-specific delivery of a transgene by a recombinant adeno-associated virus (rAAV). The invention relates, in part, to the discovery that rAAV vectors comprising a capsid protein(s) having a certain serotype (e.g., AAV5, AAV6.2, AAV7, AAV8, AAV9, and AAVrh.10) mediate delivery of transgenes to prostate tissue more efficiently than rAAV vectors comprising other capsid protein serotypes. Methods and Compositions for AAV-Mediated Delivery of a Transgene to Prostate Tissue Methods for delivering a transgene to prostate tissue in a subject are provided herein. The methods typically involve administering to a subject an effective amount of a rAAV comprising a nucleic acid for expressing a transgene in the subject. An "effective amount" of a rAAV is an amount sufficient to infect a sufficient number of cells of a target tissue in a subject. In some embodiments, a target tissue is prostate tissue. An effective amount of a rAAV may be an amount sufficient to have a therapeutic benefit in a subject, e.g., to extend the lifespan of a subject, to improve in the subject one or more symptoms of disease, e.g., a symptom of prostate disease (e.g., prostatitis. BPH, prostate cancer, etc.). In some cases, an effective amount of a rAAV may be an amount sufficient to produce a stable somatic transgenic animal model. The effective amount will depend on a variety of factors such as, for example, the species, age, weight, health of the subject, and the prostate tissue to be targeted, and may thus vary among subject and tissue.

An effective amount may also depend on the rAAV used. The invention is based, in part on the recognition that rAAV comprising capsid proteins having a particular serotype (e.g., AAV5, AAV6.2, AAV7, AAV8, AAV9, and AAVrh.10) mediate more efficient transduction of prostate tissue that rAAV comprising capsid proteins having a different serotype. Thus in some embodiments, the rAAV comprises a capsid protein of an AAV serotype selected from the group consisting of: AAV5, AAV6.2, AAV7, AAV8, AAV9, and AAVrh.10 (SEQ ID NO: 1 to 6). In some embodiments, the rAAV comprises a capsid protein of AAV6.2 serotype (SEQ ID NO: 3) or AAV7 serotype (SEQ ID NO: 4). In some embodiments, the capsid protein comprises an amino acid sequence that is at least 70%, at least 80%, at least 90%, at least 95%, or at least 99% identical to any one of SEQ ID NO: 1-7. In some embodiments, the capsid protein is AAV6.2 capsid protein (SEQ ID NO: 3) or AAV7 capsid protein (SEQ ID NO: 4).

In certain embodiments, the effective amount of rAAV is $10^{10}$, $10^{11}$, $10^{12}$, $10^{13}$, or $10^{14}$ genome copies per kg. In certain embodiments, the effective amount of rAAV is $10^{10}$, $10^{11}$, $10^{12}$, $10^{13}$, $10^{14}$, or $10^{15}$ genome copies per subject.

An effective amount may also depend on the mode of administration. For example, targeting a prostate tissue by intravenous administration or intraperitoneal injection may require different (e.g., higher) doses, in some cases, than targeting prostate tissue by intraprostate injection. The invention is based, in part, on the recognition that intraperitoneal injection (i.p.) of rAAV does note mediate efficient transduction of prostate cells. Thus, in some embodiments, the injection is not intraperitoneal injection (i.p.). In some embodiments, the injection is intraprostate injection.

Intraprostate injection can be transperineal, transrectal, or transurethral, as described, for example, in Saemi et al., Indian J Urol. July-September; 24(3): 329-335: 2008. In some cases, multiple doses of a rAAV are administered.

Generally, the anatomy of the prostate can be classified in two ways: lobes and zones. For example, in humans the prostate gland has four distinct glandular regions under the zone classification: the peripheral zone (PZ), central zone (CZ), transition zone (TZ), and stroma. Under the lobe classification, the human prostate comprises four lobes: anterior lobe, posterior lobe, lateral lobe, and median lobe. In other species different terminology may be used to refer to different prostate structures, for example, in mouse prostate sites are referred to using anatomical positions, e.g., an anterior prostate, a dorsal lateral prostate, etc. See, for example, Selth, et al. international Journal of Cancer. 131 (3):652-661, 2012, and Wang, et al. Cancer Cell. 4(3):209-221, 2003. No matter the classification system, prostate tissue comprises at least three cell types: luminal prostate cells, basal prostate cells, and stromal prostate cells. In some embodiments, administration of an rAAV as described herein results in transduction of a prostate cell type selected from the group consisting of luminal prostate cells, basal prostate cells, and stromal prostate cells. In some embodiments, the administration results in transduction of at least two of the following prostate cell types: luminal prostate cells, basal prostate cells, and stromal prostate cells.

Prostate tissue can be healthy prostate tissue (e.g., prostate tissue not having a disease, or at risk of developing a prostate disease) or diseased prostate tissue (e.g., prostate tissue having prostatitis, BPH, or prostate cancer). As used herein, "at risk of developing a prostate disease" refers to a subject having an increased probability of developing a prostate disease than the general population due to the presence of a risk factor. Examples categories of risk factors for developing prostate disease include, but are not limited to: exposure to carcinogens (e.g., Agent Orange), kallikrein levels (e.g., PSA levels) age, race, family history (e.g., positive family history of prostate cancer), vasectomy, and dietary fat intake, for example as described in Pienta et al. Ann Intern Med. 118(10):793-803, 1993 and Carter et al. JAMA. 267(16):2215-2220, 1992.

Without wishing to be bound by any particular theory, efficient transduction of luminal, basal, and/or stromal prostate cells by rAAV described herein may be useful for the treatment of a subject having a prostate disease. Accordingly, methods and compositions for treating prostate disease are also provided herein. In some aspects, the disclosure provides a method for treating a prostate disease, the method comprising: administering to a subject having or suspected of having a prostate disease an effective amount of rAAV, wherein the rAAV comprises (i) a capsid protein having a serotype selected from the group consisting of AAV5, AAV6.2, AAV7, AAV8, AAV9, and AAVrh.10, and (ii) a nucleic acid comprising a promoter operably linked to a transgene.

As used herein, a "prostate disease" is a disease or condition of the prostate. Non-limiting examples of prostate diseases include, but are not limited to, prostatitis (e.g., acute prostatitis, chronic prostatitis), benign prostate hyperplasia (BPH), prostate cancer (e.g., acinar adenocarcinoma, ductal adenocarcinoma, transitional cell (urothelial cancer), squamous cell prostate cancer, carcinoid tumor of the prostate, small cell prostate cancer, prostate sarcoma (leiomyosarcoma), etc.).

Without wishing to be bound by any particular theory, rAAV-based delivery of a transgene encoding a gene associated with a prostate disease is useful for treatment of subjects having prostate disease. As used herein, "gene associated with a prostate disease" refers to any gene, wherein expression of that gene that provides a therapeutic benefit in a subject, e.g., to improve in the subject one or more symptoms of disease, e.g., a symptom of prostate disease (e.g., prostatitis, BPH, prostate cancer, etc.). A gene associated with prostate disease can be a protein, polypeptide, antibody or fragment thereof (e.g., ScR), toxin, or interfering RNA. Examples of genes associated with prostate disease include, but are not limited to Bcl-2, protein kinase G clusterin, miR34a, miR375, NkX3.1, PTEN, Maspin, CLCA2, and PMSA. Other examples of genes associated with prostate disease are known in the art and are described, for example, in Cooper et al., Nat Clin Pract Urol, December; 4(12):677-87; 2007. In some embodiments, a gene associated with prostate disease is a microRNA, for example miR34a. In some embodiments, miR34a comprises a nucleic acid sequence as set forth in SEQ ID NO: 15.

Recombinant Adeno-Associated Viruses (rAAVs)

In some aspects, the disclosure provides isolated AAVs. As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a nuclease and/or transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected.

In some aspects, the disclosure provides an rAAV having a capsid appropriate for targeting prostate tissue. In some embodiments, the capsid has a serotype selected from the group consisting of AAV5, AAV6.2, AAV7, AAV8, AAV9, and AAVrh.10. In some embodiments, the capsid has an AAV6.2 serotype (e.g., SEQ ID NO: 3) or an AAV7 serotype (e.g., SEQ ID NO: 4). The skilled artisan also recognizes that rAAV described herein may comprise variants of AAV5, AAV6.2, AAV7, AAV8, AAV9, and AAVrh.10 serotype capsid proteins. In some embodiments, the capsid protein comprises an amino acid sequence that is at least 70%, at least 80%, at least 90%, at least 95%, or at least 99% identical to any one of SEQ ID NO: 1-7.

Methods for obtaining recombinant AAVs having a desired capsid protein are well known in the art. (See, for example, US 200310138772), the contents of which are incorporated herein by reference in their entirety). Typically the methods involve culturing a host cell which contains a nucleic acid sequence encoding an AAV capsid protein; a functional rep gene; a recombinant AAV vector composed of. AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the instant disclosure relates to a host cell containing a nucleic acid that comprises a coding sequence encoding a gene associated with a prostate disease. In some embodiments, the instant disclosure relates to a composition comprising the host cell described above. In some embodiments, the composition comprising the host cell above further comprises a cryopreservative.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor. N.Y. Similarly, methods of generating rAAV virions are well known and the selection of a suitable method is not a limitation on the present disclosure. Sec, e.g., K. Fisher et al, J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In other aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology. 52:456. Sambrook et al. (1989) Molecular Cloning, a laboratory manual, Cold Spring Harbor Laboratories, New York, Davis et al. (1986) Basic Methods in Molecular Biology, Elsevier. and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognised by the synthetic machinery of the cell, or introduced synthetic machinery, required to initiate the specific transcription of a gene. The phrases "operatively positioned," "under control" or "under transcriptional control" means that the promoter is in the correct locution and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or functional RNA (e.g., guide RNA) from a transcribed gene.

The foregoing methods for packaging recombinant vectors in desired AAV capsids to produce the rAAVs of the disclosure are not meant to be limiting and other suitable methods will be apparent to the skilled artisan.

Isolated Nucleic Acids

A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

The skilled artisan will also realize that conservative amino acid substitutions may be made to provide functionally equivalent variants, or homologs of the capsid proteins. In some aspects the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g., Molecular Cloning: A Laboratory Manual. J. Sambrook, et al, eds., Second Edition, Cold Spring Harbor Laboratory Press, Cold Spring Harbor, New York, 1989, or Current Protocols in Molecular Biology, F. M. Ausubel, et al., eds., John Wiley & Sons. Inc., New York. Conservative substitutions of amino acids include substitutions made among amino acids within the following groups: (a) M, I, L, V; (b) F, Y, W; (c) K, R, H; (d) A, G; (c) S, T; (f) Q, N; and (g) E, D. Therefore, one can make conservative amino acid substitutions to the amino acid sequence of the proteins and polypeptides disclosed herein.

Recombinant AAV Vectors (rAAV Vectors)

"Recombinant AAV (rAAV) vectors" of the disclosure are typically composed of, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., gRNA) or other gene product, of interest. The nucleic acid coding sequence is operatively linked to regulatory components in a manner which permits transgene transcription, translation, and/or expression in a cell of a target tissue.

In some embodiments, the instant disclosure relates to a recombinant AAV (rAAV) vector comprising a nucleic acid sequence including a promoter operably linked to a transgene, wherein the transgene is a gene associated with a prostate disease. In some embodiments, a rAAV vector further comprises nucleic acid sequences encoding one or more AAV inverted terminal repeat sequences (ITRs), for example AAV2 ITRs. In some embodiments, a rAAV vector further comprises nucleic acid sequences encoding one or more AAV ITRs selected from the group consisting of AAV3. AAV4, AAV5, and AAV6.

The AAV sequences of the vector typically comprise the cis-acting 5' and 3' inverted terminal repeat sequences (Sex. e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types (e.g., AAV2, AAV3, AAV4, AAV5, or AAV6 ITR sequences).

In addition to the major elements identified above for the recombinant AAV vector, the vector also includes control elements necessary which are operably linked to the transgene in a manner which permits its transcription, translation and/or expression in a cell transfected with the plasmid vector or infected with the virus produced by the disclosure. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence (e.g., coding sequence) and regulatory sequences are said to be "operably" linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not as (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., gRNA). For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and/or other vector elements may be performed, as appropriate, and many such sequences are available [see. e.g., Sambrook et al, and references cited therein at, for example, pages 3.18 3.26 and 16.17 16.27 and Ausubel et al, Current Protocols in Molecular Biology. John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933: Mattion, N M et al., J Virology, November 1996; p. 8124-8127; Furler, S et al., Gene Therapy, 2001; 8: 864-873; and Halpin, C et al., The Plant Journal. 1999; 4: 45:3.459). The cleavage activity of the 2A sequence has previously been demonstrated in artificial systems including plasmids and gene therapy vectors (AAV and retroviruses) (Ryan, M D et al., EMBO, 1994; 4: 928-933: Mattion, N M et al., J Virology. November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, P et al., Human Gene Therapy, 2000; 11: 1921-1931; and Klump, H et al., Gene Therapy. 2001: 8: 811-817).

The precise nature of the regulatory sequences needed for gene expression in host cells may vary between species, tissues or cell types, but shall in general include, as necessary. 5' non-transcribed and 5' non-translated sequences involved with the initiation of transcription and translation respectively, such as a TATA box, capping sequence. CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see. e.g., Boshart et al. Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter is an enhanced chicken β-actin promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 268:1766-1769 (1995), sec also Harvey et al, Curr. Opin. Chem. Biol., 2:512-518 (1998)), the RU486-inducible system (Wang et al, Nat. Biotech., 15:239-243 (1997) and Wang et al, Gene Ther. 4:432-441 (1997)) and the rapamycin-inducible system (Magari et al, J. Clin. Invest., 100:2865-2872 (1997)). Still other types of inducible promoters which may be useful in this context are those which are regulated by a specific physiological state. e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter. Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et. al., J. Bone Miner. Res., 11:654-64 (1996)). CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et at, Cell. Mol. Neurobiol., 13:503-15 (1993)), neurofilament light-chain gene promoter (Piccioli et al., Proc. Natl. Acad. Sci. USA. 88:5611-5 (1991)), and the neuron-specific vgf gene promoter (Piccioli et al., Neuron. 15:373-84 (1995)), among others which will be apparent to the skilled artisan. In some embodiments, the promoter is a prostate-specific promoter, for example a prostate-specific antigen (PSA) promoter, a probasin promoter, a Moloney murine leukemia virus long terminal repeat (MMTV LTR) promoter, etc.

In some embodiments, one or more bindings sites for one or more of miRNAs are incorporated in a transgene of a rAAV vector, to inhibit the expression of the transgene in one or more tissues of an subject harboring the transgene. The skilled artisan will appreciate that binding sites may be selected to control the expression of a transgene in a tissue specific manner. For example, binding sites for the liver-specific miR-122 may be incorporated into a transgene to inhibit expression of that transgene in the liver. The target sites in the mRNA may be in the 5' UTR, the 3' UTR or in the coding region. Typically, the target site is in the 3' UTR of the mRNA. Furthermore, the transgene may be designed such that multiple miRNAs regulate the mRNA by recognizing the same or multiple sites. The presence of multiple miRNA binding sites may result in the cooperative action of multiple RISCs and provide highly efficient inhibition of expression. The target site sequence may comprise a total of 5-100, 10-60, or mom nucleotides. The target site sequence may comprise at least 5 nucleotides of the sequence of a target gene binding site.

miRNAs

In some aspects, the disclosure relates to delivery of a transgene encoding microRNA 34a (miR34a) to a cell. miRNAs are natively expressed, typically as final 19-25 non-translated RNA products. miRNAs exhibit their activity through sequence-specific interactions with the 3' untranslated regions (UTR) of target mRNAs. These endogenously expressed miRNAs form hairpin precursors which are subsequently processed into a miRNA duplex, and further into a "mature" single stranded miRNA molecule. This mature miRNA guides a multiprotein complex, miRISC, which identifies target site, e.g., in the 3' UTR regions, of target mRNAs based upon their complementarily to the mature miRNA.

Without wishing to be bound by any particular theory, miR34a is known to function as a regulator of tumor suppression in cells. Accordingly, in some embodiments, delivery of a transgene encoding miR34a to a cell is useful for treatment of certain diseases characterized by reduction of miR34a expression or activity (e.g., certain cancers). Examples of cancers characterized by a reduction of miR34a expression or activity include but are not limited to prostate cancer, pancreatic cancer, breast cancer, colorectal cancer, cervical cancer, certain brain cancers (e.g., glioblastoma, medulloblastoma, etc.). In some embodiments, miR34a regulates cancer stem cells, such as prostate cancer stem cells, lung cancer stem cells, etc., for example as described in Misso et al. (2014) *Mol. Ther. Nucleic Acids* 3, e194: doi:10.1038/mtna.2014.47.

Thus, in some embodiments, the disclosure provides a method for treating cancer, the method comprising delivering a transgene encoding miR34a to a subject having a cancer characterized by a reduction in mir34a expression or activity.

In some aspects, the disclosure relates to the discovery that overexpression of certain miRNAs (e.g., miR34a) reduces prostate cancer cell viability and cell migration. Accordingly, in some aspects, the disclosure provides methods and compositions for treating prostate cancer by over-expressing miRNAs (e.g., miR34a) in a subject in need thereof. miRNAs and other small interfering nucleic acids regulate gene expression via target RNA transcript cleavage/degradation or translational repression of the target messenger RNA (mRNA).

In some embodiments, a miR34a miRNA described by the disclosure comprises or consists of a nucleic acid sequence as set forth in SEQ 11) NO: 15. Variants of SEQ ID NO: 15 are also contemplated by the disclosure. For example, in some embodiments, a miR34a sequence is at least 75%, at least 80%, at least 85%, at least 90%, at least 95%, or at least 99% identical to SEQ ID NO: 15.

It should be appreciated that, in some embodiments, a miR34a miRNA is an inhibitory nucleic acid (e.g., miRNA, pri-miRNA, amiRNA, dsRNA, shRNA, siRNA, etc.) that is complementary with and specifically binds to a target site sequence (e.g., a miR34a binding site) of a gene (e.g., CCND1, TOP2A, CD44, etc.) and inhibits expression of the target sequence (e.g., inhibits transcription, translation, or production a protein encoded by the target sequence). In some embodiments, a target sequence comprises at least 5 contiguous nucleotides that are complementary with a sequence as set forth in SEQ ID NO: 15.

Recombinant AAV Administration Methods

The rAAVs may be delivered to a subject in compositions according to any appropriate methods known in the art. The rAAV, preferably suspended in a physiologically compatible carrier (i.e., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments, a host animal does not include a human.

Delivery of the rAAVs to a mammalian subject may be by, for example, intraprostate injection, in some embodiments, the intraprostate injection is transperineal, transrectal, or transurethral injection. In some embodiments, the injection is not intraperitoneal injection (i.p.).

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

In some embodiments, a composition further comprises a pharmaceutically acceptable carrier. Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAVs are administered in sufficient amounts to transfect the cells of a desired tissue (e.g., prostate tissue) and to provide sufficient levels of gene transfer and expression without undue adverse effects. Examples of pharmaceutically acceptable mutes of administration include, but are not limited to, direct delivery to the selected organ (e.g., intraprostate delivery to the prostate), oral, inhalation (including intranasal and intratracheal delivery), intraocular, intravenous, intramuscular, subcutaneous, intradermal, intratumoral, and other parental mutes of administration. Routes of administration may be combined, if desired.

The dose of rAAV visions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of the rAAV is generally in the range of from about 1 ml to about 100 ml of solution containing from about $10^9$ to $10^{16}$ genome copies. In some cases, a dosage between about $10^{11}$ to $10^{13}$ rAAV genome copies is appropriate. In certain embodiments, $10^{11}$ or $10^{12}$ rAAV genome copies is effective to target prostate tissue. In some cases, stable transgenic animals are produced by multiple doses of an rAAV.

In some embodiments, a dose of rAAV is administered to a subject no more than once per calendar day (e.g., a 24-hour period). In some embodiments, a dose of rAAV is administered to a subject no more than once per 2, 3, 4, 5, 6, or 7 calendar days. In some embodiments, a dose of rAAV is administered to a subject no more than once per calendar week (e.g., 7 calendar days). In some embodiments, a dose of rAAV is administered to a subject no more than bi-weekly (e.g., once in a two calendar week period). In some embodiments, a dose of rAAV is administered to a subject no more than once per calendar month (e.g., once in 30 calendar days). In some embodiments, a dose of rAAV is administered to a subject no more than once per six calendar months. In some embodiments, a dose of rAAV is administered to a subject no more than once per calendar year (e.g., 365 days or 366 days in a leap year).

In some embodiments, rAAV compositions are formulated to reduce aggregation of AAV particles in the composition, particularly when: high rAAV concentrations are present (e.g., ~$10^{13}$ GC/ml or more). Appropriate methods for reducing aggregation of may be used, including, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments, rAAVs in suitably formulated pharmaceutical compositions disclosed herein are delivered directly to target tissue, e.g., direct to prostate tissue. However, in certain circumstances it may be desirable to separately or in addition deliver the rAAV-based therapeutic constructs via another route, e.g., subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641, 515 and 5,399,363 (each specifically incorporated herein by reference in its entirety) may be used to deliver rAAVs. In some embodiments, a preferred mode of administration is by intraprostate injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a suitable sterile aqueous medium may be employed. For example, one dosage tray be dissolved in 1 ml of isotonic NaCl solution and either added to 1000 ml of hypodermoclysis fluid or injected at the proposed site of infusion. (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host. Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered trangenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S.

Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 .ANG., containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

Kits and Related Compositions

The agents described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

In some embodiments, the instant disclosure relates to a kit for producing a rAAV, the kit comprising a container housing an isolated nucleic acid encoding an AAV capsid protein, selected from any one of SEQ ID NO: 1-7. In some embodiments, the kit further comprises instructions for producing the rAAV. In some embodiments, the kit further comprises at least one container housing a recombinant AAV vector, wherein the recombinant AAV vector comprises a transgene (e.g., a gene associated with prostate disease).

In some embodiments, the instant disclosure relates to a kit comprising a container housing a recombinant AAV having an isolated AAV capsid protein having an amino acid sequence as set forth in SEQ ID NO: 3 or SEQ ID NO: 4.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for producing specific somatic animal models.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such us radiation sterilisation, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The instructions included within the kit may involve methods for detecting a latent AAV in a cell. In addition, kits of the disclosure may include, instructions, a negative and/or positive control, containers, diluents and buffers for the sample, sample preparation tubes and a printed or electronic table of reference AAV sequence for sequence comparisons.

---

Sequences

>AAV5 capsid protein amino acid sequence (SEQ ID NO: 1)

MSFVDHPPDWLEEVGEGLREFLGLEAGPPKPKPNQQHQDQARGLVLPGYNYLGPGN

GLDRGEPVNRADEVAREHDISYNEQLEAGDNPYLKYNHADAEFQEKLADDTSFGGN

-continued

Sequences

LGKAVFQAKKRVLEPFGLVEEGAKTAPTGKRIDDHFPKRKKARTEEDSKPSTSSDAE

AGPSGSQQLQIPAQPASSLGADTMSAGGGGPLGDNNQGADGVGNASGDWHCDSTW

MGDRVVTKSTRTWVLPSYNNHQYREIKSGSVDGSNANAYFGYSTPWGYFDFNRFHS

HWSPRDWQRLINNYWGFRPRSLRVKIFNIQVKEVTVQDSTTTIANNLTSTVQVFTDD

DYQLPYVVGNGTEGCLPAFPPQVFTLPQYGYATLNRDNTENPTERSSFFCLEYFPSK

MLRTGNNFEFTYNFEEVPFHSSFAPSQNLFKLANPLVDQYLYRFVSTNNTGGVQFNK

NLAGRYANTYKNWFPGPMGRTQGWNLGSGVNRASVSAFATTNRMELEGASYQVPP

QPNGMTNNLQGSNTYALENTMIFNSQPANPGTTATYLEGNMLITSESETQPVNRVAY

NVGGQMATNNQSSTTAPATGTYNLQEIVPGSVWMERDVYLQGPIWAKIPETGAHFH

PSPAMGGFGLKHPPPMMLIKNTPVPGNITSFSDVPVSSFITQYSTGQVTVEMEWELKK

ENSKRWNPEIQYTNNYNDPQFVDFAPDSTGEYRTTRPIGTRYLTRPL

>AAV6 capsid protein amino acid sequence
                                                    (SEQ ID NO: 2)
MAADGYLPDWLEDNLSEGIREWWDLKPGAPKPKANQQKQDDGRGLVLPGYKYLG

PFNGLDKGEPVNAADAAALEHDKAYDQQLKAGDNPYLRYNHADAEFQERLQEDTS

FGGNLGRAVFQAKKRVLEPFGLVEEGAKTAPGKKRPVEQSPQEPDSSSGIGKTGQQP

AKKRLNFGQTGDSESVPDPQPLGEPPATPAAVGPTTMASGGGAPMADNNEGADGV

GNASGNWHCDSTWLGDRVITTSTRTWALPTYNNHLYKQISSASTGASNDNHYFGYS

TPWGYFDFNRFHCHFSPRDWQRLINNNWGFRPKRLNFKLFNIQVKEVTTNDGVTTIA

NNLTSTVQVFSDSEYQLPYVLGSAHQGCLPPFPADVFMIPQYGYLTLNNGSQAVGRS

SFYCLEYFPSQMLRTGNNFTFSYTFEDVPFHSSYAHSQSLDRLMNPLIDQYLYYLNRT

QNQSGSAQNKDLLFSRGSPAGMSVQPKNWLPGPCYRQQRVSKTKTDNNNSNFTWT

GASKYNLNGRESIINPGTAMASHKDDKDKFFPMSGVMIFGKESAGASNTALDNVMIT

DEEEIKATNPVATERFGTVAVNLQSSSTDPATGDVHVMGALPGMVWQDRDVYLQG

PIWAKIPHTDGHFHPSPLMGGFGLKHPPPQILIKNTPVPANPPAEFSATKFASFITQYST

GQVSVEIEWELQKENSKRWNPEVQYTSNYAKSANVDFTVDNNGLYTEPRPIGTRYL

TRPL

>AAV6.2 capsid protein amino acid sequence
                                                    (SEQ ID NO: 3)
MAADGYLPDWLEDNLSEGIREWWDLKPGAPKPKANQQKQDDGRGLVLPGYKYLG

PFNGLDKGEPVNAADAAALEHDKAYDQQLKAGDNPYLRYNHADAEFQERLQEDTS

FGGNLGRAVFQAKKRVLEPLGLVEEGAKTAPGKKRPVEQSPQEPDSSSGIGKTGQQP

AKKRLNFGQTGDSESVPDPQPLGEPPATPAAVGPTTMASGGGAPMADNNEGADGV

GNASGNWHCDSTWLGDRVITTSTRTWALPTYNNHLYKQISSASTGASNDNHYFGYS

TPWGYFDFNRFHCHFSPRDWQRLINNNWGFRPKRLNFKLFNIQVKEVTTNDGVTTIA

NNLTSTVQVFSDSEYQLPYVLGSAHQGCLPPFPADVFMIPQYGYLTLNNGSQAVGRS

SFYCLEYFPSQMLRTGNNFTFSYTFEDVPFHSSYAHSQSLDRLMNPLIDQYLYYLNRT

QNQSGSAQNKDLLFSRGSPAGMSVQPKNWLPGPCYRQQRVSKTKTDNNNSNFTWT

GASKYNLNGRESIINPGTAMASHKDDKDKFFPMSGVMIFGKESAGASNTALDNVMIT

DEEEIKATNPVATERFGTVAVNLQSSSTDPATGDVHVMGALPGMVWQDRDVYLQG

-continued

Sequences

PIWAKIPHTDGHFHPSPLMGGFGLKHPPPQILIKNTPVPANPPAEFSATKFASFITQYST

GQVSVEIEWELQKENSKRWNPEVQYTSNYAKSANVDFTVDNNGLYTEPRPIGTRYL

TRPL

>AAV7 capsid protein amino acid sequence
                                          (SEQ ID NO: 4)
MAADGYLPDWLEDNLSEGIREWWDLKPGAPKPKANQQKQDNGRGLVLPGYKYLG

PFNGLDKGEPVNAADAAALEHDKAYDQQLKAGDNPYLRYNHADAEFQERLQEDTS

FGGNLGRAVFQAKKRVLEPLGLVEEGAKTAPAKKRPVEPSPQRSPDSSTGIGKKGQQ

PARKRLNFGQTGDSESVPDPQPLGEPPAAPSSVGSGTVAAGGGAPMADNNEGADGV

GNASGNWHCDSTWLGDRVITTSTRTWALPTYNNHLYKQISSETAGSTNDNTYFGYS

TPWGYFDFNRFHCHFSPRDWQRLINNNWGFRPKKLRFKLFNIQVKEVTTNDGVTTIA

NNLTSTIQVFSDSEYQLPYVLGSAHQGCLPPFPADVFMIPQYGYLTLNNGSQSVGRSS

FYCLEYFPSQMLRTGNNFEFSYSFEDVPFHSSYAHSQSLDRLMNPLIDQYLYYLARTQ

SNPGGTAGNRELQFYQGGPSTMAEQAKNWLPGPCFRQQRVSKTLDQNNNSNFAWT

GATKYHLNGRNSLVNPGVAMATHKDDEDRFFPSSGVLIFGKTGATNKTTLENVLMT

NEEEIRPTNPVATEEYGIVSSNLQAANTAAQTQVVNNQGALPGMVWQNRDVYLQGP

IWAKIPHTDGNFHPSPLMGGFGLKHPPPQILIKNTPVPANPPEVFTPAKFASFITQYSTG

QVSVEIEWELQKENSKRWNPEIQYTSNFEKQTGVDFAVDSQGVYSEPRPIGTRYLTR

NL

>AAV8 capsid protein amino acid sequence
                                          (SEQ ID NO: 5)
MAADGYLPDWLEDNLSEGIREWWALKPGAPKPKANQQKQDDGRGLVLPGYKYLG

PFNGLDKGEPVNAADAAALEHDKAYDQQLQAGDNPYLRYNHADAEFQERLQEDTS

FGGNLGRAVFQAKKRVLEPLGLVEEGAKTAPGKKRPVEPSPQRSPDSSTGIGKKGQQ

PARKRLNFGQTGDSESVPDPQPLGEPPAAPSGVGPNTMAAGGGAPMADNNEGADG

VGSSSGNWHCDSTWLGDRVITTSTRTWALPTYNNHLYKQISNGTSGGATNDNTYFG

YSTPWGYFDFNRFHCHFSPRDWQRLINNNWGFRPKRLSFKLFNIQVKEVTQNEGTKT

IANNLTSTIQVFTDSEYQLPYVLGSAHQGCLPPFPADVFMIPQYGYLTLNNGSQAVGR

SSFYCLEYFPSQMLRTGNNFQFTYTFEDVPFHSSYAHSQSLDRLMNPLIDQYLYYLSR

TQTTGGTANTQTLGFSQGGPNTMANQAKNWLPGPCYRQQRVSTTTGQNNNSNFAW

TAGTKYHLNGRNSLANPGIAMATHKDDEERFFPSNGILIFGKQNAARDNADYSDVM

LTSEEEIKTTNPVATEEYGIVADNLQQQNTAPQIGTVNSQGALPGMVWQNRDVYLQ

GPIWAKIPHTDGNFHPSPLMGGFGLKHPPPQILIKNTPVPADPPTTFNQSKLNSFITQYS

TGQVSVEIEWELQKENSKRWNPEIQYTSNYYKSTSVDFAVNTEGVYSEPRPIGTRYL

TRNL

>AAV9 capsid protein amino acid sequence
                                          (SEQ ID NO: 6)
MAADGYLPDWLEDNLSEGIREWWALKPGAPQPKANQQHQDNARGLVLPGYKYLG

PGNGLDKGEPVNAADAAALEHDKAYDQQLKAGDNPYLKYNHADAEFQERLKEDTS

FGGNLGRAVFQAKKRLLEPLGLVEEAAKTAPGKKRPVEQSPQEPDSSAGIGKSGAQP

AKKRLNFGQTGDTESVPDPQPIGEPPAAPSGVGSLTMASGGGAPVADNNEGADGVG

SSSGNWHCDSQWLGDRVITTSTRTWALPTYNNHLYKQISNSTSGGSSNDNAYFGYST

-continued

| Sequences |
| --- |

PWGYFDFNRFHCHFSPRDWQRLINNNWGFRPKRLNFKLFNIQVKEVTDNNGVKTIA

NNLTSTVQVFTDSDYQLPYVLGSAHEGCLPPFPADVFMIPQYGYLTLNDGSQAVGRS

SFYCLEYFPSQMLRTGNNFQFSYEFENVPFHSSYAHSQSLDRLMNPLIDQYLYYLSKT

INGSGQNQQTLKFSVAGPSNMAVQGRNYIPGPSYRQQRVSTTVTQNNNSEFAWPGA

SSWALNGRNSLMNPGPAMASHKEGEDRFFPLSGSLIFGKQGTGRDNVDADKVMITN

EEEIKTTNPVATESYGQVATNHQSAQAQAQTGWVQNQGILPGMVWQDRDVYLQGP

IWAKIPHTDGNFHPSPLMGGFGMKHPPPQILIKNTPVPADPPTAFNKDKLNSFITQYST

GQVSVEIEWELQKENSKRWNPEIQYTSNYYKSNNVEFAVNTEGVYSEPRPIGTRYLT

RNL

>AAVrh.10 capsid protein amino acid sequence (SEQ ID NO: 7)

MAADGYLPDWLEDNLSEGIREWWDLKPGAPKPKANQQKQDDGRGLVLPGYKYLG

PFNGLDKGEPVNAADAAALEHDKAYDQQLKAGDNPYLRYNHADAEFQERLQEDTS

FGGNLGRAVFQAKKRVLEPLGLVEEGAKTAPGKKRPVEPSPQRSPDSSTGIGKKGQQ

PAKKRLNFGQTGDSESVPDPQPIGEPPAGPSGLGSGTMAAGGGAPMADNNEGADGV

GSSSGNWHCDSTWLGDRVITTSTRTWALPTYNNHLYKQISNGTSGGSTNDNTYFGY

STPWGYFDFNRFHCHFSPRDWQRLINNNWGFRPKRLNFKLFNIQVKEVTQNEGTKTI

ANNLTSTIQVFTDSEYQLPYVLGSAHQGCLPPFPADVFMIPQYGYLTLNNGSQAVGR

SSFYCLEYFPSQMLRTGNNFEFSYQFEDVPFHSSYAHSQSLDRLMNPLIDQYLYYLSR

TQSTGGTAGTQQLLFSQAGPNNMSAQAKNWLPGPCYRQQRVSTTLSQNNNSNFAW

TGATKYHLNGRDSLVNPGVAMATHKDDEERFFPSSGVLMFGKQGAGKDNVDYSSV

MLTSEEEIKTTNPVATEQYGVVADNLQQQNAAPIVGAVNSQGALPGMVWQNRDVY

LQGPIWAKIPHTDGNFHPSPLMGGFGLKHPPPQILIKNTPVPADPPTTFSQAKLASFIT

QYSTGQVSVEIEWELQKENSKRWNPEIQYTSNYYKSTNVDFAVNTDGTYSEPRPIGT

RYLTRNL

>AAV5 capsid protein nucleic acid sequence (SEQ ID NO: 8)

ATGTCTTTTGTTGATCACCCTCCAGATTGGTTGGAAGAAGTTGGTGAAGGTCTTC

GCGAGTTTTTGGGCCTTGAAGCGGGCCCACCGAAACCAAAACCCAATCAGCAGC

ATCAAGATCAAGCCCGTGGTCTTGTGCTGCCTGGTTATAACTATCTCGGACCCGG

AAACGGTCTCGATCGAGGAGAGCCTGTCAACAGGGCAGACGAGGTCGCGCGAGA

GCACGACATCTCGTACAACGAGCAGCTTGAGGCGGGAGACAACCCCTACCTCAA

GTACAACCACGCGGACGCCGAGTTTCAGGAGAAGCTCGCCGACGACACATCCTT

CGGGGGAAACCTCGGAAAGGCAGTCTTTCAGGCCAAGAAAAGGGTTCTCGAACC

TTTTGGCCTGGTTGAAGAGGGTGCTAAGACGGCCCCTACCGGAAAGCGGATAGA

CGACCACTTTCCAAAAAGAAAGAAGGCCCGGACCGAAGAGGACTCCAAGCCTTC

CACCTCGTCAGACGCCGAAGCTGGACCCAGCGGATCCCAGCAGCTGCAAATCCC

AGCCCAACCAGCCTCAAGTTTGGGAGCTGATACAATGTCTGCGGGAGGTGGCGG

CCCATTGGGCGACAATAACCAAGGTGCCGATGGAGTGGGCAATGCCTCGGGAGA

TTGGCATTGCGATTCCACGTGGATGGGGGACAGAGTCGTCACCAAGTCCACCCG

-continued

Sequences

AACCTGGGTGCTGCCCAGCTACAACAACCACCAGTACCGAGAGATCAAAAGCGG

CTCCGTCGACGGAAGCAACGCCAACGCCTACTTTGGATACAGCACCCCCTGGGG

GTACTTTGACTTTAACCGCTTCCACAGCCACTGGAGCCCCCGAGACTGGCAAAGA

CTCATCAACAACTACTGGGGCTTCAGACCCCGGTCCCTCAGAGTCAAAATCTTCA

ACATTCAAGTCAAAGAGGTCACGGTGCAGGACTCCACCACCACCATCGCCAACA

ACCTCACCTCCACCGTCCAAGTGTTTACGGACGACGACTACCAGCTGCCCTACGT

CGTCGGCAACGGGACCGAGGGATGCCTGCCGGCCTTCCCTCCGCAGGTCTTTACG

CTGCCGCAGTACGGTTACGCGACGCTGAACCGCGACAACACAGAAAATCCCACC

GAGAGGAGCAGCTTCTTCTGCCTAGAGTACTTTCCCAGCAAGATGCTGAGAACG

GGCAACAACTTTGAGTTTACCTACAACTTTGAGGAGGTGCCCTTCCACTCCAGCT

TCGCTCCCAGTCAGAACCTCTTCAAGCTGGCCAACCCGCTGGTGGACCAGTACTT

GTACCGCTTCGTGAGCACAAATAACACTGGCGGAGTCCAGTTCAACAAGAACCT

GGCCGGGAGATACGCCAACACCTACAAAAACTGGTTCCCGGGGCCCATGGGCCG

AACCCAGGGCTGGAACCTGGGCTCCGGGGTCAACCGCGCCAGTGTCAGCGCCTT

CGCCACGACCAATAGGATGGAGCTCGAGGGCGCGAGTTACCAGGTGCCCCCGCA

GCCGAACGGCATGACCAACAACCTCCAGGGCAGCAACACCTATGCCCTGGAGAA

CACTATGATCTTCAACAGCCAGCCGGCGAACCCGGGCACCACCGCCACGTACCTC

GAGGGCAACATGCTCATCACCAGCGAGAGCGAGACGCAGCCGGTGAACCGCGTG

GCGTACAACGTCGGCGGGCAGATGGCCACCAACAACCAGAGCTCCACCACTGCC

CCCGCGACCGGCACGTACAACCTCCAGGAAATCGTGCCCGGCAGCGTGTGGATG

GAGAGGGACGTGTACCTCCAAGGACCCATCTGGGCCAAGATCCCAGAGACGGGG

GCGCACTTTCACCCCTCTCCGGCCATGGGCGGATTCGGACTCAAACACCCACCGC

CCATGATGCTCATCAAGAACACGCCTGTGCCCGGAAATATCACCAGCTTCTCGGA

CGTGCCCGTCAGCAGCTTCATCACCCAGTACAGCACCGGGCAGGTCACCGTGGA

GATGGAGTGGGAGCTCAAGAAGGAAAACTCCAAGAGGTGGAACCCAGAGATCC

AGTACACAAACAACTACAACGACCCCCAGTTTGTGGACTTTGCCCCGGACAGCA

CCGGGGAATACAGAACCACCAGACCTATCGGAACCCGATACCTTACCCGACCCC

TT

>AAV6 capsid nucleic acid sequence
(SEQ ID NO: 9)
ATGGCTGCCGATGGTTATCTTCCAGATTGGCTCGAGGACAACCTCTCTGAGGGCA

TTCGCGAGTGGTGGGACTTGAAACCTGGAGCCCCGAAACCCAAAGCCAACCAGC

AAAAGCAGGACGACGGCCGGGGTCTGGTGCTTCCTGGCTACAAGTACCTCGGAC

CCTTCAACGGACTCGACAAGGGGGAGCCCGTCAACGCGGCGGATGCAGCGGCCC

TCGAGCACGACAAGGCCTACGACCAGCAGCTCAAAGCGGGTGACAATCCGTACC

TGCGGTATAACCACGCCGACGCCGAGTTTCAGGAGCGTCTGCAAGAAGATACGT

CTTTTGGGGGCAACCTCGGGCGAGCAGTCTTCCAGGCCAAGAAGAGGGTTCTCG

AACCTTTTGGTCTGGTTGAGGAAGGTGCTAAGACGGCTCCTGGAAAGAAACGTC

CGGTAGAGCAGTCGCCACAAGAGCCAGACTCCTCCTCGGGCATTGGCAAGACAG

GCCAGCAGCCCGCTAAAAAGAGACTCAATTTTGGTCAGACTGGCGACTCAGAGT

-continued

---
Sequences
---

CAGTCCCCGACCCACAACCTCTCGGAGAACCTCCAGCAACCCCCGCTGCTGTGGG

ACCTACTACAATGGCTTCAGGCGGTGGCGCACCAATGGCAGACAATAACGAAGG

CGCCGACGGAGTGGGTAATGCCTCAGGAAATTGGCATTGCGATTCCACATGGCT

GGGCGACAGAGTCATCACCACCAGCACCCGAACATGGGCCTTGCCCACCTATAA

CAACCACCTCTACAAGCAAATCTCCAGTGCTTCAACGGGGGCCAGCAACGACAA

CCACTACTTCGGCTACAGCACCCCCTGGGGGTATTTTGATTTCAACAGATTCCAC

TGCCATTTCTCACCACGTGACTGGCAGCGACTCATCAACAACAATTGGGGATTCC

GGCCCAAGAGACTCAACTTCAAGCTCTTCAACATCCAAGTCAAGGAGGTCACGA

CGAATGATGGCGTCACGACCATCGCTAATAACCTTACCAGCACGGTTCAAGTCTT

CTCGGACTCGGAGTACCAGTTGCCGTACGTCCTCGGCTCTGCGCACCAGGGCTGC

CTCCCTCCGTTCCCGGCGGACGTGTTCATGATTCCGCAGTACGGCTACCTAACGC

TCAACAATGGCAGCCAGGCAGTGGGACGGTCATCCTTTTACTGCCTGGAATATTT

CCCATCGCAGATGCTGAGAACGGGCAATAACTTTACCTTCAGCTACACCTTCGAG

GACGTGCCTTTCCACAGCAGCTACGCGCACAGCCAGAGCCTGGACCGGCTGATG

AATCCTCTCATCGACCAGTACCTGTATTACCTGAACAGAACTCAGAATCAGTCCG

GAAGTGCCCAAAACAAGGACTTGCTGTTTAGCCGGGGGTCTCCAGCTGGCATGTC

TGTTCAGCCCAAAAACTGGCTACCTGGACCCTGTTACCGGCAGCAGCGCGTTTCT

AAAACAAAAACAGACAACAACAACAGCAACTTTACCTGGACTGGTGCTTCAAAA

TATAACCTTAATGGGCGTGAATCTATAATCAACCCTGGCACTGCTATGGCCTCAC

ACAAAGACGACAAAGACAAGTTCTTTCCCATGAGCGGTGTCATGATTTTTGGAAA

GGAGAGCGCCGGAGCTTCAAACACTGCATTGGACAATGTCATGATCACAGACGA

AGAGGAAATCAAAGCCACTAACCCCGTGGCCACCGAAAGATTTGGGACTGTGGC

AGTCAATCTCCAGAGCAGCAGCACAGACCCTGCGACCGGAGATGTGCATGTTAT

GGGAGCCTTACCTGGAATGGTGTGGCAAGACAGAGACGTATACCTGCAGGGTCC

TATTTGGGCCAAAATTCCTCACACGGATGGACACTTTCACCCGTCTCCTCTCATG

GGCGGCTTTGGACTTAAGCACCCGCCTCCTCAGATCCTCATCAAAAACACGCCTG

TTCCTGCGAATCCTCCGGCAGAGTTTTCGGCTACAAAGTTTGCTTCATTCATCACC

CAGTATTCCACAGGACAAGTGAGCGTGGAGATTGAATGGGAGCTGCAGAAAGAA

AACAGCAAACGCTGGAATCCCGAAGTGCAGTATACATCTAACTATGCAAAATCT

GCCAACGTTGATTTCACTGTGGACAACAATGGACTTTATACTGAGCCTCGCCCCA

TTGGCACCCGTTACCTCACCCGTCCCCTG

>AAV6.2 capsid protein nucleic acid sequence (SEQ ID NO: 10)

ATGGCTGCCGATGGTTATCTTCCAGATTGGCTCGAGGACAACCTCTCTGAGGGCA

TTCGCGAGTGGTGGGACTTGAAACCTGGAGCCCCGAAACCCAAAGCCAACCAGC

AAAAGCAGGACGACGGCCGGGGTCTGGTGCTTCCTGGCTACAAGTACCTCGGAC

CCTTCAACGGACTCGACAAGGGGGAGCCCGTCAACGCGGCGGATGCAGCGGCCC

TCGAGCACGACAAGGCCTACGACCAGCAGCTCAAAGCGGGTGACAATCCGTACC

TGCGGTATAACCACGCCGACGCCGAGTTTCAGGAGCGTCTGCAAGAAGATACGT

-continued

Sequences

CTTTTGGGGGCAACCTCGGGCGAGCAGTCTTCCAGGCCAAGAAGAGGGTTCTCG

AACCTCTTGGTCTGGTTGAGGAAGGTGCTAAGACGGCTCCTGGAAAGAAACGTC

CGGTAGAGCAGTCGCCACAAGAGCCAGACTCCTCCTCGGGCATTGGCAAGACAG

GCCAGCAGCCCGCTAAAAAGAGACTCAATTTTGGTCAGACTGGCGACTCAGAGT

CAGTCCCCGACCCACAACCTCTCGGAGAACCTCCAGCAACCCCCGCTGCTGTGGG

ACCTACTACAATGGCTTCAGGCGGTGGCGCACCAATGGCAGACAATAACGAAGG

CGCCGACGGAGTGGGTAATGCCTCAGGAAATTGGCATTGCGATTCCACATGGCT

GGGCGACAGAGTCATCACCACCAGCACCCGAACATGGGCCTTGCCCACCTATAA

CAACCACCTCTACAAGCAAATCTCCAGTGCTTCAACGGGGGCCAGCAACGACAA

CCACTACTTCGGCTACAGCACCCCCTGGGGGTATTTTGATTTCAACAGATTCCAC

TGCCATTTCTCACCACGTGACTGGCAGCGACTCATCAACAACAATTGGGGATTCC

GGCCCAAGAGACTCAACTTCAAGCTCTTCAACATCCAAGTCAAGGAGGTCACGA

CGAATGATGGCGTCACGACCATCGCTAATAACCTTACCAGCACGGTTCAAGTCTT

CTCGGACTCGGAGTACCAGTTGCCGTACGTCCTCGGCTCTGCGCACCAGGGCTGC

CTCCCTCCGTTCCCGGCGGACGTGTTCATGATTCCGCAGTACGGCTACCTAACGC

TCAACAATGGCAGCCAGGCAGTGGGACGGTCATCCTTTTACTGCCTGGAATATTT

CCCATCGCAGATGCTGAGAACGGGCAATAACTTTACCTTCAGCTACACCTTCGAG

GACGTGCCTTTCCACAGCAGCTACGCGCACAGCCAGAGCCTGGACCGGCTGATG

AATCCTCTCATCGACCAGTACCTGTATTACCTGAACAGAACTCAGAATCAGTCCG

GAAGTGCCCAAAACAAGGACTTGCTGTTTAGCCGGGGGTCTCCAGCTGGCATGTC

TGTTCAGCCCAAAAACTGGCTACCTGGACCCTGTTACCGGCAGCAGCGCGTTTCT

AAAACAAAAACAGACAACAACAACAGCAACTTTACCTGGACTGGTGCTTCAAAA

TATAACCTTAATGGGCGTGAATCTATAATCAACCCTGGCACTGCTATGGCCTCAC

ACAAAGACGACAAAGACAAGTTCTTTCCCATGAGCGGTGTCATGATTTTTGGAAA

GGAGAGCGCCGGAGCTTCAAACACTGCATTGGACAATGTCATGATCACAGACGA

AGAGGAAATCAAAGCCACTAACCCCGTGGCCACCGAAAGATTTGGGACTGTGGC

AGTCAATCTCCAGAGCAGCAGCACAGACCCTGCGACCGGAGATGTGCATGTTAT

GGGAGCCTTACCTGGAATGGTGTGGCAAGACAGAGACGTATACCTGCAGGGTCC

TATTTGGGCCAAAATTCCTCACACGGATGGACACTTTCACCCGTCTCCTCTCATG

GGCGGCTTTGGACTTAAGCACCCGCCTCCTCAGATCCTCATCAAAAACACGCCTG

TTCCTGCGAATCCTCCGGCAGAGTTTTCGGCTACAAAGTTTGCTTCATTCATCACC

CAGTATTCCACAGGACAAGTGAGCGTGGAGATTGAATGGGAGCTGCAGAAAGAA

AACAGCAAACGCTGGAATCCCGAAGTGCAGTATACATCTAACTATGCAAAATCT

GCCAACGTTGATTTCACTGTGGACAACAATGGACTTTATACTGAGCCTCGCCCCA

TTGGCACCCGTTACCTCACCCGTCCCCTG

>AAV7 capsid protein nucleic acid sequence (SEQ ID NO: 11)

ATGGCTGCCGATGGTTATCTTCCAGATTGGCTCGAGGACAACCTCTCTGAGGGCA

TTCGCGAGTGGTGGGACCTGAAACCTGGAGCCCCGAAACCCAAAGCCAACCAGC

AAAAGCAGGACAACGGCCGGGGGTCTGGTGCTTCCTGGCTACAAGTACCTCGGAC

-continued

| Sequences |
|---|

```
CCTTCAACGGACTCGACAAGGGGGAGCCCGTCAACGCGGCGGACGCAGCGGCCC

TCGAGCACGACAAGGCCTACGACCAGCAGCTCAAAGCGGGTGACAATCCGTACC

TGCGGTATAACCACGCCGACGCCGAGTTTCAGGAGCGTCTGCAAGAAGATACGT

CATTTGGGGGCAACCTCGGGCGAGCAGTCTTCCAGGCCAAGAAGCGGGTTCTCG

AACCTCTCGGTCTGGTTGAGGAAGGCGCTAAGACGGCTCCTGCAAAGAAGAGAC

CGGTAGAGCCGTCACCTCAGCGTTCCCCCGACTCCTCCACGGGCATCGGCAAGAA

AGGCCAGCAGCCCGCCAGAAAGAGACTCAATTTCGGTCAGACTGGCGACTCAGA

GTCAGTCCCCGACCCTCAACCTCTCGGAGAACCTCCAGCAGCGCCCTCTAGTGTG

GGATCTGGTACAGTGGCTGCAGGCGGTGGCGCACCAATGGCAGACAATAACGAA

GGTGCCGACGGAGTGGGTAATGCCTCAGGAAATTGGCATTGCGATTCCACATGG

CTGGGCGACAGAGTCATTACCACCAGCACCCGAACCTGGGCCCTGCCCACCTAC

AACAACCACCTCTACAAGCAAATCTCCAGTGAAACTGCAGGTAGTACCAACGAC

AACACCTACTTCGGCTACAGCACCCCCTGGGGGTATTTTGACTTTAACAGATTCC

ACTGCCACTTCTCACCACGTGACTGGCAGCGACTCATCAACAACAACTGGGGATT

CCGGCCCAAGAAGCTGCGGTTCAAGCTCTTCAACATCCAGGTCAAGGAGGTCAC

GACGAATGACGGCGTTACGACCATCGCTAATAACCTTACCAGCACGATTCAGGT

ATTCTCGGACTCGGAATACCAGCTGCCGTACGTCCTCGGCTCTGCGCACCAGGGC

TGCCTGCCTCCGTTCCCGGCGGACGTCTTCATGATTCCTCAGTACGGCTACCTGAC

TCTCAACAATGGCAGTCAGTCTGTGGGACGTTCCTCCTTCTACTGCCTGGAGTAC

TTCCCCTCTCAGATGCTGAGAACGGGCAACAACTTTGAGTTCAGCTACAGCTTCG

AGGACGTGCCTTTCCACAGCAGCTACGCACACAGCCAGAGCCTGGACCGGCTGA

TGAATCCCCTCATCGACCAGTACTTGTACTACCTGGCCAGAACACAGAGTAACCC

AGGAGGCACAGCTGGCAATCGGGAACTGCAGTTTTACCAGGGCGGGCCTTCAAC

TATGGCCGAACAAGCCAAGAATTGGTTACCTGGACCTTGCTTCCGGCAACAAAG

AGTCTCCAAAACGCTGGATCAAAACAACAACAGCAACTTTGCTTGGACTGGTGC

CACCAAATATCACCTGAACGGCAGAAACTCGTTGGTTAATCCCGGCGTCGCCATG

GCAACTCACAAGGACGACGAGGACCGCTTTTTCCCATCCAGCGGAGTCCTGATTT

TTGGAAAAACTGGAGCAACTAACAAAACTACATTGGAAAATGTGTTAATGACAA

ATGAAGAAGAAATTCGTCCTACTAATCCTGTAGCCACGGAAGAATACGGGATAG

TCAGCAGCAACTTACAAGCGGCTAATACTGCAGCCCAGACACAAGTTGTCAACA

ACCAGGGAGCCTTACCTGGCATGGTCTGGCAGAACCGGGACGTGTACCTGCAGG

GTCCCATCTGGGCCAAGATTCCTCACACGGATGGCAACTTTCACCCGTCTCCTTT

GATGGGCGGCTTTGGACTTAAACATCCGCCTCCTCAGATCCTGATCAAGAACACT

CCCGTTCCCGCTAATCCTCCGGAGGTGTTTACTCCTGCCAAGTTTGCTTCGTTCAT

CACACAGTACAGCACCGGACAAGTCAGCGTGGAAATCGAGTGGGAGCTGCAGAA

GGAAAACAGCAAGCGCTGGAACCCGGAGATTCAGTACACCTCCAACTTTGAAAA

GCAGACTGGTGTGGACTTTGCCGTTGACAGCCAGGGTGTTTACTCTGAGCCTCGC

CCTATTGGCACTCGTTACCTCACCCGTAATCTG
```

-continued

| Sequences |
| --- |

>AAV8 capsid protein nucleic acid sequence (SEQ ID NO: 12)

ATGGCTGCCGATGGTTATCTTCCAGATTGGCTCGAGGACAACCTCTCTGAGGGCA

TTCGCGAGTGGTGGGCGCTGAAACCTGGAGCCCCGAAGCCCAAAGCCAACCAGC

AAAAGCAGGACGACGGCCGGGGTCTGGTGCTTCCTGGCTACAAGTACCTCGGAC

CCTTCAACGGACTCGACAAGGGGGAGCCCGTCAACGCGGCGGACGCAGCGGCCC

TCGAGCACGACAAGGCCTACGACCAGCAGCTGCAGGCGGGTGACAATCCGTACC

TGCGGTATAACCACGCCGACGCCGAGTTTCAGGAGCGTCTGCAAGAAGATACGT

CTTTTGGGGGCAACCTCGGGCGAGCAGTCTTCCAGGCCAAGAAGCGGGTTCTCG

AACCTCTCGGTCTGGTTGAGGAAGGCGCTAAGACGGCTCCTGGAAAGAAGAGAC

CGGTAGAGCCATCACCCCAGCGTTCTCCAGACTCCTCTACGGGCATCGGCAAGAA

AGGCCAACAGCCCGCCAGAAAAAGACTCAATTTTGGTCAGACTGGCGACTCAGA

GTCAGTTCCAGACCCTCAACCTCTCGGAGAACCTCCAGCAGCGCCCTCTGGTGTG

GGACCTAATACAATGGCTGCAGGCGGTGGCGCACCAATGGCAGACAATAACGAA

GGCGCCGACGGAGTGGGTAGTTCCTCGGGAAATTGGCATTGCGATTCCACATGG

CTGGGCGACAGAGTCATCACCACCAGCACCCGAACCTGGGCCCTGCCCACCTAC

AACAACCACCTCTACAAGCAAATCTCCAACGGGACATCGGGAGGAGCCACCAAC

GACAACACCTACTTCGGCTACAGCACCCCCTGGGGGTATTTTGACTTTAACAGAT

TCCACTGCCACTTTTCACCACGTGACTGGCAGCGACTCATCAACAACAACTGGGG

ATTCCGGCCCAAGAGACTCAGCTTCAAGCTCTTCAACATCCAGGTCAAGGAGGTC

ACGCAGAATGAAGGCACCAAGACCATCGCCAATAACCTCACCAGCACCATCCAG

GTGTTTACGGACTCGGAGTACCAGCTGCCGTACGTTCTCGGCTCTGCCCACCAGG

GCTGCCTGCCTCCGTTCCCGGCGGACGTGTTCATGATTCCCCAGTACGGCTACCT

AACACTCAACAACGGTAGTCAGGCCGTGGGACGCTCCTCCTTCTACTGCCTGGAA

TACTTTCCTTCGCAGATGCTGAGAACCGGCAACAACTTCCAGTTTACTTACACCTT

CGAGGACGTGCCTTTCCACAGCAGCTACGCCCACAGCCAGAGCTTGGACCGGCT

GATGAATCCTCTGATTGACCAGTACCTGTACTACTTGTCTCGGACTCAAACAACA

GGAGGCACGGCAAATACGCAGACTCTGGGCTTCAGCCAAGGTGGGCCTAATACA

ATGGCCAATCAGGCAAAGAACTGGCTGCCAGGACCCTGTTACCGCCAACAACGC

GTCTCAACGACAACCGGGCAAAACAACAATAGCAACTTTGCCTGGACTGCTGGG

ACCAAATACCATCTGAATGGAAGAAATTCATTGGCTAATCCTGGCATCGCTATGG

CAACACACAAAGACGACGAGGAGCGTTTTTTTCCCAGTAACGGGATCCTGATTTT

TGGCAAACAAAATGCTGCCAGAGACAATGCGGATTACAGCGATGTCATGCTCAC

CAGCGAGGAAGAAATCAAAACCACTAACCCTGTGGCTACAGAGGAATACGGTAT

CGTGGCAGATAACTTGCAGCAGCAAAACACGGCTCCTCAAATTGGAACTGTCAA

CAGCCAGGGGGCCTTACCCGGTATGGTCTGGCAGAACCGGGACGTGTACCTGCA

GGGTCCCATCTGGGCCAAGATTCCTCACACGGACGGCAACTTCCACCCGTCTCCG

CTGATGGGCGGCTTTGGCCTGAAACATCCTCCGCCTCAGATCCTGATCAAGAACA

CGCCTGTACCTGCGGATCCTCCGACCACCTTCAACCAGTCAAAGCTGAACTCTTT

CATCACGCAATACAGCACCGGACAGGTCAGCGTGGAAATTGAATGGGAGCTGCA

-continued

Sequences

GAAGGAAAACAGCAAGCGCTGGAACCCCGAGATCCAGTACACCTCCAACTACTA

CAAATCTACAAGTGTGGACTTTGCTGTTAATACAGAAGGCGTGTACTCTGAACCC

CGCCCCATTGGCACCCGTTACCTCACCCGTAATCTG

>AAV9 capsid protein nucleic acid sequence (SEQ ID NO: 13)

ATGGCTGCCGATGGTTATCTTCCAGATTGGCTCGAGGACAACCTTAGTGAAGGAA

TTCGCGAGTGGTGGGCTTTGAAACCTGGAGCCCCTCAACCCAAGGCAAATCAAC

AACATCAAGACAACGCTCGAGGTCTTGTGCTTCCGGGTTACAAATACCTTGGACC

CGGCAACGGACTCGACAAGGGGGAGCCGGTCAACGCAGCAGACGCGGCGGCCC

TCGAGCACGACAAGGCCTACGACCAGCAGCTCAAGGCCGGAGACAACCCGTACC

TCAAGTACAACCACGCCGACGCCGAGTTCCAGGAGCGGCTCAAAGAAGATACGT

CTTTTGGGGGCAACCTCGGGCGAGCAGTCTTCCAGGCCAAAAAGAGGCTTCTTGA

ACCTCTTGGTCTGGTTGAGGAAGCGGCTAAGACGGCTCCTGGAAAGAAGAGGCC

TGTAGAGCAGTCTCCTCAGGAACCGGACTCCTCCGCGGGTATTGGCAAATCGGGT

GCACAGCCCGCTAAAAAGAGACTCAATTTCGGTCAGACTGGCGACACAGAGTCA

GTCCCAGACCCTCAACCAATCGGAGAACCTCCCGCAGCCCCCTCAGGTGTGGGAT

CTCTTACAATGGCTTCAGGTGGTGGCGCACCAGTGGCAGACAATAACGAAGGTG

CCGATGGAGTGGGGTAGTTCCTCGGGAAATTGGCATTGCGATTCCCAATGGCTGGG

GGACAGAGTCATCACCACCAGCACCCGAACCTGGGCCCTGCCCACCTACAACAA

TCACCTCTACAAGCAAATCTCCAACAGCACATCTGGAGGATCTTCAAATGACAAC

GCCTACTTCGGCTACAGCACCCCCTGGGGGTATTTTGACTTCAACAGATTCCACT

GCCACTTCTCACCACGTGACTGGCAGCGACTCATCAACAACAACTGGGGATTCCG

GCCTAAGCGACTCAACTTCAAGCTCTTCAACATTCAGGTCAAAGAGGTTACGGAC

AACAATGGAGTCAAGACCATCGCCAATAACCTTACCAGCACGGTCCAGGTCTTC

ACGGACTCAGACTATCAGCTCCCGTACGTGCTCGGGTCGGCTCACGAGGGCTGCC

TCCCGCCGTTCCCAGCGGACGTTTTCATGATTCCTCAGTACGGGTATCTGACGCTT

AATGATGGAAGCCAGGCCGTGGGTCGTTCGTCCTTTTACTGCCTGGAATATTTCC

CGTCGCAAATGCTAAGAACGGGTAACAACTTCCAGTTCAGCTACGAGTTTGAGA

ACGTACCTTTCCATAGCAGCTACGCTCACAGCCAAAGCCTGGACCGACTAATGAA

TCCACTCATCGACCAATACTTGTACTATCTCTCAAAGACTATTAACGGTTCTGGA

CAGAATCAACAAACGCTAAAATTCAGTGTGGCCGGACCCAGCAACATGGCTGTC

CAGGGAAGAAACTACATACCTGGACCCAGCTACCGACAACAACGTGTCTCAACC

ACTGTGACTCAAAACAACAGCGAATTTGCTTGGCCTGGAGCTTCTTCTTGGG

CTCTCAATGGACGTAATAGCTTGATGAATCCTGGACCTGCTATGGCCAGCCACAA

AGAAGGAGAGGACCGTTTCTTTCCTTTGTCTGGATCTTTAATTTTTGGCAAACAA

GGAACTGGAAGAGACAACGTGGATGCGGACAAAGTCATGATAACCAACGAAGA

AGAAATTAAAACTACTAACCCGGTAGCAACGGAGTCCTATGGACAAGTGGCCAC

AAACCACCAGAGTGCCCAAGCACAGGCGCAGACCGGCTGGGTTCAAAACCAAGG

AATACTTCCGGGTATGGTTTGGCAGGACAGAGATGTGTACCTGCAAGGACCCATT

-continued

Sequences

TGGGCCAAAATTCCTCACACGGACGGCAACTTTCACCCTTCTCCGCTGATGGGAG

GGTTTGGAATGAAGCACCCGCCTCCTCAGATCCTCATCAAAAACACACCTGTACC

TGCGGATCCTCCAACGGCCTTCAACAAGGACAAGCTGAACTCTTTCATCACCCAG

TATTCTACTGGCCAAGTCAGCGTGGAGATCGAGTGGGAGCTGCAGAAGGAAAAC

AGCAAGCGCTGGAACCCGGAGATCCAGTACACTTCCAACTATTACAAGTCTAAT

AATGTTGAATTTGCTGTTAATACTGAAGGTGTATATAGTGAACCCCGCCCCATTG

GCACCAGATACCTGACTCGTAATCTG

>AAVrh.10 capsid protein nucleic acid sequence
(SEQ ID NO: 14)
TCGAGGACAACCTCTCTGAGGGCATTCGCGAGTGGTGGGACTTGAAACCTGGAG

CCCCGAAACCCAAAGCCAACCAGCAAAAGCAGGACGACGGCCGGGGTCTGGTGC

TTCCTGGCTACAAGTACCTCGGACCCTTCAACGGACTCGACAAGGGGGAGCCCGT

CAACGCGGCGGACGCAGCGGCCCTCGAGCACGACAAGGCCTACGACCAGCAGCT

CAAAGCGGGTGACAATCCGTACCTGCGGTATAACCACGCCGACGCCGAGTTTCA

GGAGCGTCTGCAAGAAGATACGTCTTTTGGGGGCAACCTCGGGCGAGCAGTCTT

CCAGGCCAAGAAGCGGGTTCTCGAACCTCTCGGTCTGGTTGAGGAAGGCGCTAA

GACGGCTCCTGGAAAGAAGAGACCGGTAGAGCCATCACCCCAGCGTTCTCCAGA

CTCCTCTACGGGCATCGGCAAGAAAGGCCAGCAGCCCGCGAAAAAGAGACTCAA

CTTTGGGCAGACTGGCGACTCAGAGTCAGTGCCCGACCCTCAACCAATCGGAGA

ACCCCCCGCAGGCCCCTCTGGTCTGGGATCTGGTACAATGGCTGCAGGCGGTGGC

GCTCCAATGGCAGACAATAACGAAGGCGCCGACGGAGTGGGTAGTTCCTCAGGA

AATTGGCATTGCGATTCCACATGGCTGGGCGACAGAGTCATCACCACCAGCACCC

GAACCTGGGCCCTCCCCACCTACAACAACCACCTCTACAAGCAAATCTCCAACGG

GACTTCGGGAGGAAGCACCAACGACAACACCTACTTCGGCTACAGCACCCCCTG

GGGGTATTTTGACTTTAACAGATTCCACTGCCACTTCTCACCACGTGACTGGCAG

CGACTCATCAACAACAACTGGGGATTCCGGCCCAAGAGACTCAACTTCAAGCTCT

TCAACATCCAGGTCAAGGAGGTCACGCAGAATGAAGGCACCAAGACCATCGCCA

ATAACCTTACCAGCACGATTCAGGTCTTTACGGACTCGGAATACCAGCTCCCGTA

CGTCCTCGGCTCTGCGCACCAGGGCTGCCTGCCTCCGTTCCCGGCGGACGTCTTC

ATGATTCCTCAGTACGGGTACCTGACTCTGAACAATGGCAGTCAGGCCGTGGGCC

GTTCCTCCTTCTACTGCCTGGAGTACTTTCCTTCTCAAATGCTGAGAACGGGCAAC

AACTTTGAGTTCAGCTACCAGTTTGAGGACGTGCCTTTTCACAGCAGCTACGCGC

ACAGCCAAAGCCTGGACCGGCTGATGAACCCCCTCATCGACCAGTACCTGTACTA

CCTGTCTCGGACTCAGTCCACGGGAGGTACCGCAGGAACTCAGCAGTTGCTATTT

TCTCAGGCCGGGCCTAATAACATGTCGGCTCAGGCCAAAAACTGGCTACCCGGG

CCCTGCTACCGGCAGCAACGCGTCTCCACGACACTGTCGCAAAATAACAACAGC

AACTTTGCCTGGACCGGTGCCACCAAGTATCATCTGAATGGCAGAGACTCTCTGG

TAAATCCCGGTGTCGCTATGGCAACCCACAAGGACGACGAAGAGCGATTTTTTCC

GTCCAGCGGAGTCTTAATGTTTGGGAAACAGGGAGCTGGAAAAGACAACGTGGA

CTATAGCAGCGTTATGCTAACCAGTGAGGAAGAAATTAAAACCACCAACCCAGT

-continued

| Sequences |
| --- |

GGCCACAGAACAGTACGGCGTGGTGGCCGATAACCTGCAACAGCAAAACGCCGC

TCCTATTGTAGGGGCCGTCAACAGTCAAGGAGCCTTACCTGGCATGGTCTGGCAG

AACCGGGACGTGTACCTGCAGGGTCCTATCTGGGCCAAGATTCCTCACACGGAC

GGAAACTTTCATCCCTCGCCGCTGATGGGAGGCTTTGGACTGAAACACCCGCCTC

CTCAGATCCTGATTAAGAATACACCTGTTCCCGCGGATCCTCCAACTACCTTCAG

TCAAGCTAAGCTGGCGTCGTTCATCACGCAGTACAGCACCGGACAGGTCAGCGT

GGAAATTGAATGGGAGCTGCAGAAAGAAAACAGCAAACGCTGGAACCCAGAGA

TTCAATACACTTCCAACTACTACAAATCTACAAATGTGGACTTTGCTGTTAACAC

AGATGGCACTTATTCTGAGCCTCGCCCCATCGGCACCCGTTACCTCACCCGTAAT

CTGTAATTGCTTGTTAATCAATAAACCGGTTGATTCGTTTCAGTTGAACTTTGGTC

TCTGCGAAGGGCGAATTCGTTT

>miR34a nucleic acid sequence
                                                        (SEQ ID NO: 15)
AGGAATTCTGCTGGAGGAGTGTGTCATACCTCGGTAGGGTCCACTACACATCTTT

CTCCCGCAGCCTCTCCATCTTCCTGTGACTGCGGGCGCCTCAGCCTGGGCTGGCC

AGCTGTGAGTAATTCTTTGGCAGTGTCTTAGCTGGTTGTTGTGAGTATTAGCTAA

GGAAGCAATCAGCAAGTATACTGCCCTAGAAGTGCTGCACATTGTTGGGCCGAG

AAGGAAAAGGTCAGAGGTCAGCAACGCCCACACCCCTGAGAGGCGCTGGACTTG

CGGAGCTGCTCGACCATACTGGTGGGTATGGGATGGCGGCCGCGTCCC

>miR34a-Gluc expression construct nucleic acid sequence
                                                        (SEQ ID NO: 16)
CTGCGCGCTCGCTCGCTCACTGAGGCCGCCCGGGCAAAGCCCGGGCGTCGGGCG

ACCTTTGGTCGCCCGGCCTCAGTGAGCGAGCGAGCGCGCAGAGAGGGAGTGTAG

CCATGCTCTAGGAAGATCAATTCGGTACAATTCACGCGTCGACATTGATTATTGA

CTCTGGTCGTTACATAACTTACGGTAAATGGCCCGCCTGGCTGACCGCCCAACGA

CCCCGCCCATTGACGTCAATAATGACGTATGTTCCCATAGTAACGCCAATAGGGA

CTTTCCATTGACGTCAATGGGTGGAGTATTTACGGTAAACTGCCCACTTGGCAGT

ACATCAAGTGTATCATATGCCAAGTACGCCCCCTATTGACGTCAATGACGGTAAA

TGGCCCGCCTGGCATTATGCCCAGTACATGACCTTATGGGACTTTCCTACTTGGC

AGTACATCTACTCGAGGCCACGTTCTGCTTCACTCTCCCCATCTCCCCCCCCTCCC

CACCCCCAATTTTGTATTTATTTATTTTTTAATTATTTTGTGCAGCGATGGGGGCG

GGGGGGGGGGGGGGGGCGCGCGCCAGGCGGGGCGGGGCGGGGCGAGGGG

CGGGGCGGGGCGAGGCGGAGAGGTGCGGCGGCAGCCAATCAGAGCGGCGCGCT

CCGAAAGTTTCCTTTTATGGCGAGGCGGCGGCGGCGGCGCGCCCTATAAAAAGCG

AAGCGCGCGGCGGGCGGGAGCGGGATCAGCCACCGCGGTGGCGGCCCTAGAGTC

GATCGAGGAACTGAAAAACCAGAAAGTTAACTGGTAAGTTTAGTCTTTTTGTCTT

TTATTTCAGGAATTCTGCTGGAGGAGTGTGTCATACCTCGGTAGGGTCCACTACA

CATCTTTCTCCCGCAGCCTCTCCATCTTCCTGTGACTGCGGGCGCCTCAGCCTGGG

CTGGCCAGCTGTGAGTAATTCTTTGGCAGTGTCTTAGCTGGTTGTTGTGAGTATTA

GCTAAGGAAGCAATCAGCAAGTATACTGCCCTAGAAGTGCTGCACATTGTTGGG

-continued

| Sequences |
|---|
| CCGAGAAGGAAAAGGTCAGAGGTCAGCAACGCCCACACCCCTGAGAGGCGCTG |
| GACTTGCGGAGCTGCTCGACCATACTGGTGGGTATGGGATGGCGGCCGCGTCCC |
| GGATCCGGTGGTGGTGCAAATCAAAGAACTGCTCCTCAGTGGATGTTGCCTTTAC |
| TTCTAGGCCTGTACGGAAGTGTTACTTCTGCTCTAAAAGCTGCGGAATTGTACCC |
| GCGGCCGATCCACCGGTCGCCACCATCTAGCATGGGAGTCAAAGTTCTGTTTGCC |
| CTGATCTGCATCGCTGTGGCCGAGGCCAAGCCCACCGAGAACAACGAAGACTTC |
| AACATCGTGGCCGTGGCCAGCAACTTCGCGACCACGGATCTCGATGCTGACCGC |
| GGGAAGTTGCCCGGCAAGAAGCTGCCGCTGGAGGTGCTCAAAGAGATGGAAGCC |
| AATGCCCGGAAAGCTGGCTGCACCAGGGGCTGTCTGATCTGCCTGTCCCACATCA |
| AGTGCACGCCCAAGATGAAGAAGTTCATCCCAGGACGCTGCCACACCTACGAAG |
| GCGACAAAGAGTCCGCACAGGGCGGCATAGGCGAGGCGATCGTCGACATTCCTG |
| AGATTCCTGGGTTCAAGGACTTGGAGCCCATGGAGCAGTTCATCGCACAGGTCG |
| ATCTGTGTGTGGACTGCACAACTGGCTGCCTCAAAGGGCTTGCCAACGTGCAGTG |
| TTCTGACCTGCTCAAGAAGTGGCTGCCGCAACGCTGTGCGACCTTTGCCAGCAAG |
| ATCCAGGGCCAGGTGGACAAGATCAAGGGGGCCGGTGGTGACTAGCTCGACGCT |
| GATCAGCCTCGACTGTGCCTTCTAGTTGCCAGCCATCTGTTGTTTGCCCCTCCCCC |
| GTGCCTTCCTTGACCCTGGAAGGTGCCACTCCCACTGTCCTTTCCTAATAAAATG |
| AGGAAATTGCATCGCATTGTCTGAGTAGGTGTCATTCTATTCTGGGGGGTGGGGT |
| GGGGCAGGACAGCAAGGGGGAGGATTGGGAAGACAATTAGGTAGATAAGTAGC |
| ATGGCGGGTTAATCATTAACTACAAGGAACCCCTAGTGATGGAGTTGGCCACTCC |
| CTCTCTGCGCGCTCGCTCGCTCACTGAGGCCGGGCGACCAAAGGTCGCCCGACGC |
| CCGGGCTTTGCCCGGGCGGCCTCAGTGAGCGAGCGAGCGCGCAG |

EXAMPLES

Example 1. Adeno-Associated Virus Serotype Vectors Efficiently Transduce a Normal Prostate Tissue and Prostate Cancer Cells This example describes the unexpected result that certain serotypes of AAV vectors mediate highly efficient transduction in prostate tissue (e.g., mouse prostate tissue), which may be useful for performing mechanistic studies and gene therapy for prostate diseases, such as prostate cancer, in subjects such as dogs, monkeys, and humans (see, for example. Martijn C. Nawijn et al. European Urology Supplements, 7, 566-575, 2008 and Cory Abate-Shen, et al. Trends in Genetics. 18 (5):S1-S5, 2002).

It was previously shown that intraperitoneal (i.p.) injection of certain rAAV serotypes such as rAAV8 into WT mice could transduce tissues surrounding the peritoneal cavity such as the diaphragm, but prostate transduction has not been reported to the best of Applicants' knowledge. To screen for rAAV serotypes that efficiently transduce mouse prostate in vivo, i.p. injection of 12 serotypes of enhanced green fluorescent protein (EGFP)-expressing rAAV vectors was performed in WT C57BL/6 male mice, including rAAV2, 3b, 5, 6, 6.2, 7, 8, 9, rh.8, rh.10, rh.39 and rh.43.

Figure 1:
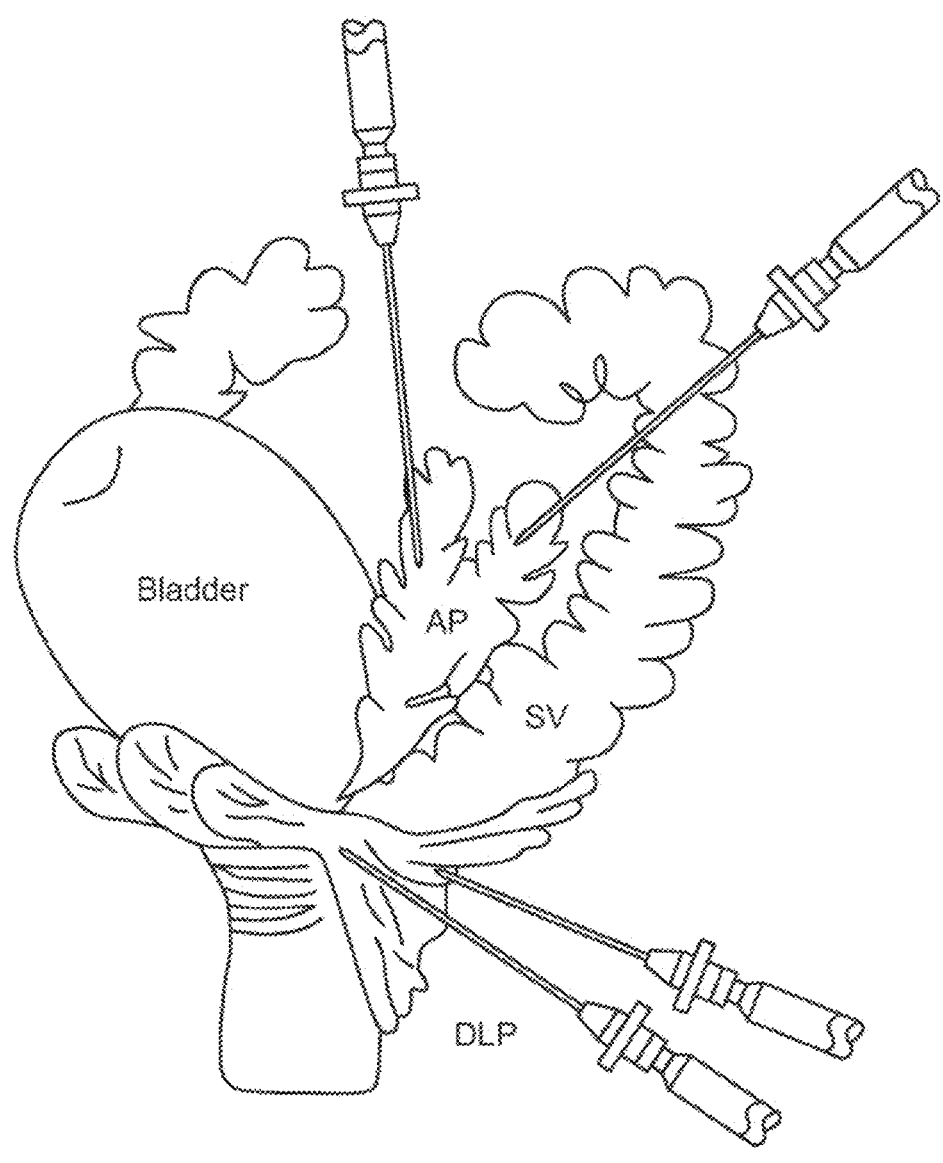
FIG. 1 shows a graphical depiction of the anatomical structure of mouse prostate and intraprostate injection sites. $1 \times 10^{11}$ GC per injection site of rAAV vectors were delivered into four sites as indicated by the syringes, namely the two lobes of the anterior prostate (AP) and two sites in the dorsal lateral prostate (DLP). SV: seminal vesicle.

EGFP fluorescence signal was barely observed in the prostate tissue sections three weeks after vector injection, indicating inefficient transduction. Next, the same panel of in rAAV vectors was injected directly into mouse prostate. The mouse prostate is divided into anterior prostate (AP) that contains two lobes and dorsal lateral prostate (DLP) (FIG. 1). rAAV vectors were thus injected into four sites per prostate, namely the two lobes of AP and two sites of DLP (FIG. 1).

Figure 2A:
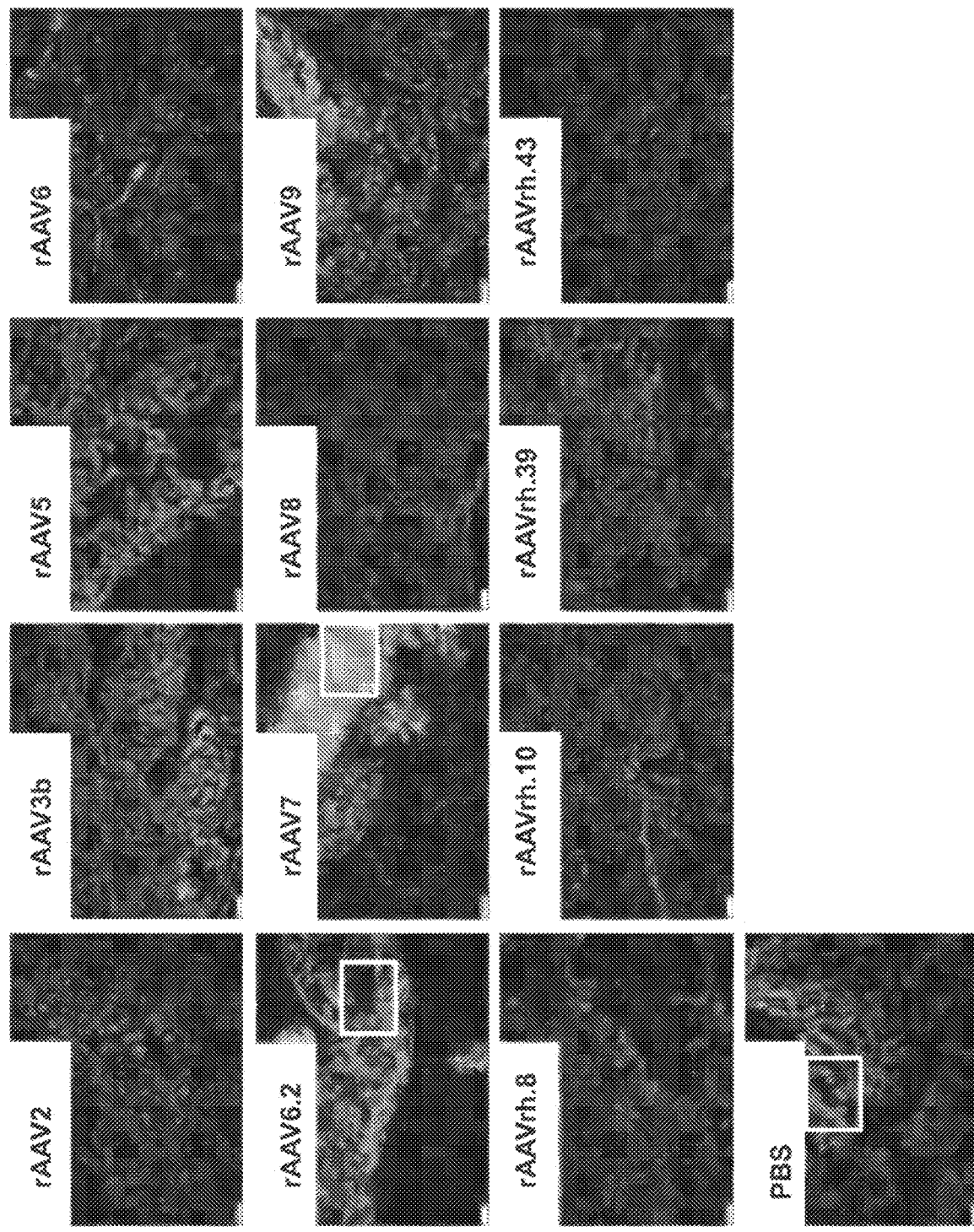
FIGS. 2A-2B show rAAV6.2, 7 and 9 efficiently transduced mouse AP following intraprostate injection.
Figure 2B:
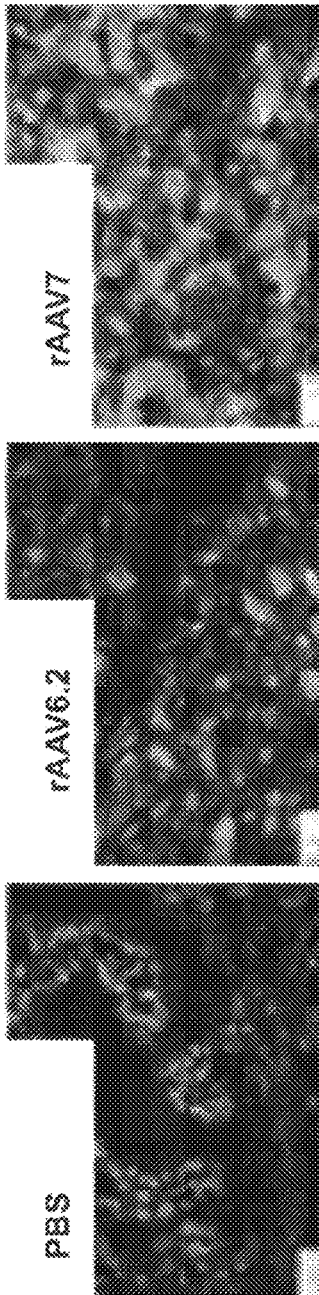
Figure 3A:
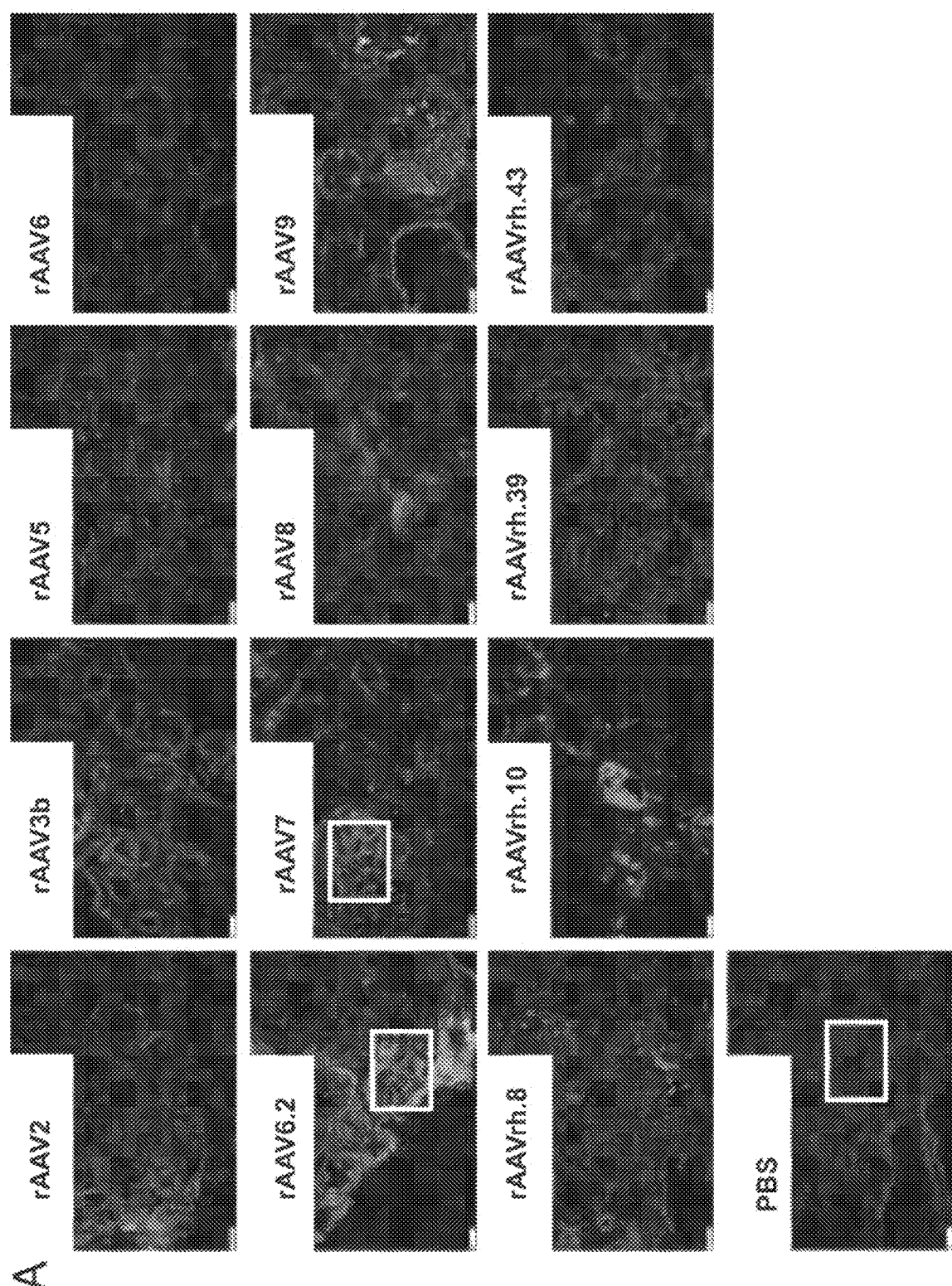
FIGS. 3A-3B show rAAV6.2, and 7 efficiently transduced mouse DLP following intraprostate injection.
Figure 3B:
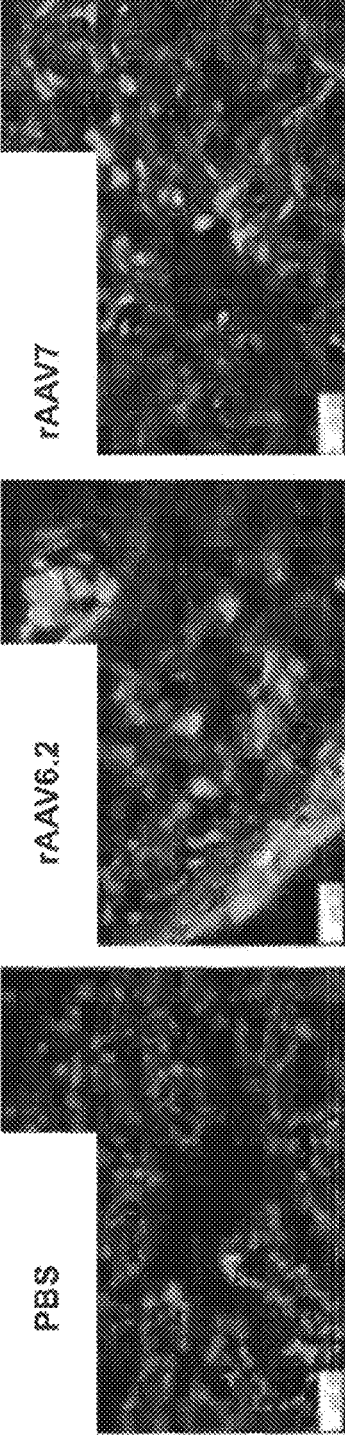
Figures 4A, 4B:
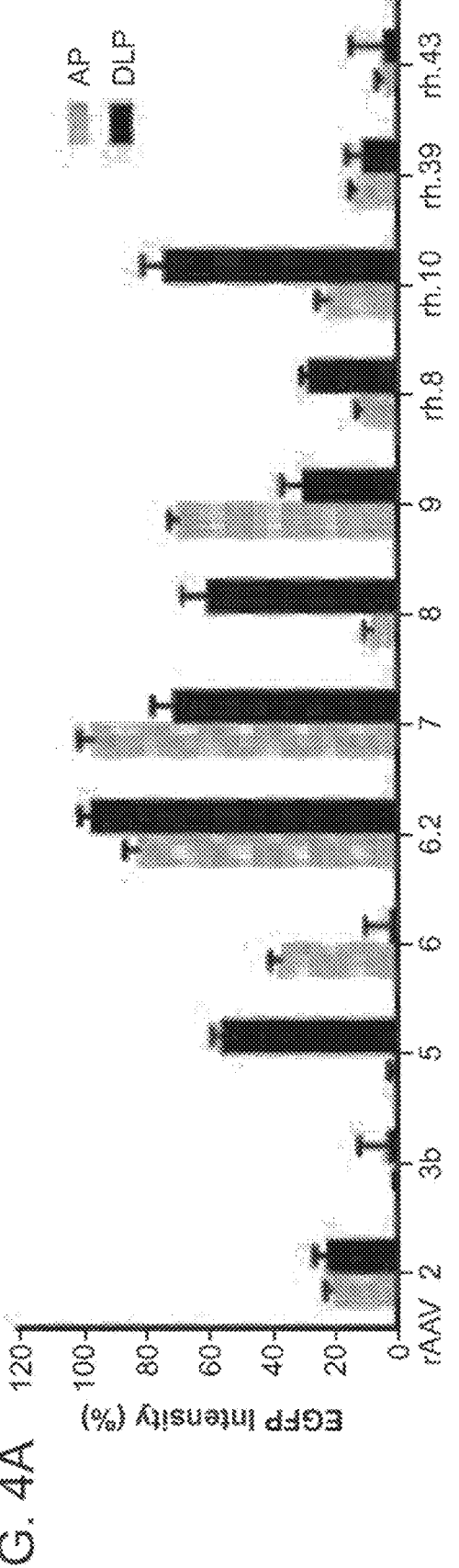
FIGS. 4A-4B show rAAV6.2 and rAAV7 efficiently transduced mouse prostate following intraprostate injection.
Figure 5:
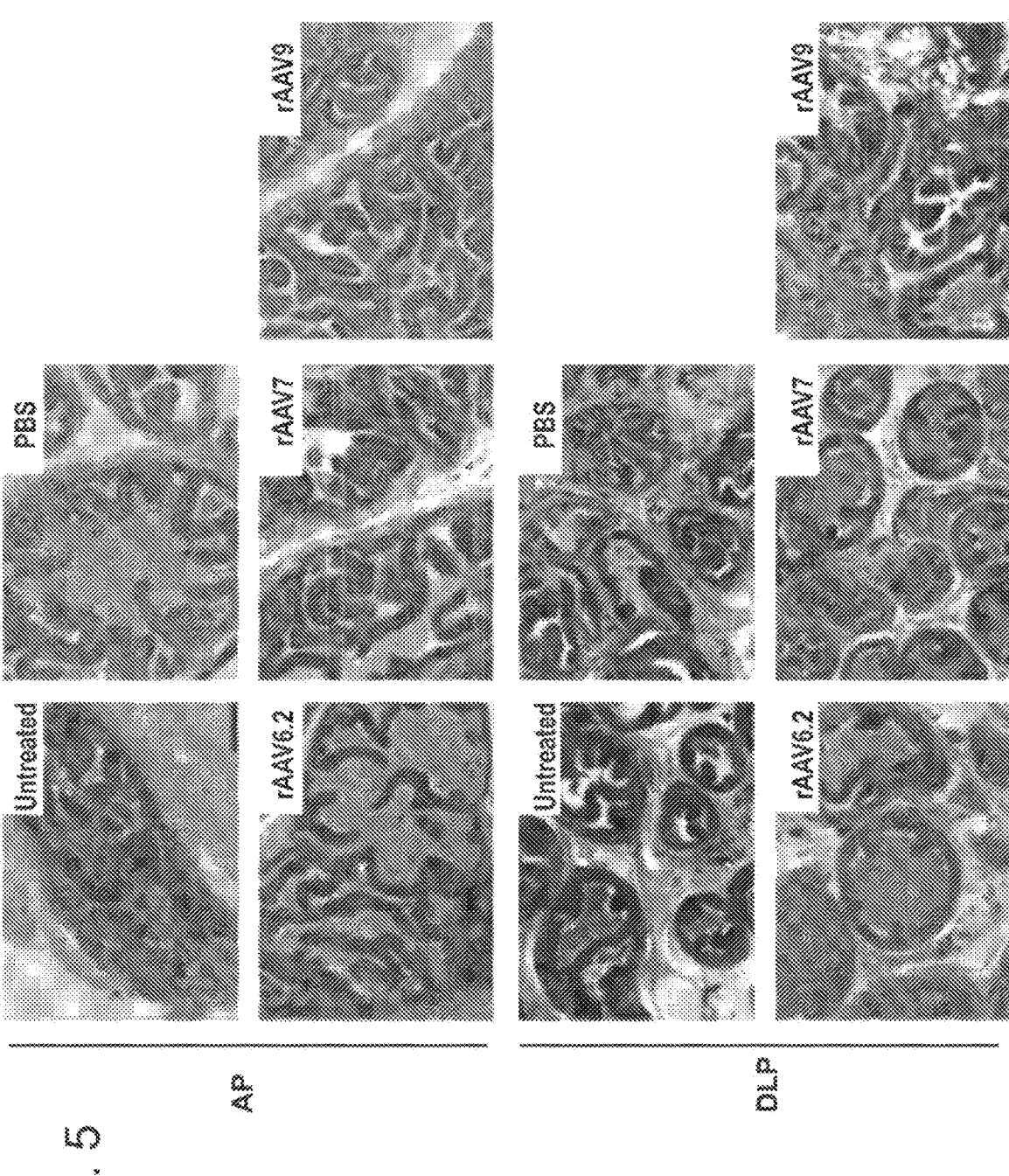
FIG. 5 shows intraprostate injection of rAAV vectors and transduction had no adverse effect on prostate histology. Representative H&E staining images of AP and DLP tissue sections collected from mice that were not treated (untreated), treated with PBS, or three rAAV serotype vectors including rAAV6.2, 7 and 9. Scale bars represent 100 microns.

Three weeks after injection. AP and DLP cryo-sections were subjected to fluorescence microscopy. It was found that rAAV6.2, rAAV7 and rAAV9 outperformed the other serotypes in transducing AP (FIGS. 2A-2B, FIG. 4A). Among these three serotypes, rAAV6.2 and rAAV7 also transduced DLP efficiently (FIGS. 3A-3B, FIG. 4A). In addition, rAAV5, rAAV8 and rAAVrh.10 transduced DLP (FIG. 3A, FIG. 4A). For the two leading serotypes that transduced both AP and DLP (rAAV6.2 and rAAV7), the vector genome biodistribution in the injected AP and DLP was determined to be approximately 10-20 rAAV genome copies per cell (FIG. 4B). Normal histology was observed by H&E staining in both AP and DLP, without indication of inflammation or other adverse effects following PBS or rAAV injection (FIG. 5). These results suggested that rAAV6.2 and rAAV7 are good candidates for efficient and safe delivery of genes of interest to mouse prostate in vivo.

To further characterize the prostatic cell types that were transduced with rAAV6.2 and rAAV7, immunofluorescence

45

Figure 6A:
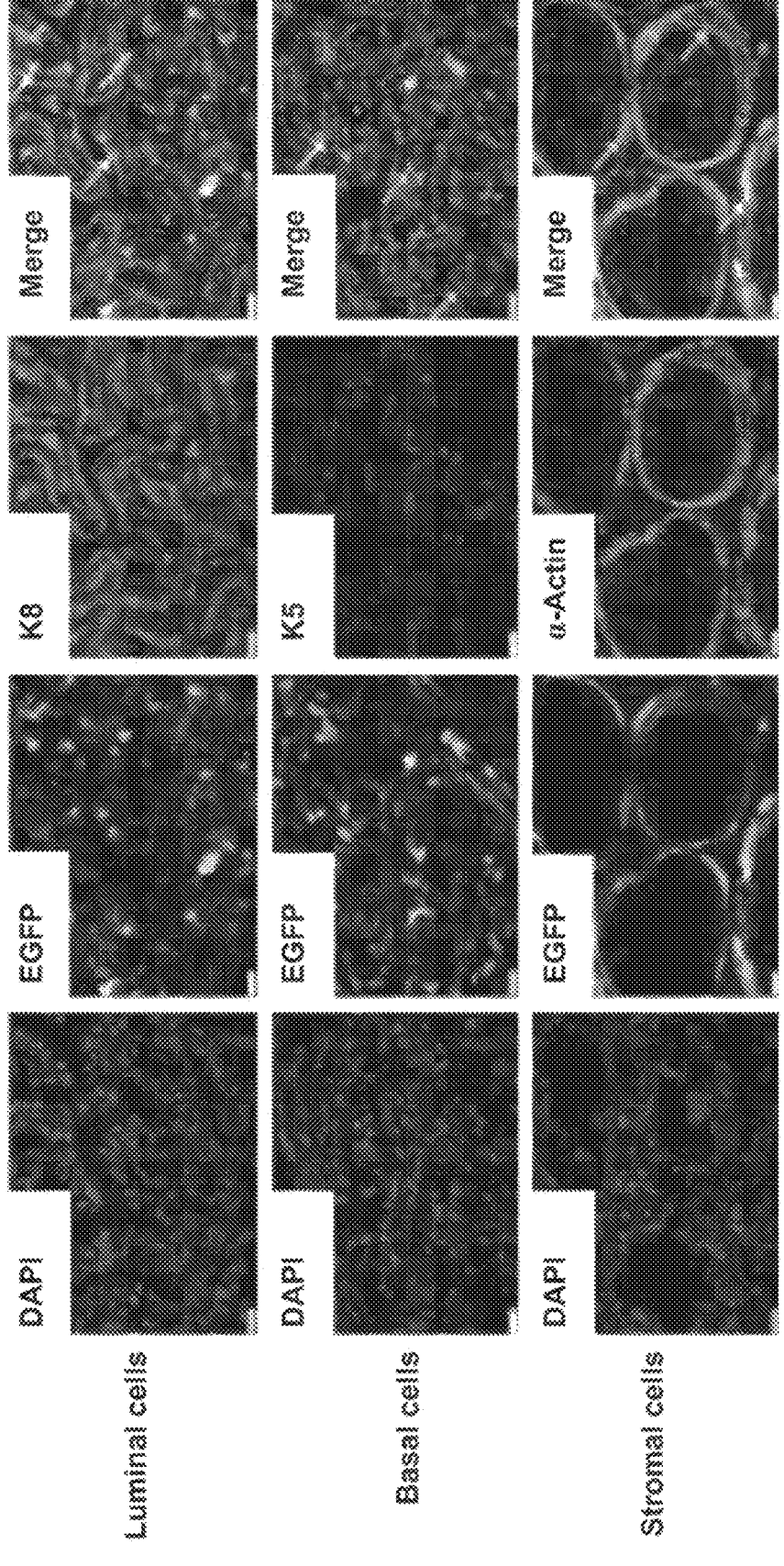
Figure 6B:
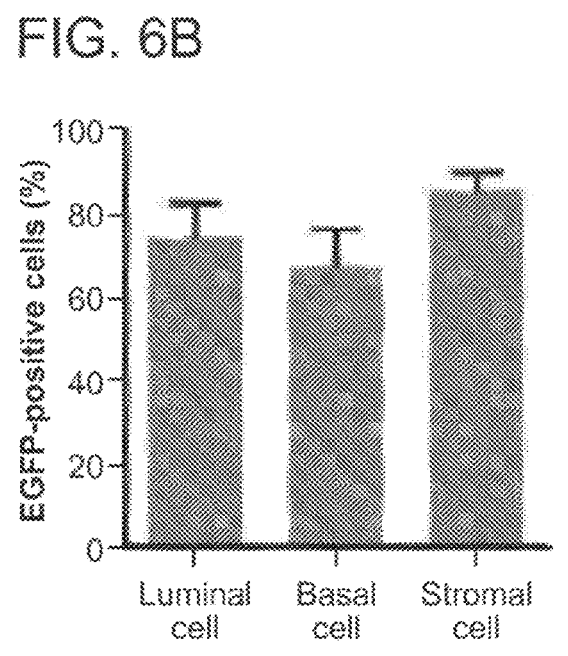

46 staining of mouse AP and DLP sections was performed with antibodies against cellular markers of major prostate cell types including luminal cells (K8), basal cells (K5) and stromal cells (α-actin for smooth muscle cells). It was found that both serotypes were able to transduce the majority of the three cell types in both AP and DLP. Representative fluorescence microscopic images are shown in FIG. 6A. Quantification of EGFP-positive cells of each cell type revealed that 65-80% of luminal cells, basal cells and stromal cells could be transduced (FIG. 6B).

Example 2. rAAV-Based and Intraprostatically Delivered miR-34a Therapeutics for Efficient Inhibition of Prostate Cancer Progression Prostate cancer (PCa) is the second most common diagnosed cancer and the fifth cause of cancer-related mortality for males worldwide. At present, there is no effective treatment for PCa. Towards further understanding molecular mechanism and developing therapeutics for PCa, the role of miR34a in PCa progression was investigated.

Expression of miR-34a is significantly downregulated in PCa cells. Here, downregulation of miR34a in prostate tumor from transgenic adenocarcinoma mouse prostate (TRAMP) model was examined. Relative expression of miR34a in prostate tissue of wild type and TRAMP mice was quantified by quantitative PCR (qPCR). Results demonstrate that expression of miR34a is significantly downregulated in the TRAMP mice (FIG. 7A). An rAAV-pri-miR34a construct was produced and tested using a luciferase assay. Results indicate that the rAAV-pir-miR34a construct efficiently downregulates expression of the reporter gene (e.g., luciferase) (FIG. 713) in vitro. Analysis by qPCR demonstrates that miR34a overexpression inhibits growth of prostate cancer cells (FIG. 8A). In particular, it was found that overexpression of miR-34a significantly inhibits the cell cycle of PC3 cells (FIG. 8B) by prolonging $G_1$ (FIG. 8C-8D) and shortening S phases through targeting cyclin D1 (CCND1), CD44, and DNA topoisomerase 2-alpha (TOP2A), as shown in FIG. 8E. It was also observed that miR34a overexpression reduces cell viability (FIGS. 9A-9B) and inhibits cell migration of PC3 cells as measured by a wound healing assay (FIG. 9C-9D).

To investigate if in vivo gene delivery of pri-miR34a to the prostates of TRAMP mice can inhibit PCa progression, 12 serotypes of rAAVs were screened for efficient prostate targeting in vivo and in PCa cells in vitro. Several candidate vectors (e.g., AAV6.2, AAV7 and AAV9) were identified. Intraprostatic injection of rAAV9-pri-miR34a ($4 \times 10^{11}$ GCs/prostate) to 8-week old TRAMP mice for inhibition of PCa progression was investigated. Treatment with rAAV7-miR34a lowered body weights significantly (p<0.05) as compared to the control group starting from 24 weeks after injection, likely a result of the higher tumor burden in the control group (FIG. 10A). rAAV7-miR34a treatment also significantly extended the lifespan of TRAMP mice (p<0.05) (FIG. 10B). Moreover, proliferation and neoplasia in the rAAV7-mir34a treated prostates were significantly diminished in both the anterior prostate (AP) and dorsal lateral prostate (DIY) when compared to those in the control group (FIG. 11).

Longevity of miR34a expression was also investigated. miRNA and reporter expression in mouse prostate were measured by qPCR and reporter (Gluc) assay 3 weeks post intraprostatic injection. Results indicate that miR34 expression is highly upregulated in treated mice versus control mice (FIG. 12A) and that miR34 expression persists for up to 52 weeks after injection (FIG. 12B). It was also observed that expression of Aldolase A, Fructose-Bisphosphate (ALDOA) and Sex Determining Region Y)-Box 4 (Sox4) were significantly downregulated in miR34a-treated mouse prostate compared to untreated control, mouse prostate (FIG. 12C). Relative protein expression results were confirmed by Western blot, which show miR34a overexpression downregulates ALDOA, Ccnd1, and Sox4 expression in mouse prostate (FIG. 13).

In sum, these results demonstrate the potential of rAAV-mediated efficient modulation of miRNA expression in the prostate for inhibiting PCa progression.

---

What is claimed is:

1. A method for delivering a transgene to prostate tissue, the method comprising:

administering to prostate tissue of a subject an effective amount of a recombinant adeno-associated virus (rAAV), wherein the rAAV comprises (i) a capsid protein having a serotype selected from the group consisting of AAV5, AAV6.2, AAV7, AAV8, AAV9, and AAVrh.10, and (ii) an isolated nucleic acid comprising a promoter operably linked to a transgene, wherein the rAAV infects cells of the prostate tissue.

2. The method of claim 1, wherein the capsid protein is AAV6.2 capsid protein or AAV7 capsid protein.

3. The method of claim 1, wherein the transgene encodes a gene associated with a prostate disease, wherein the prostate disease is selected from prostatitis, prostate cancer, and benign prostate hyperplasia (BPH).

4. The method of claim 3, wherein the gene encodes a gene selected from the group consisting of BCL-2, PTEN, SLC39A1, BRCA1, BRCA2, HPC1, RUNX2, CLCA2, YAP1, MASPIN, LL37, CDKN1B, AR, NKX3.1, CASP9, FKHR, GSK3, MDM2, ERK1/2, PSA, CCND1, ALDOA, Sox4, CD44, and miR34a.

5. The method of claim 1, wherein the administration occurs by injection, wherein:

i) the injection is not intraperitoneal (i.p.) injection; or ii) the injection is intraprostate injection.

6. The method of claim 1, wherein the rAAV further comprises two AAV inverted terminal repeats (ITRs), wherein the ITRs flank the transgene.

7. A method for treating a prostate disease, the method comprising: administering to a subject having or suspected of having a prostate disease an effective amount of rAAV, wherein the rAAV comprises (i) a capsid protein having a serotype selected from the group consisting of AAV5, AAV6.2, AAV7, AAV8, AAV9, and AAVrh.10, and (ii) an isolated nucleic acid comprising a promoter operably linked to a transgene, wherein the rAAV infects cells of the prostate tissue.

8. The method of claim 7, wherein the capsid protein is AAV6.2 capsid protein or AAV7 capsid protein.

9. The method of claim 7, wherein the transgene encodes a gene associated with a prostate disease, wherein the prostate disease is selected from prostatitis, prostate cancer, and benign prostate hyperplasia (BPH).

10. The method of claim 9, wherein the gene encodes a gene selected from the group consisting of BCL-2, PTEN, SLC39A1, BRCA1, BRCA2, HPC1, RUNX2, CLCA2, YAP1, MASPIN, LL37, CDKN1B, AR, NKX3.1, CASP9, FKHR, GSK3, MDM2, ERK1/2, PSA, CCND1, ALDOA, CD44, Sox4, and miR34a.

11. The method of claim 7, wherein the administration occurs by injection, wherein:

i) the injection is not intraperitoneal (i.p.); or ii) the injection is intraprostate injection.

12. The method of claim 7, wherein the administration results in transduction of a prostate cell type selected from the group consisting of luminal prostate cells, basal prostate cells, and stromal prostate cells.

13. The method of claim 7, wherein the rAAV further comprises two AAV inverted terminal repeats (ITRs), wherein the ITRs flank the transgene.

14. A method for treating a prostate disease, the method comprising:

administering to a subject having or suspected of having a prostate disease an effective amount of a recombinant adeno-associated virus (rAAV) comprising a capsid having a serotype selected from the group consisting of AAV5, AAV6.2, AAV7, AAV8, AAV9, and AAVrh.10, and an isolated nucleic acid comprising a promoter operably linked to a transgene, wherein the transgene encodes miR3a, and wherein the rAAV infects the cells of prostate tissue of the subject, and expresses the miR34a.

15. The method of claim 14, wherein the transgene:

i) comprises the sequence set forth in SEQ ID NO. 15 or 16; or ii) is flanked by adeno-associated virus inverted terminal repeats (AAV ITRs).

16. The method of claim 14, wherein the rAAV comprises an amino acid sequence that is at least 70%, at least 80%, at least 90%, at least 95%, or at least 99% identical to any one of SEQ ID NOs: 1 or 3-7.

17. The method of claim 14, wherein the administration occurs by injection, wherein:

i) the injection is not intraperitoneal (i.p.) injection; or ii) the injection is intraprostate injection.

* * * * *

SEQUENCE LISTING

```
Sequence total quantity: 16
SEQ ID NO: 1              moltype = AA  length = 724
FEATURE                   Location/Qualifiers
REGION                    1..724
                          note = Synthetic Polypeptide
source                    1..724
                          mol_type = protein
                          organism = synthetic construct
SEQUENCE: 1
MSFVDHPPDW LEEVGEGLRE FLGLEAGPPK PKPNQQHQDQ ARGLVLPGYN YLGPGNGLDR   60
GEPVNRADEV AREHDISYNE QLEAGDNPYL KYNHADAEFQ EKLADDTSFG GNLGKAVFQA  120
KKRVLEPFGL VEEGAKTAPT GKRIDDHFPK RKKARTEEDS KPSTSSDAEA GPSGSQQLQI  180
PAQPASSLGA DTMSAGGGGP LGDNNQGADG VGNASGDWHC DSTWMGDRVV TKSTRTWVLP  240
SYNNHQYREI KSGSVDGSNA NAYFGYSTPW GYFDFNRFHS HWSPRDWQRL INNYWGFRPR  300
SLRVKIFNIQ VKEVTVQDST TTIANNLTST VQVFTDDDYQ LPYVVGNGTE GCLPAFPPQV  360
FTLPQYGYAT LNRDNTENPT ERSSFFCLEY FPSKMLRTGN NFEFTYNFEE VPFHSSFAPS  420
QNLFKLANPL VDQYLYRFVS TNNTGGVQFN KNLAGRYANT YKNWFPGPMG RTQGWNLGSG  480
VNRASVSAFA TTNRMELEGA SYQVPPQPNG MTNNLQGSNT YALENTMIFN SQPANPGTTA  540
TYLEGNMLIT SESETQPVNR VAYNVGGQMA TNNQSSTTAP ATGTYNLQEI VPGSVWMERD  600
VYLQGPIWAK IPETGAHFHP SPAMGGFGLK HPPPMMLIKN TPVPGNITSF SDVPVSSFIT  660
QYSTGQVTVE MEWELKKENS KRWNPEIQYT NNYNDPQFVD FAPDSTGEYR TTRPIGTRYL  720
TRPL                                                              724

SEQ ID NO: 2              moltype = AA  length = 736
FEATURE                   Location/Qualifiers
REGION                    1..736
                          note = Synthetic Polypeptide
```

```
source                    1..736
                          mol_type = protein
                          organism = synthetic construct
SEQUENCE: 2
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPFG LVEEGAKTAP GKKRPVEQSP QEPDSSSGIG KTGQQPAKKR LNFGQTGDSE   180
SVPDPQPLGE PPATPAAVGP TTMASGGGAP MADNNEGADG VGNASGNWHC DSTWLGDRVI   240
TTSTRTWALP TYNNHLYKQI SSASTGASND NHYFGYSTPW GYFDFNRFHC HFSPRDWQRL   300
INNNWGFRPK RLNFKLFNIQ VKEVTTNDGV TTIANNLTST VQVFSDSEYQ LPYVLGSAHQ   360
GCLPPFPADV FMIPQYGYLT LNNGSQAVGR SSFYCLEYFP SQMLRTGNNF TFSYTFEDVP   420
FHSSYAHSQS LDRLMNPLID QYLYYLNRTQ NQSGSAQNKD LLFSRGSPAG MSVQPKNWLP   480
GPCYRQQRVS KTKTDNNNSN FTWTGASKYN LNGRESIINP GTAMASHKDD KDKFFPMSGV   540
MIFGKESAGA SNTALDNVMI TDEEEIKATN PVATERFGTV AVNLQSSSTD PATGDVHVMG   600
ALPGMVWQDR DVYLQGPIWA KIPHTDGHFH PSPLMGGFGL KHPPPQILIK NTPVPANPPA   660
EFSATKFASF ITQYSTGQVS VEIEWELQKE NSKRWNPEVQ YTSNYAKSAN VDFTVDNNGL   720
YTEPRPIGTR YLTRPL                                                    736

SEQ ID NO: 3               moltype = AA   length = 736
FEATURE                    Location/Qualifiers
REGION                     1..736
                           note = Synthetic Polypeptide
source                     1..736
                           mol_type = protein
                           organism = synthetic construct
SEQUENCE: 3
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPLG LVEEGAKTAP GKKRPVEQSP QEPDSSSGIG KTGQQPAKKR LNFGQTGDSE   180
SVPDPQPLGE PPATPAAVGP TTMASGGGAP MADNNEGADG VGNASGNWHC DSTWLGDRVI   240
TTSTRTWALP TYNNHLYKQI SSASTGASND NHYFGYSTPW GYFDFNRFHC HFSPRDWQRL   300
INNNWGFRPK RLNFKLFNIQ VKEVTTNDGV TTIANNLTST VQVFSDSEYQ LPYVLGSAHQ   360
GCLPPFPADV FMIPQYGYLT LNNGSQAVGR SSFYCLEYFP SQMLRTGNNF TFSYTFEDVP   420
FHSSYAHSQS LDRLMNPLID QYLYYLNRTQ NQSGSAQNKD LLFSRGSPAG MSVQPKNWLP   480
GPCYRQQRVS KTKTDNNNSN FTWTGASKYN LNGRESIINP GTAMASHKDD KDKFFPMSGV   540
MIFGKESAGA SNTALDNVMI TDEEEIKATN PVATERFGTV AVNLQSSSTD PATGDVHVMG   600
ALPGMVWQDR DVYLQGPIWA KIPHTDGHFH PSPLMGGFGL KHPPPQILIK NTPVPANPPA   660
EFSATKFASF ITQYSTGQVS VEIEWELQKE NSKRWNPEVQ YTSNYAKSAN VDFTVDNNGL   720
YTEPRPIGTR YLTRPL                                                    736

SEQ ID NO: 4               moltype = AA   length = 737
FEATURE                    Location/Qualifiers
REGION                     1..737
                           note = Synthetic Polypeptide
source                     1..737
                           mol_type = protein
                           organism = synthetic construct
SEQUENCE: 4
MAADGYLPDW LEDNLSEGIR EWWDLKPGAP KPKANQQKQD NGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPLG LVEEGAKTAP AKKRPVEPSP QRSPDSSTGI GKKGQQPARK RLNFGQTGDS   180
ESVPDPQPLG EPPAAPSSVG SGTVAAGGGA PMADNNEGAD GVGNASGNWH CDSTWLGDRV   240
ITTSTRTWAL PTYNNHLYKQ ISSETAGSTN DNTYFGYSTP WGYFDFNRFH CHFSPRDWQR   300
LINNNWGFRP KKLRFKLFNI QVKEVTTNDG VTTIANNLTS TIQVFSDSEY QLPYVLGSAH   360
QGCLPPFPAD VFMIPQYGYL TLNNGSQSVG RSSFYCLEYF PSQMLRTGNN FEFSYSFEDV   420
PFHSSYAHSQ SLDRLMNPLI DQYLYYLART QSNPGGTAGN RELQFYQGGP STMAEQAKNW   480
LPGPCFRQQR VSKTLDQNNN SNFAWTGATK YHLNGRNSLV NPGVAMATHK DDEDRFFPSS   540
GVLIFGKTGA TNKTTLENVL MTNEEEIRPT NPVATEEYGI VSSNLQAANT AAQTQVVNNQ   600
GALPGMVWQN RDVYLQGPIW AKIPHTDGNF HPSPLMGGFG LKHPPPQILI KNTPVPANPP   660
EVFTPAKFAS FITQYSTGQV SVEIEWELQK ENSKRWNPEI QYTSNFEKQT GVDFAVDSQG   720
VYSEPRPIGT RYLTRNL                                                   737

SEQ ID NO: 5               moltype = AA   length = 738
FEATURE                    Location/Qualifiers
REGION                     1..738
                           note = Synthetic Polypeptide
source                     1..738
                           mol_type = protein
                           organism = synthetic construct
SEQUENCE: 5
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTTTGQNNN SNFAWTAGTK YHLNGRNSLA NPGIAMATHK DDEERFFPSN   540
```

```
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                  738

SEQ ID NO: 6              moltype = AA  length = 736
FEATURE                   Location/Qualifiers
REGION                    1..736
                          note = Synthetic Polypeptide
source                    1..736
                          mol_type = protein
                          organism = synthetic construct
SEQUENCE: 6
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                    736

SEQ ID NO: 7              moltype = AA  length = 738
FEATURE                   Location/Qualifiers
REGION                    1..738
                          note = Synthetic Polypeptide
source                    1..738
                          mol_type = protein
                          organism = synthetic construct
SEQUENCE: 7
MAADGYLPDW LEDNLSEGIR EWWDLKPGAP KPKANQQKQD DGRGLVLPGY KYLGPFNGLD   60
KGEPVNAADA AALEHDKAYD QQLKAGDNPY LRYNHADAEF QERLQEDTSF GGNLGRAVFQ   120
AKKRVLEPLG LVEEGAKTAP GKKRPVEPSP QRSPDSSTGI GKKGQQPAKK RLNFGQTGDS   180
ESVPDPQPIG EPPAGPSGLG SGTMAAGGGA PMADNNEGAD GVGSSSGNWH CDSTWLGDRV   240
ITTSTRTWAL PTYNNHLYKQ ISNGTSGGST NDNTYFGYST PWGYFDFNRF HCHFSPRDWQ   300
RLINNNWGFR PKRLNFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFEFSYQFED   420
VPFHSSYAHS QSLDRLMNPL IDQYLYYLSR TQSTGGTAGT QQLLFSQAGP NNMSAQAKNW   480
LPGPCYRQQR VSTTLSQNNN SNFAWTGATK YHLNGRDSLV NPGVAMATHK DDEERFFPSS   540
GVLMFGKQGA GKDNVDYSSV MLTSEEEIKT TNPVATEQYG VVADNLQQQN AAPIVGAVNS   600
QGALPGMVWQ NRDVYLQGPI WAKIPHTDGN FHPSPLMGGF GLKHPPPQIL IKNTPVPADP   660
PTTFSQAKLA SFITQYSTGQ VSVEIEWELQ KENSKRWNPE IQYTSNYYKS TNVDFAVNTD   720
GTYSEPRPIG TRYLTRNL                                                  738

SEQ ID NO: 8              moltype = DNA  length = 2172
FEATURE                   Location/Qualifiers
misc_feature             1..2172
                          note = Synthetic Polynucleotide
source                    1..2172
                          mol_type = other DNA
                          organism = synthetic construct
SEQUENCE: 8
atgtcttttg ttgatcaccc tccagattgg ttggaagaag ttggtgaagg tcttcgcgag   60
tttttgggcc ttgaagcggg cccaccgaaa ccaaaaccca atcagcagca tcaagatcaa   120
gcccgtggtc ttgtgctgcc tggttataac tatctcggac ccggaaacgg tctcgatcga   180
ggagagcctg tcaacagggc agacgaggtc gcgcgagagc acgacatctc gtacaacgag   240
cagcttgagg cgggagacaa ccctacctc aagtacaacc acgcggacgc cgagtttcag   300
gagaagctcg ccgacgacac atccttcggg ggaaacctcg gaaaggcagt ctttcaggcc   360
aagaaaaggg ttctcgaacc ttttggcctg gttgaagagg gtgctaagac ggccccctacc   420
ggaaagcgga tagacgacca ctttccaaaa agaaagaagg cccggaccga agaggactcc   480
aagccttcca cctcgtcaga cgccgaagct ggacccagcg gatcccagca gctgcaaatc   540
ccagcccaac cagcctcaag tttgggagct gatacaatgt ctgcgggagg tggcggccca   600
ttgggcgaca ataaccaagg tgccgatgga gtgggcaatg cctcgggaga ttggcattgc   660
gattccacgt ggatggggga cagagtcgtc accaagtcca cccgaacctg ggtgctgccc   720
agctacaaca accaccagta ccgagagatc aaaagcggct ccgtcgacgg aagcaacgcc   780
aacgcctact ttgatacag cacccccctgg gggtactttg actttaaccg cttccacagc   840
cactggagcc cccgagactg gcaaagactc atcaacaact actgggggctt cagacccgg   900
tccctcagag tcaaaatctt caacattcaa gtcaaagagg tcacggtgca ggactccacc   960
accaccgtcg ccaacaacct cacctccacc gtccaagtgt tacggacga cgattaccag   1020
ctgccctacg tcgtcggcaa cgggaccgag ggatgcctgc cggccttccc tccgcaggtc   1080
tttacgctgc cgcagtacgg ttacgcgacg ctgaaccgcg acaacacaga aaatcccacc   1140
gagaggagca gcttcttctg cctagagtac tttcccagca gatgctgag aacgggcaac   1200
aactttgagt ttacctacaa ctttgaggag gtgcccttcc actccagctt cgctcccagt   1260
cagaacctct tcaagctggc caaccgctg gtggaccagt acttgtaccg cttcgtgagc   1320
```

-continued

```
acaaataaca ctggcggagt ccagttcaac aagaacctgg ccgggagata cgccaacacc  1380
tacaaaaact ggttcccggg gcccatgggc cgaacccagg gctggaacct gggctccggg  1440
gtcaaccgcg ccagtgtcag cgccttcgcc acgaccaata ggatggagct cgagggcgcg  1500
agttaccagg tgcccccgca gccgaacggc atgaccaaca acctccaggg cagcaacacc  1560
tatgccctgg agaacactat gatcttcaac agccagccgg cgaacccggg caccaccgcc  1620
acgtacctcg agggcaacat gctcatcacc agcgagagcg agacgcagcc ggtgaaccgc  1680
gtggcgtaca acgtcggcgg gcagatggcc accaacaacc agagctccac cactgcccc  1740
gcgaccggca cgtacaacct ccaggaaatc gtgcccggca gcgtgtggat ggagagggac  1800
gtgtacctcc aaggacccat ctgggccaag atcccagaga cggggcgca ctttcacccc  1860
tctccggcca tgggcggatt cggactcaaa cacccaccgc ccatgatgct catcaagaac  1920
acgcctgtgc ccggaaatat caccagcttc tcggacgtgc ccgtcagcag cttcatcacc  1980
cagtacagca ccgggcaggt caccgtggag atggagtggg agctcaagaa ggaaaactcc  2040
aagaggtgga acccagagat ccagtacaca aacaactaca acgacccca gtttgtggac  2100
tttgcccgg acagcaccgg ggaatacaga accaccagac ctatcggaac ccgatacctt  2160
acccgacccc tt                                                        2172

SEQ ID NO: 9              moltype = DNA  length = 2208
FEATURE                  Location/Qualifiers
misc_feature            1..2208
                         note = Synthetic Polynucleotide
source                   1..2208
                         mol_type = other DNA
                         organism = synthetic construct
SEQUENCE: 9
atggctgccg atggttatct tccagattgg ctcgaggaca acctctctga gggcattcgc  60
gagtggtggg acttgaaacc tggagccccg aaacccaaag ccaaccagca aaagcaggac  120
gacggccggg gtctggtgct tcctggctac aagtacctcg gacccttcaa cggactcgac  180
aagggggagc ccgtcaacgc ggcggatgca gcggccctcg agcacgacaa ggcctacgac  240
cagcagctca aagcgggtga caatccgtac ctgcggtata accacgccga cgccgagttt  300
caggacgtc tgcaagaaga tacgtctttt ggggcaacc tcgggcgagc agtcttccag  360
gccaagaaga gggttctcga acctttggt ctggttgagg aaggtgctaa gacggctcct  420
ggaaagaaac gtccggtaga gcagtcgcca caagagccag actcctcctc gggcattggc  480
aagacaggcc agcagcccgc taaaaagaga ctcaattttg gtcagactgg cgactcagag  540
tcagtcccc acccacaacc tctcggagaa cctccagcaa cccccgctgc tgtgggacct  600
actacaatgg cttcaggcgg tggcgcacca atggcagaca ataacgaagg cgccgacgga  660
gtgggtaatg cctcaggaaa ttggcattgc gattccacat ggctgggcga cagagtcatc  720
accaccagca cccgaacatg ggccttgccc acctataaca accacctcta caagcaaatc  780
tccagtgctt caacggggc cagcaacgac aaccactact tcggctacag caccccctgg  840
gggtatttg atttcaacag attccactgc catttctcac cacgtgactg gcagcgactc  900
atcaacaaca attggggatt ccggcccaag agactcaact tcaagctctt caacatccaa  960
gtcaaggagg tcacgacgaa tgatggcgtc acgaccatcg ctaataacct taccagcacg  1020
gttcaagtct tctcggactc ggagtaccag ttgccgtacg tcctcggctc tgcgcaccag  1080
ggctgcctcc ctccgttccc ggcggacgtg ttcatgatc cgcagtacgg ctacctaacg  1140
ctcaacaatg gcagccaggc agtgggacgg tcatcctttt actgcctgga atatttccca  1200
tcgcagatgc tgagaacggg caataacttt accttcagct cacccttcga ggacgtgcct  1260
ttccacagca gctacgcgca cagccagagc ctggaccggc tgatgaatcc tctcatcgac  1320
cagtacctgt attacctgaa cagaactcag aatcagtccg gaagtgccca aaacaaggac  1380
ttgctgttta gccgggggtc tccagctggc atgtctgttc agcccaaaaa ctggctacct  1440
ggaccctgtt accgggcagca gcgcgtttct aaaacaaaaa cagacaacaa caacagcaac  1500
tttacctgga ctggtgcttc aaaatataac cttaatgggc gtgaatctat aatcaaccct  1560
ggcactgcta tggcctcaca caaagacgac aaagacaagt tctttcccat gagcggtgtc  1620
atgatttttg gaaaggagag cgccggagct tcaaacactg cattggacaa tgtcatgatc  1680
acagacgaag aggaaatcaa agccactaac cccgtggcca ccgaaagatt tgggactgtg  1740
gcagtcaatc tccagagcag cagcacagac cctgcgaccg gagatgtgca tgttatggga  1800
gccttacctg gaatggtgtg gcaagacaga gacgtatacc tgcagggtcc tatttgggcc  1860
aaaattcctc acacggatgg acactttcac ccgtctcctc tcatgggcgg ctttggactt  1920
aagcacccgc ctcctcagat cctcatcaaa aacacgcctg ttcctgcgaa tcctccggca  1980
gagttttcg ctacaaagtt tgcttcattc atcacccagt attccacagg acaagtgagc  2040
gtggagattg aatgggagct gcagaaagaa aacagcaaac gctggaatcc cgaagtgcag  2100
tatacatcta actatgcaaa atctgccaac gttgatttca ctgtggacaa caatggactt  2160
tatactgagc ctcgcccat tggcaccgt tacctaccg gtccctg              2208

SEQ ID NO: 10             moltype = DNA  length = 2208
FEATURE                  Location/Qualifiers
misc_feature            1..2208
                         note = Synthetic Polynucleotide
source                   1..2208
                         mol_type = other DNA
                         organism = synthetic construct
SEQUENCE: 10
atggctgccg atggttatct tccagattgg ctcgaggaca acctctctga gggcattcgc  60
gagtggtggg acttgaaacc tggagccccg aaacccaaag ccaaccagca aaagcaggac  120
gacggccggg gtctggtgct tcctggctac aagtacctcg gacccttcaa cggactcgac  180
aagggggagc ccgtcaacgc ggcggatgca gcggccctcg agcacgacaa ggcctacgac  240
cagcagctca aagcgggtga caatccgtac ctgcggtata accacgccga cgccgagttt  300
caggagcgtc tgcaagaaga tacgtctttt ggggcaacc tcgggcgagc agtcttccag  360
gccaagaaga gggttctcga acctcttggt ctggttgagg aaggtgctaa gacggctcct  420
ggaaagaaac gtccggtaga gcagtcgcca caagagccag actcctcctc gggcattggc  480
aagacaggcc agcagcccgc taaaaagaga ctcaattttg gtcagactgg cgactcagag  540
```

-continued

```
tcagtccccg acccacaacc tctcggagaa cctccagcaa cccccgctgc tgtgggacct   600
actacaatgg cttcaggcgg tggcgcacca atggcagaca ataacgaagg cgccgacgga   660
gtgggtaatg cctcaggaaa ttggcattgc gattccacat ggctgggcga cagagtcatc   720
accaccagca cccgaacatg ggccttgccc acctataaca accacctcta caagcaaatc   780
tccagtgctt caacggggc cagcaacgac aaccactact tcggctacag cacccctgg   840
gggtattttg atttcaacag attccactgc catttctcac cacgtgactg gcagcgactc   900
atcaacaaca attggggatt ccggcccaag agactcaact tcaagctctt caacatccaa   960
gtcaaggagg tcacgacgaa tgatggcgtc acgaccatcg ctaataacct taccagcacg  1020
gttcaagtct tctcggactc ggagtaccag ttgccgtacg tcctcggctc tgcgcaccag  1080
ggctgcctcc ctccgttccc ggcggacgtg ttcatgattc cgcagtacgg ctacctaacg  1140
ctcaacaatg gcagccaggc agtgggacgg tcatcctttt actgcctgga atatttccca  1200
tcgcagatgc tgagaacggg caataacttt accttcagct acaccttcga ggacgtgcct  1260
ttccacagca gctacgcgca cagccagagc ctggaccggc tgatgaatcc tctcatcgac  1320
cagtacctgt attacctgaa cagaactcag aatcagtccg gaagtgccca aaacaaggac  1380
ttgctgttta gccgggggtc tccagctggc atgtctgttc agcccaaaaa ctggctacct  1440
ggaccctgtt accggcagca gcgcgtttct aaaacaaaaa cagacaacaa caacagcaac  1500
tttacctgga ctggtgcttc aaaatataac cttaatgggc gtgaatctat aatcaaccct  1560
ggcactgcta tggcctcaca caaagacgac aaagacaagt tctttcccat gacgggtgtc  1620
atgattttg gaaaggagag cgccggagct tcaaacactg cattggacaa tgtcatgatc  1680
acagacgaag aggaaatcaa agccactaac cccgtggcca ccgaaagatt tgggactgtg  1740
gcagtcaatc tccagagcag cagcacagac cctgcgaccg gagatgtgca tgttatggga  1800
gccttacctg gaatggtgtg gcaagacaga gacgtatacc tgcagggtcc tatttgggcc  1860
aaaattcctc acacggatgg acactttcac ccgtctcctc tcatgggcgg ctttggactt  1920
aagcacccgc ctcctcagat cctcatcaaa aacacgcctg ttcctgcgaa tcctccggca  1980
gagttttcgg ctacaaagtt tgcttcattc atcacccagt attccacagg acaagtgagc  2040
gtggagattg aatgggagct gcagaaagaa aacagcaagt gctggaatcc cgaagtgcag  2100
tatacatcta actatgcaaa atctgccaac gttgatttca ctgtggacaa caatggactt  2160
tatactgagc ctcgccccat tggcaccgt taccctcaccc gtccctg          2208
```

```
SEQ ID NO: 11        moltype = DNA  length = 2211
FEATURE              Location/Qualifiers
misc_feature        1..2211
                    note = Synthetic Polynucleotide
source              1..2211
                    mol_type = other DNA
                    organism = synthetic construct
SEQUENCE: 11
atggctgccg atggttatct tccagattgg ctcgaggaca acctctctga gggcattcgc   60
gagtggtggg acctgaaacc tggagccccg aaacccaaag ccaaccagca aaagcaggac  120
aacggccggg gtctggtgct tcctggctac aagtacctcg gacccttcaa cggactcgac  180
aagggggagc ccgtcaacgc ggcggacgca gcggccctcg agcacgacaa ggcctacgac  240
cagcagctca aagcgggtga caatccgtac ctgcggtata accacgccga cgccgagttt  300
caggacggtc tgcaagaaga tacgtcattt gggggcacgc tcgggcgagc agtcttccag  360
gccaagaagc gggttctcga acctctcggt ctggttgagg aaggcgctaa gacggctcct  420
gcaaagaaga gaccggtaga gccgtcacct cagcgttccc ccgactcctc cacgggcatc  480
ggcaagaaag gccagcagcc cgccagaaag agactcaatt cggtcagac tggcgactca  540
gagtcagtcc ccgaccctca acctctcgga gaacctccag cgccctc tagtgtggga  600
tctggtacag tggctgcagg cggtggcgca ccaatggcag acaataacga aggtgccgac  660
ggagtgggta atgcctcagg aaattggcat tgcgattcca catggctggg cgacagagtc  720
attaccacca gcacccgaac ctgggccctg cccacctaca caaccacct ctacaagcaa  780
atctccagtg aaactgcagg tagtaccaac gacaacacct acttcggcta cagcacccgc  840
tggggggtatt ttgactttaa cagattccac tgccacttct caccacgtga ctggcagcga  900
ctcatcaaca caactggggg attccggccc aagaagctgc ggttcaagct cttcaacatc  960
caggtcaagg aggtcacgac gaatgacggc gttacgacca tcgctaataa ccttaccagc  1020
acgattcagg tattctcgga ctcggaatac cagctgccga cgctcctcga ctctgcgcac  1080
cagggctgcc tgcctccgtt cccggcggac gtcttcatga ttcctcagta cggctacctg  1140
actctcaaca atggcagtca gtctgtggga cgttcctcct ctactgcct ggagtacttc  1200
ccctctcaga tgctgagaac gggcaacaac tttgagttca gctacagctt cgaggacgtg  1260
cctttccaca gcagctacgc acacagccag agcctggacc ggctgatgaa tccctctcat  1320
gaccagtact tgtactacct ggccagaaca cagagtaacc caggaggcac agctggcaat  1380
cgggaactgc agtttaccag gggcgggcct tcaactatgg ccgaacaagc caagaattgg  1440
ttacctggac cttgcttccg gcaacaaaga gtctccaaaa cgctggatca aaacaacaac  1500
agcaactttg cttggactgg tgccaccaaa tatcacctga acggcagaaa ctcgttggtt  1560
aatcccggcg tcgccatggc aactcacaag gacgacgagg acgctttttt cccatccagc  1620
ggagtcctga tttttggaaa aactggagca actaacaaaa ctacattgga aaatgtgtta  1680
atgacaaatg aagaagaaat tcgtcctact aatcctgtag ccacggaaga atacgggata  1740
gtcagcagca acttacaagc ggctaatact gcagcccaga cacaagttgt caacaaccag  1800
ggagccttac ctggcatggt ctggcagaac cgggacgtgt acctgcaggg tcccatctgg  1860
gccaagattc ctcacacgga tggcaacttt caccctctt cttgatggg cggctttctg  1920
cttaaacatc cgcctcctca gatcctgatc aagaacactc cgttcccgc taatcctccg  1980
gaggtgttta ctcctgccaa gtttgcttcg ttcatcacac agtacagcac cggacaagtc  2040
agcgtggaaa tcgagtggga gctgcagaag gaaaacagca gcgctggaa cccggagatt  2100
cagtacacct ccaactttga aaagcagact ggtgtggact ttgccgttga cagccagggt  2160
gtttactctg agcctcgccc tattggcact cgttacctca cccgtaatct g          2211
```

```
SEQ ID NO: 12        moltype = DNA  length = 2214
FEATURE              Location/Qualifiers
misc_feature        1..2214
                    note = Synthetic Polynucleotide
```

-continued

```
source                  1..2214
                        mol_type = other DNA
                        organism = synthetic construct
SEQUENCE: 12
atggctgccg atggttatct tccagattgg ctcgaggaca acctctctga gggcattcgc  60
gagtggtggg cgctgaaacc tggagccccg aagcccaaag ccaaccagca aaagcaggac  120
gacggccggg gtctggtgct tcctggctac aagtacctcg gacccttcaa cggactcgac  180
aaggggggagc ccgtcaacgc ggcggacgca gcggccctcg agcacgacaa ggcctacgac  240
cagcagctgc aggcgggtga caatccgtac ctgcggtata accacgccga cgccgagttt  300
caggagcgtc tgcaagaaga tacgtctttt gggggcaacc tcgggcgagc agtcttccag  360
gccaagaagc gggttctcga acctctcggt ctggttgagg aaggcgctaa gacggctcct  420
ggaaagaaga gaccggtaga gccatcaccc cagcgttctc cagactcctc tacgggcatc  480
ggcaagaaag gccaacagcc cgccagaaaa agactcaatt ttggtcagac tggcgactca  540
gagtcagttc cagaccctca acctctcgga gaacctccag cagcgccctc tggtgtggga  600
cctaatacaa tggctgcagg cggtggcgca ccaatggcag acaataacga aggcgccgac  660
ggagtgggta gttcctcggg aaattggcat tgcgattcca catggctggg cgacagagtc  720
atcaccacca gcacccgaac ctgggccctg cccacctaca acaaccacct ctacaagcaa  780
atctccaacg ggacatcggg aggagccacc aacgacaaca cctacttcgg ctacagcacc  840
ccctgggggt attttgactt taacagattc cactgccact tttcaccacg tgactggcag  900
cgactcatca acaacaactg gggattccgg cccaagagac tcagcttcaa gctcttcaac  960
atccaggtca aggaggtcac gcagaatgaa ggcaccaaga ccatcgccaa taacctcacc  1020
agcaccatcc aggtgtttac ggactcggag taccagctgc cgtacgttct cggctctgcc  1080
caccagggct gcctgcctcc gttcccggcg gacgtgttca tgattcccca gtacggctac  1140
ctaacactca acaacggtag tcaggccgtg ggacgctcct ccttctactg cctggaatac  1200
tttccttcgc agatgctgag aaccggcaac aacttccagt ttacttacac cttcgaggac  1260
gtgcctttcc acagcagcta cgcccacagc cagagcttgg accggctgat gaatcctctg  1320
attgaccagt acctgtacta cttgtctcgg actcaaacaa caggaggcac ggcaaatacg  1380
cagactctgg gcttcagcca aggtgggcct aatacaatgg ccaatcaggc aaagaactgg  1440
ctgccaggac cctgttaccg ccaacaacgc gtctcaacga caaccgggca aaacaacaat  1500
agcaactttg cctggactgc tgggaccaaa taccatctga atggaagaaa ttcattggct  1560
aatcctggca tcgctatggc aacacacaaa gacgacgagg agcgtttttt tcccagtaac  1620
gggatcctga tttttggcaa acaaaatgct gccagagaca atgcggatta cagcgatgtc  1680
atgctcacca gcgaggaaga aatcaaaacc actaaccctg tggctacaga ggaatacggt  1740
atcgtggcag ataacttgca gcagcaaaac acggctcctc aaattggaac tgtcaacagc  1800
caggggggcct tacccggtat ggtctggcag aaccgggacg tgtacctgca gggtcccatc  1860
tgggccaaga ttcctcacac ggacggcaac ttccacccgt ctccgctgat gggcggcttt  1920
ggcctgaaac atcctccgcc tcagatcctg atcaagaaca cgcctgtacc tgcggatcct  1980
ccgaccacct tcaaccagtc aaagctgaac tctttcatca cgcaatacag caccggacag  2040
gtcagcgtgg aaattgaatg ggagctgcag aaggaaaaca gcaagcgctg gaaccccgag  2100
atccagtaca cctccaacta ctacaaatct acaagtgtgg actttgctgt taatacagaa  2160
ggcgtgtact ctgaaccccg ccccattggc acccgttacc tcacccgtaa tctg  2214

SEQ ID NO: 13         moltype = DNA   length = 2208
FEATURE               Location/Qualifiers
misc_feature          1..2208
                      note = Synthetic Polynucleotide
source                1..2208
                      mol_type = other DNA
                      organism = synthetic construct
SEQUENCE: 13
atggctgccg atggttatct tccagattgg ctcgaggaca accttagtga aggaattcgc  60
gagtggtggg ctttgaaacc tggagccccct caacccaagg caaatcaaca acatcaagac  120
aacgctcgag gtcttgtgct tccgggttac aaataccttg gacccggcaa cggactcgac  180
aaggggggagc cggtcaacgc agcagacgcg gcggccctcg agcacgacaa ggcctacgac  240
cagcagctca aggccggaga caacccgtac ctcaagtaca accacgccga cgccgagttt  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctggggga cagagtcatc  720
accaccagca cccgaacctg ggccctgccc acctacaaca tcacctcta caagcaaatc  780
tccaacagca catctggagg atcttcaaat gacaacgcct acttcggctca cagcaccccc  840
tgggggtatt ttgacttcaa cagattccac tgccacttct caccacgtga ctggcagcga  900
ctcatcaaca caactggggg attccggcct aagcgactca acttcaagct cttcaacatt  960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgaaacgta  1260
cctttccata gcagctacgc tcacagccaa gcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctggcc agggaagaaa ctacatacct  1440
ggacccagct accgacaaca acgtgtctca accactgtga ctcaaaacaa caacagcgaa  1500
tttgcttggc ctggagcttc ttcttggct ctcaatggac gtaatagctt gatgaatcct  1560
ggacctgcta tggccagcca caagaagga gaggaccgtt tctttccttt gtctggatct  1620
ttaattttg gcaaacaagg aactggaaga gacaacgtgg atgcggacaa agtcatgata  1680
accaacgaag aagaaattaa aactactaac ccggtagcaa cggagtccta tggacaagtg  1740
```

```
gccacaaacc accagagtgc ccaagcacag gcgcagaccg gctgggttca aaaccaagga    1800
atacttccgg gtatggtttg gcaggacaga gatgtgtacc tgcaaggacc catttgggcc    1860
aaaattcctc acacggacgg caactttcac ccttctccgc tgatgggagg gtttggaatg    1920
aagcacccgc ctcctcagat cctcatcaaa aacacacctg tacctgcgga tcctccaacg    1980
gccttcaaca aggacaagct gaactctttc atcacccagt attctactgg ccaagtcagc    2040
gtggagatcg agtgggagct gcagaaggaa aacagcaagc gctggaaccc ggagatccag    2100
tacacttcca actattacaa gtctaataat gttgaatttg ctgttaatac tgaaggtgta    2160
tatagtgaac cccgccccat tggcaccaga tacctgactc gtaatctg               2208

SEQ ID NO: 14           moltype = DNA  length = 2258
FEATURE                 Location/Qualifiers
misc_feature            1..2258
                        note = Synthetic Polynucleotide
source                  1..2258
                        mol_type = other DNA
                        organism = synthetic construct
SEQUENCE: 14
tcgaggacaa cctctctgag ggcattcgcg agtggtggga cttgaaacct ggagccccga    60
aacccaaagc caaccagcaa aagcaggacg acggccgggg tctggtgctt cctggctaca    120
agtacctcgg acccttcaac ggactcgaca aggggggagcc cgtcaacgcg gcggacgcag    180
cggccctcga gcacgacaag gcctacgacc agcagctcaa agcgggtgac aatccgtacc    240
tgcggtataa ccacgccgac gccgagtttc aggagcgtct gcaagaagat acgtcttttg    300
ggggcaacct cgggcgagca gtcttccagg ccaagaagcg ggttctcgaa cctctcggtc    360
tggttgagga aggcgctaag acggctcctg gaaagaagag accggtagag ccatcacccc    420
agcgttctcc agactcctct acgggcatcg gcaagaaagg ccagcagccc gcgaaaaaga    480
gactcaactt tgggcagact ggcgactcag agtcagtgcc cgaccctcaa ccaatcgggg    540
aacccccgc aggcccctct ggtctgggat ctggtacaat ggctgcaggc ggtggcgctc    600
caatggcaga caataacgaa ggcgccgacg gagtgggtag ttcctcagga aattggcatt    660
gcgattccac atggctgggc gacagagtca tcaccaccag cacccgaacc tgggccctcc    720
ccacctacaa caaccacctc tacaagcaaa tctccaacg gacttcggga ggaagcacca    780
acgacaacac ctacttcggc tacagcaccc cctgggggta ttttgacttt aacagattcc    840
actgccactt ctcaccacgt gactggcagc gactcatcaa caacaactgg ggattccggc    900
ccaagagact caacttcaag ctcttcaaca tccaggtcaa ggaggtcacg cagaatgaag    960
gcaccaagac catcgccaat aaccttacca gcacgattca ggtctttacg gactcggaat    1020
accagctccc gtacgtcctc ggctctgcgc accagggctg cctgcctccg ttcccggcgg    1080
acgtcttcat gattcctcag tacgggtacc tgactctgaa caatggcagt caggccgtgg    1140
gccgttcctc cttctactgc ctggagtact ttccttctca aatgctgaga acgggcaaca    1200
actttgagtt cagctaccag tttgaggacg tgcctttca cagcagctac gcgcacagcc    1260
aaagcctgga ccggctgatg aacccccctca tcgaccagta cctgtactac ctgtctcgga    1320
ctcagtccac gggaggtacc gcaggaactc agcagttgct attttctcag gccgggccta    1380
ataacatgtc ggctcaggcc aaaaactggc tacccgggcc ctgctaccgg cagcaacgcg    1440
tctccacgac actgtcgcaa aataacaaca gcaactttgc ctggaccggt gccaccaagt    1500
atcatctgaa tggcagagac tctctggtaa atcccggtgt cgctatggca acccacaagg    1560
acgacgaaga gcgatttttt ccgtccagcg gagtcttaat gtttgggaaa cagggagctg    1620
gaaaagacaa cgtggactat agcagcgtta tgctaaccag tgaggaagaa attaaaacca    1680
ccaacccagt ggccacagaa cagtacggcg tggtggccga taacctgcaa cagcaaaacg    1740
ccgctcctat tgtaggggcc gtcaacagtc aaggagcctt acctggcatg gtctggcaga    1800
accgggacgt gtacctgcag ggtcctatct gggccaagat tcctcacacg gacggaaact    1860
ttcatccctc gccgctgatg ggaggctttg gactgaaaca cccgcctcct cagatcctga    1920
ttaagaatac aacctgttcc gcggatcctc caactacctt cagtcaagct aagctggcgt    1980
cgttcatcac gcagtacagc accggacagg tcagcgtgga aattgaatgg gagctgcaga    2040
aagaaaacag caaacgctgg aacccagaga ttcaatacac ttccaactac tacaaatcta    2100
caaatgtgga ctttgctgtt aacacagatg gcacttattc tgagcctcgc cccatcggca    2160
cccgttacct cacccgtaat ctgtaattgc ttgttaatca ataaaccggt tgattcgttt    2220
cagttgaact ttggtctctg cgaagggcga attcgttt                          2258

SEQ ID NO: 15           moltype = DNA  length = 321
FEATURE                 Location/Qualifiers
misc_feature            1..321
                        note = Synthetic Polynucleotide
source                  1..321
                        mol_type = other DNA
                        organism = synthetic construct
SEQUENCE: 15
aggaattctg ctggaggagt gtgtcatacc tcggtagggt ccactacaca tctttctccc    60
gcagcctctc catcttcctg tgactgcggg cgcctcagcc tgggctggcc agctgtgagt    120
aattctttgg cagtgtctta gctggttgtt gtgagtatta gctaaggaag caatcagcaa    180
gtatactgcc ctagaagtgc tgcacattgt tgggccgaga aggaaaaggt cagaggtcag    240
caacgcccac acccctgaga ggcgctggac ttgcggagct gctcgaccat actggtgggt    300
atgggatggc ggccgcgtcc c                                            321

SEQ ID NO: 16           moltype = DNA  length = 2227
FEATURE                 Location/Qualifiers
misc_feature            1..2227
                        note = Synthetic Polynucleotide
source                  1..2227
                        mol_type = other DNA
                        organism = synthetic construct
SEQUENCE: 16
```

-continued

```
ctgcgcgctc gctcgctcac tgaggccgcc cgggcaaagc ccgggcgtcg ggcgaccttt   60
ggtcgcccgg cctcagtgag cgagcgagcg cgcagagagg gagtgtagcc atgctctagg   120
aagatcaatt cggtacaatt cacgcgtcga cattgattat tgactctggt cgttacataa   180
cttacggtaa atggcccgcc tggctgaccg cccaacgacc ccgcccattg acgtcaataa   240
tgacgtatgt tcccatagta acgccaatag ggactttcca ttgacgtcaa tgggtggagt   300
atttacggta aactgcccac ttggcagtac atcaagtgta tcatatgcca agtacgcccc   360
ctattgacgt caatgacggt aaatggcccg cctggcatta tgcccagtac atgaccttat   420
gggactttcc tacttggcag tacatctact cgaggccacg ttctgcttca ctctccccat   480
ctccccccc tccccacccc caattttgta tttatttatt ttttaattat tttgtgcagc   540
gatggggcg gggggggggg gggggggggc gcgcgccagg cggggcgggg cggggcgagg   600
ggcggggcgg ggcgaggcgg agaggtgcgg cggcagccaa tcagagcggc gcgctccgaa   660
agtttccttt tatggcgagg cggcggcggc ggcggcccta taaaaagcga agcgcgcggc   720
gggcgggagc gggatcagcc accgcggtgg cggccctaga gtcgatcgag gaactgaaaa   780
accagaaagt taactggtaa gtttagtctt tttgtctttt atttcaggaa ttctgctgga   840
ggagtgtgtc atacctcggt agggtccact acacatcttt ctcccgcagc ctctccatct   900
tcctgtgact gcgggcgcct cagcctgggc tggccagctg tgagtaattc tttggcagtg   960
tcttagctgg ttgttgtgag tattagctaa ggaagcaatc agcaagtata ctgccctaga   1020
agtgctgcac attgttggac cgagaaggaa aaggtcagag gtcagcaacg cccacacccc   1080
tgagaggcgc tggacttgcg gagctgctcg accatactgg tgggtatggg atggcggccg   1140
cgtcccggat ccggtggtgg tgcaaatcaa agaactgctc ctcagtggat gttgccttta   1200
cttctaggcc tgtacggaag tgttacttct gctctaaaag ctgcggaatt gtacccgcgg   1260
ccgatccacc ggtcgccacc atctagcatg ggagtcaaag ttctgtttgc cctgatctgc   1320
atcgctgtgg ccgaggccaa gcccaccgag aacaacgaag acttcaacat cgtggccgtg   1380
gccagcaact tcgcgaccac ggatctcgat gctgaccgcg ggaagttgcc cggcaagaag   1440
ctgccgctgg aggtgctcaa agagatggaa gccaatgccc ggaaagctgg ctgcaccagg   1500
ggctgtctga tctgcctgtc ccacatcaag tgcacgccca agatgaagaa gttcatccca   1560
ggacgctgcc acacctacga aggcgacaaa gagtccgcac agggcggcat aggcgaggcg   1620
atcgtcgaca ttcctgagat tcctgggttc aaggacttgg agcccatgga gcagttcatc   1680
gcacaggtcg atctgtgtgt ggactgcaca actggctgcc tcaaagggct tgccaacgtg   1740
cagtgttctg acctgctcaa gaagtggctg ccgcaacgct gtgcgacctt tgccagcaag   1800
atccagggcc aggtggacaa gatcaagggg gccggtggtg actagctcga cgctgatcag   1860
cctcgactgt gccttctagt tgccagccat ctgttgtttg cccctccccc gtgccttcct   1920
tgaccctgga aggtgccact cccactgtcc tttcctaata aaatgaggaa attgcatcgc   1980
attgtctgag taggtgtcat tctattctgg ggggtggggt ggggcaggac agcaaggggg   2040
aggattggga agacaattag gtagataagt agcatggcgg gttaatcatt aactacaagg   2100
aacccctagt gatggagttg gccactccct ctctgcgcgc tcgctcgctc actgaggccg   2160
ggcgaccaaa ggtcgcccga cgcccgggct ttgcccgggc ggcctcagtg agcgagcgag   2220
cgcgcag                                                             2227
```